「(12) United States Patent
Gunning et al.

US010889554B2

(10) Patent No.: US 10,889,554 B2
(45) Date of Patent: Jan. 12, 2021

(54) EXCIMER FORMING COMPOUNDS

(71) Applicant: THE GOVERNING COUNCIL OF THE UNIVERSITY OF TORONTO, Toronto (CA)

(72) Inventors: Patrick Thomas Gunning, Mississauga (CA); Dziyana Kraskouskaya, Mississauga (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days.

(21) Appl. No.: 15/102,953

(22) PCT Filed: Dec. 19, 2014

(86) PCT No.: PCT/CA2014/000901
§ 371 (c)(1),
(2) Date: Jun. 9, 2016

(87) PCT Pub. No.: WO2015/089639
PCT Pub. Date: Jun. 25, 2015

(65) Prior Publication Data
US 2016/0304473 A1 Oct. 20, 2016

Related U.S. Application Data

(60) Provisional application No. 61/918,256, filed on Dec. 19, 2013.

(51) Int. Cl.
C12Q 1/6816 (2018.01)
G01N 33/68 (2006.01)
G01N 33/52 (2006.01)
C07D 257/02 (2006.01)
C07C 233/44 (2006.01)
C07C 233/80 (2006.01)
C07D 403/10 (2006.01)
C07D 401/12 (2006.01)
C09B 57/00 (2006.01)
C09B 1/00 (2006.01)
C07C 309/65 (2006.01)
C07D 213/38 (2006.01)

(52) U.S. Cl.
CPC .......... C07D 257/02 (2013.01); C07C 233/44 (2013.01); C07C 233/80 (2013.01); C07C 309/65 (2013.01); C07D 213/38 (2013.01); C07D 401/12 (2013.01); C07D 403/10 (2013.01); C09B 1/00 (2013.01); C09B 57/00 (2013.01); C09B 57/001 (2013.01); C12Q 1/6816 (2013.01); G01N 33/52 (2013.01); G01N 33/6842 (2013.01); G01N 2440/14 (2013.01)

(58) Field of Classification Search
CPC ... C12Q 1/6816; G01N 33/52; G01N 33/6842
See application file for complete search history.

(56) References Cited

U.S. PATENT DOCUMENTS

2004/0038306 A1 2/2004 Agnew et al.

OTHER PUBLICATIONS

Schmidt et al. "Zinc-cyclen coordination to UTP, TTP or pyrophosphate induces pyrene excimer emission" Dalton Transactions, 2010, vol. 39, pp. 7250-7261.*
Bishop et al. "The Nucleotides in Normal Human Blood" J. Biol. Chem., 1959, vol. 234, pp. 1233-1237.*
Habata et al. "Argentivorous Molecules Bearing Two Aromatic Side-Arms: Ag+-π and CH-π Interactions in the Solid State and in Solution" Inorganic Chemistry, 2013, vol. 52, pp. 2542-2549.*
Hunter, T. Protein kinases and phosphatases: the yin and yang of protein phosphorylation and signaling. Cell 80, 225-236 (1995).
Cohen, P. Protein kinases—the major drug targets of the twenty-first century? Nat Rev Drug Discov 1, 309-315 (2002).
Su, H.-C., Hutchison, C. A & Giddings, M. C. Mapping phosphoproteins in Mycoplasma genitalium and Mycoplasma pneumoniae. BMC Microbiol. 7, 63 (2007).
Orsatti, L. et al. 2-D Difference in gel electrophoresis combined with Pro-Q Diamond staining: A successful approach for the identification of kinase/phosphatase targets. Electrophoresis 30, 2469-2476 (2009).
Steinberg, T. H. et al. Global quantitative phosphoprotein analysis using Multiplexed Proteomics technology. Proteomics 3, 1128-1144 (2003).
Lucet I. S. et al. The structural basis of Janus kinase 2 inhibition by a potent and specific pan-Janus kinase inhibitor. Blood 107, 176-183 (2006).
Dephoure, N. et al. A quantitative atlas of mitotic phosphorylation. Proc. Natl. Acad. Sci. U.S.A. 105, 10762-10767 (2008).
Cho, H. K., Lee, D. H. & Hong, J.-I. A fluorescent pyrophosphate sensor via excimer formation in water. Chem. Commun. (Camb.) 1690-1692 (2005). doi:10.1039/b417845a.
Aoki, S., Kaldo, S., Fujioka, H. and Kimura, E. A New Zinc(II) Fluorophore 2-(9-Anthrylmethylamino)ethyl-Appended 1,4,7,10-Tetraazacyciododecane. Inorganic Chemistry, 42(4):1023-1030, 2003.
Baek, K., Eom M.S., Kim, S., Han, M.S. Metal ion-prompted pyrene-excimer formation via an anion-mediated process and its application for a ratiometric Zn2+ chemosensor with high selectivity over Cd2+. Tetrahedron Letters, 54:1654-1657, 2013.
Bhattacharya, S. and Gulyani, A. First report of Zn2+ sensing exclusively at mesoscopic interfaces. Chem. Commun. 10:1158-1159, 2003.

(Continued)

Primary Examiner — Joseph R Kosack
(74) Attorney, Agent, or Firm — Bereskin & Parr LLP/S.E.N.C.R.L., s.r.l.; Michael Fenwick

(57) ABSTRACT

The present application is directed to excimer forming compounds of Formula I: W—V—[Y]$_n$ wherein W is an excimer forming fluorophore, V is a linker moiety, Y is a metal ion coordinating moiety and n is 1, 2 or 3. In particular, the application is directed to excimer forming compounds for the detection of proximally phosphorylated sites including those found on polypeptides, proteins, pyrophosphate and RNA, for example in aqueous solution, polyacrylamide gels blotting membranes, solid-support assays and in cell culture samples.

20 Claims, 64 Drawing Sheets

(56) References Cited

OTHER PUBLICATIONS

Kikuta, E., Murata, M., Katsube, N., Koike, T., Kimura, E. Novel Recognition of Thymine Base in Double-Stranded DNA by Zinc(II)-Macrocyclic Tetraamine Complexes Appended with Aromatic Groups. J. Am. Chem. Soc. 121:5426-5436, 1999.

Kraskouskaya, D., Bancerz, M., Soar, H.S., Gardiner, J.E., and Gunning, P.T. An Excimer-Based, Turn-On Fluorescent Sensor for the Selective Detection of Diphosphorylated Proteins in Aqueous Solution and Polyacrylamide Gels. J. Am. Chem. Soc. 136:1234-1237, 2014.

Kumar, T.S., Myznikova, A., Samokhina, E. and Astakhova, I.K. Rapid genotyping using pyrene-perylene locked nucleic acid complexes. Artificial DNA: PNA & XNA 4:(2):58-68; Apr./May/Jun. 2013.

Massue, J., Plush, S.E., Bonnet, C.S., Moore, D.A. and Gunnlaugsson, T. Selective:: mono N-alkylationg of cyclen in. one step syntheses. Tetrahedron Letters 48:8052-8055, 2007.

Oh, K.J. Cash, K.J. and Plaxco, K.W. Excimer-Based Peptide Beacons: A Convenient Experimental Approach for Monitoring Polypeptide—Protein and Polypeptide—Oligonucleotide Interaction. J. Am. Chem. Soc. 128:14018-14019, 2006.

Schmidt, F., Stadlbauer, S. & Konig, B. Zinc-cyclen coordination to UTP, TTP or pyrophosphate induces pyrene excimer emission. Dalton Trans. 39, 7250-7261 (2010).

Skwierawska, A. Convenient synthesis of novel mono- and bi-functional fluorescent. J. Supramol. Chem. 1:239-243, 2001 (Abstract).

Umemoto, T., Hrdlicka, P.J., Badu, B.R. and Wengel, J. Sensitive SNP Dual-Probe Assays Based on Pyrene-Functionalized 2I-Amino-LNA: Lessons to Be Learned. ChemBioChem, 8:2240-2248, 2007.

Cabral, A.D., et al., Structure-activity relationship study of ProxyPhos chemosensors for the detection of proximal phosphorylation and other phosphate species, Analyst, 2017, 142, 3922-3933.

\* cited by examiner

A

B

A

B

C

Analyte concentration (μM)

EXCIMER FORMING COMPOUNDS

RELATED APPLICATIONS

This application is a national phase entry of PCT/CA2014/000901, filed Dec. 19, 2014, which claims the benefit of priority of U.S. provisional patent application No. 61/918,256 filed on Dec. 19, 2013, the contents of which are incorporated herein by reference in their entirety.

FIELD

The present application is directed to excimer forming sensor compounds. In particular, the application is directed to excimer forming sensor compounds for the detection of proximally phosphorylated sites including those found on proteins, pyrophosphate and RNA.

INTRODUCTION

Protein phosphorylation is a ubiquitous post-translation modification, which serves, amongst other roles, as a switch to control proteins' activation state.[1] Significantly, perturbed protein phosphorylation levels and/or the overexpression of phosphorylated proteins in signaling pathways are the hallmark of many human disease.[2] Thus, development of molecular methods for the detection and quantification of phosphorylated proteins is of utmost interest and importance.

Pro-Q Diamond, a commercially available fluorescent phospho-protein stain, has been applied for studying the phospho-proteome[3] and for identification of kinase/phosphatase targets.[4] Although highly efficient at determining the total phosphorylation levels (staining all tyrosine (pY), serine (pS) and threonine (pT) residues),[5] it offers no information about the spatial arrangement of these phosphorylated sites.

Di-phosphorylation on proximal residues is required for the activation of a subset of proteins including, Jak2[6] and ERK2[7] kinases, resulting in pYpY and pTXpY motifs, respectively (X=any amino acid). Importantly, many of these activated kinases are overexpressed in a variety of diseases, notably human cancers.[2] Therefore, a sensor capable of detecting proximal phosphorylated residues will provide valuable information about specific protein activation status and serve as a molecularly targeted diagnostic tool for disease detection.

SUMMARY

The present application describes a turn-on dual emission fluorescent sensor which selectively detects proximally phosphorylated sites including those found on proteins, pyrophosphate and RNA, for example in aqueous solutions and, polyacrylamide gels, blotting membranes, solid-support assays and in cell culture samples.

In one embodiment, the turn-on dual emission fluorescent sensor is an excimer forming compound, in which the sensor is comprised of an excimer forming fluorophore. When two or more of the excimer forming fluorophores overlap or otherwise associate, a bathochromic shift in emission occurs, thereby increasing fluorescence intensity of the excimer-state fluorophore, indicating the presence of at least two proximally phosphorylated sites.

In one embodiment, the present disclosure includes an excimer forming compound of the Formula I

(I)

wherein,
W is an excimer forming fluorophore;
V is a linker moiety;
Y is a metal ion coordinating moiety; and
n is 1, 2 or 3.

In one embodiment, the present disclosure includes an excimer forming compound of the Formula Ia $$W-V+Y]_n \qquad (Ia)$$

wherein,
W is an excimer forming fluorophore;
V is a linker moiety;
Y is a metal ion coordinating moiety containing a metal ion, for example a transition, post-transition or a lanthanide metal ion;
n is 1, 2 or 3

In one embodiment, the present disclosure also includes a composition comprising a compound of the Formula (I) and a suitable metal ion.

In a further embodiment, the present disclosure also includes an aqueous composition comprising a compound of the Formula (I) and a suitable metal ion.

In one embodiment, the present disclosure includes a binding solution, comprising:
(a) an excimer-forming Compound of the Formula I, and
(b) a suitable metal ion, and
optionally, other additives such as salts, buffers or other organic components.

In another embodiment, the present disclosure includes a binding solution Ia, comprising:
(a) an excimer-forming compound of the Formula Ia, and
optionally, other additives such as salts, buffers or other organic components.

In another embodiment, the disclosure includes a method of detecting proximal phosphorylation of a polypeptide comprising:
(a) contacting a polypeptide sample with a binding solution of the disclosure (wherein the binding solution comprises a compound of the Formula I and a suitable metal ion);
(b) detecting a fluorescence signal at a wavelength specific for the excimer forming fluorophore of the compound present in the binding solution of the disclosure;
wherein detection of a signal having a fluorescence intensity greater than a signal of a sample containing distal phosphorylation, mono-phosphorylation or no phosphorylation indicates that the polypeptide contains phosphorylation of at least two sites proximal to each other.

In a further embodiment, the disclosure includes a method of detecting proximal phosphorylation of a polypeptide comprising:
(a) contacting a polypeptide sample with a binding solution of the disclosure (wherein the binding solution comprises a compound of the Formula I and a suitable metal ion);
(b) detecting a fluorescence signal at a wavelength specific for the excimer forming fluorophore of the compound present in the binding solution of the disclosure;
(c) comparing the fluorescence signal of (b) with the fluorescence intensity of a distally phosphorylated, monophosphorylated or unphosphorylated control;
wherein detection of a signal having a fluorescence intensity greater than the control indicates that the polypeptide contains phosphorylation of at least two sites proximal to each other.

In yet another embodiment, there is provided a method of quantifying proximal phosphorylation comprising:

(a) contacting a sample with a binding solution of the disclosure (wherein the binding solution comprises a compound of the Formula I and a suitable metal ion);
(b) detecting a fluorescence signal at a wavelength specific for the excimer forming fluorophore of the compound present in the binding solution of the disclosure;
(c) comparing the fluorescence signal of (b) with the fluorescence intensity of control samples of known quantities of proximal phosphorylation;

wherein detection of a signal having a fluorescence intensity similar to one of the control samples indicates the amount of proximal phosphorylation in the sample.

In one embodiment, the amino acids that are proximally phosphorylated are within 1-10 amino acid residues of each other, optionally within 1-4 amino acid residues of each other, or are otherwise found proximal through space as a result of secondary and tertiary folding.

The polypeptide sample may be a protein extract from a cell line, such as a prokaryotic cell line (for example a bacterial cell line), a yeast cell line, a eukaryotic cell line, or the polypeptide sample may be obtained from a subject, such as a human, suffering from a disease associated with increased proximal phosphorylation or pyrophosphate of proteins. In another embodiment, the polypeptide sample is a sample synthesized using a peptide synthesizer or is a sample from a genetically modified protein expressed on a vector.

In yet a further embodiment, there is provided a method of assessing the activation status of a protein that is activated by proximal phosphorylation comprising:
(a) contacting a sample of the protein with a binding solution of the disclosure (wherein the binding solution comprises a compound of the Formula I and a suitable metal ion);
(b) detecting a fluorescence signal at a wavelength specific for the excimer forming fluorophore of the compound present in the binding solution of the disclosure;
(c) comparing the fluorescence signal of (b) with the fluorescence intensity of an unactivated protein sample;

wherein detection of a signal having a fluorescence intensity greater than the unactivated protein sample indicates that the protein sample is activated. In one embodiment, the protein that is activated by proximal phosphorylation is an enzyme or a kinase, such as Jak2 or Erk2.

In another embodiment, the disclosure provides a method of detecting pyrophosphates comprising:
(a) contacting a sample with a binding solution of the disclosure (wherein the binding solution comprises a compound of the Formula I and a suitable metal ion);
(b) detecting a fluorescence signal at a wavelength specific for the excimer forming fluorophore of the compound present in the binding solution of the disclosure;
(c) comparing the fluorescence signal of (b) with the fluorescence intensity of a control sample;

wherein detection of a signal having a fluorescence intensity greater than the control sample indicates that the protein sample contains pyrophosphates.

Also provided is a method of quantifying pyrophosphates comprising:
(a) contacting a sample with a binding solution of the disclosure (wherein the binding solution comprises a compound of the Formula I and a suitable metal ion);
(b) detecting a fluorescence signal at a wavelength specific for the excimer forming fluorophore of the compound present in a binding solution of the disclosure;
(c) comparing the fluorescence signal of (b) with the fluorescence intensity of control samples of known quantities of pyrophosphates;

wherein detection of a signal having a fluorescence intensity similar to one of the control samples indicates the amount of pyrophosphates in the sample.

In an embodiment, the sample for pyrophosphate detection or quantification is a bodily sample, such as urine, synovial fluid or blood. In one embodiment, the sample is used in a assay for the detection and/or quantification of the release or consumption of PPi, such as an assay measuring ATP consumption, which is used to monitor enzyme activity or a PCR reaction to monitor the progress of the reaction by release of PPi.

In some embodiments, the methods disclosed herein are performed in solution. In other embodiment, the methods disclosed herein are performed in a gel or a membrane, other solid support assay, or in fixed or live cells.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

DRAWINGS

The present disclosure will now be described in greater detail with reference to the following drawings in which:

FIG. 1 is (A) a schematic representation of a compound of the Formula Ia demonstrating binding to one or two phosphorylation sites; and (B) is the chemical structure of the compound referred to in FIG. 1A;

FIG. 2 is (A) an emission spectrum resulting from contacting a binding solution in one embodiment of the disclosure with proximally phosphorylated sites; (B) a graph showing the fluorescence emission factor versus log peptide concentration demonstrating detection of proximally phosphorylated sites; and (C) a fluorescence image of a binding solution in one embodiment of the disclosure detecting proximally phosphorylated sites;

Figure 20:
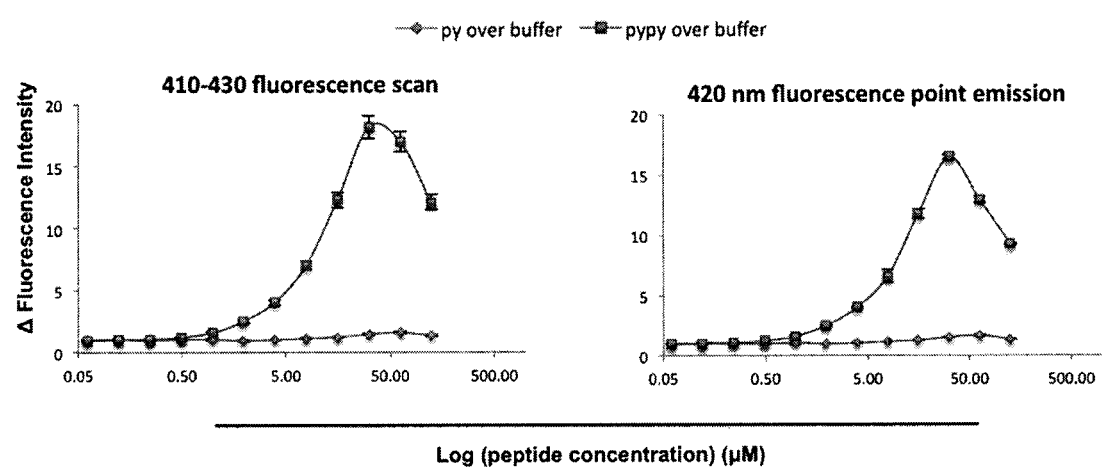
Figure 21:
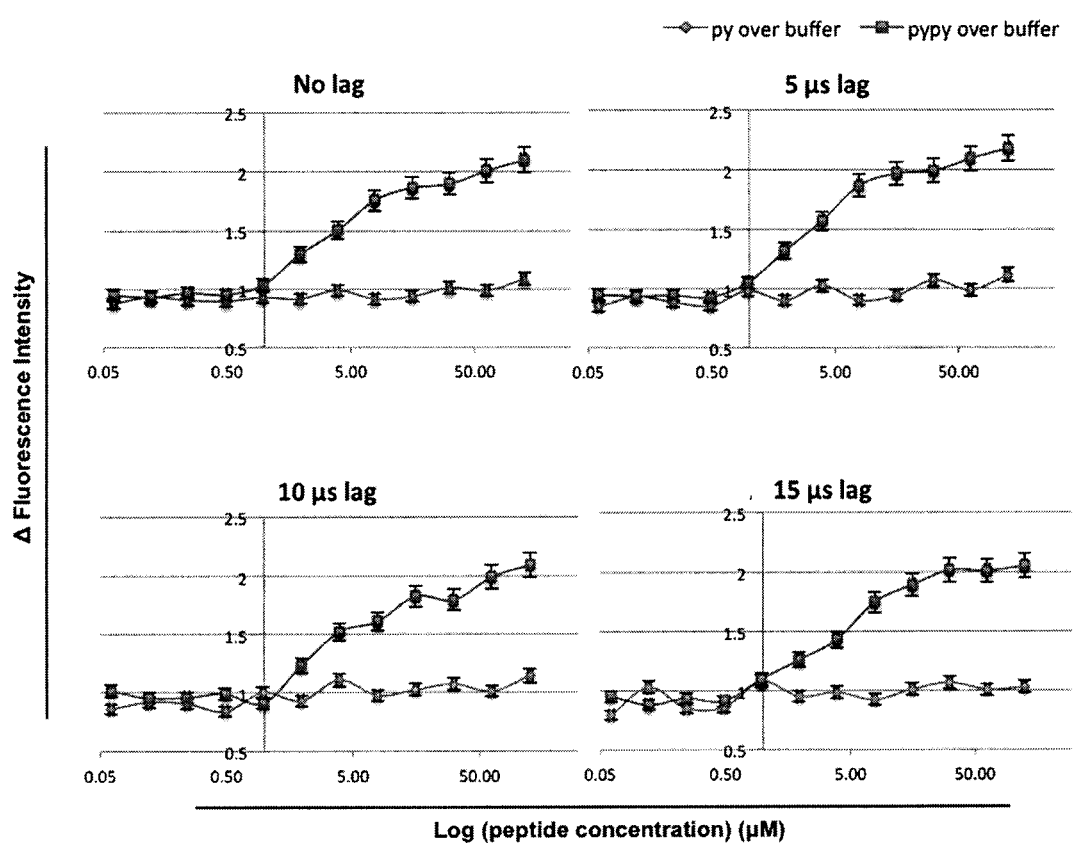
Figure 22:
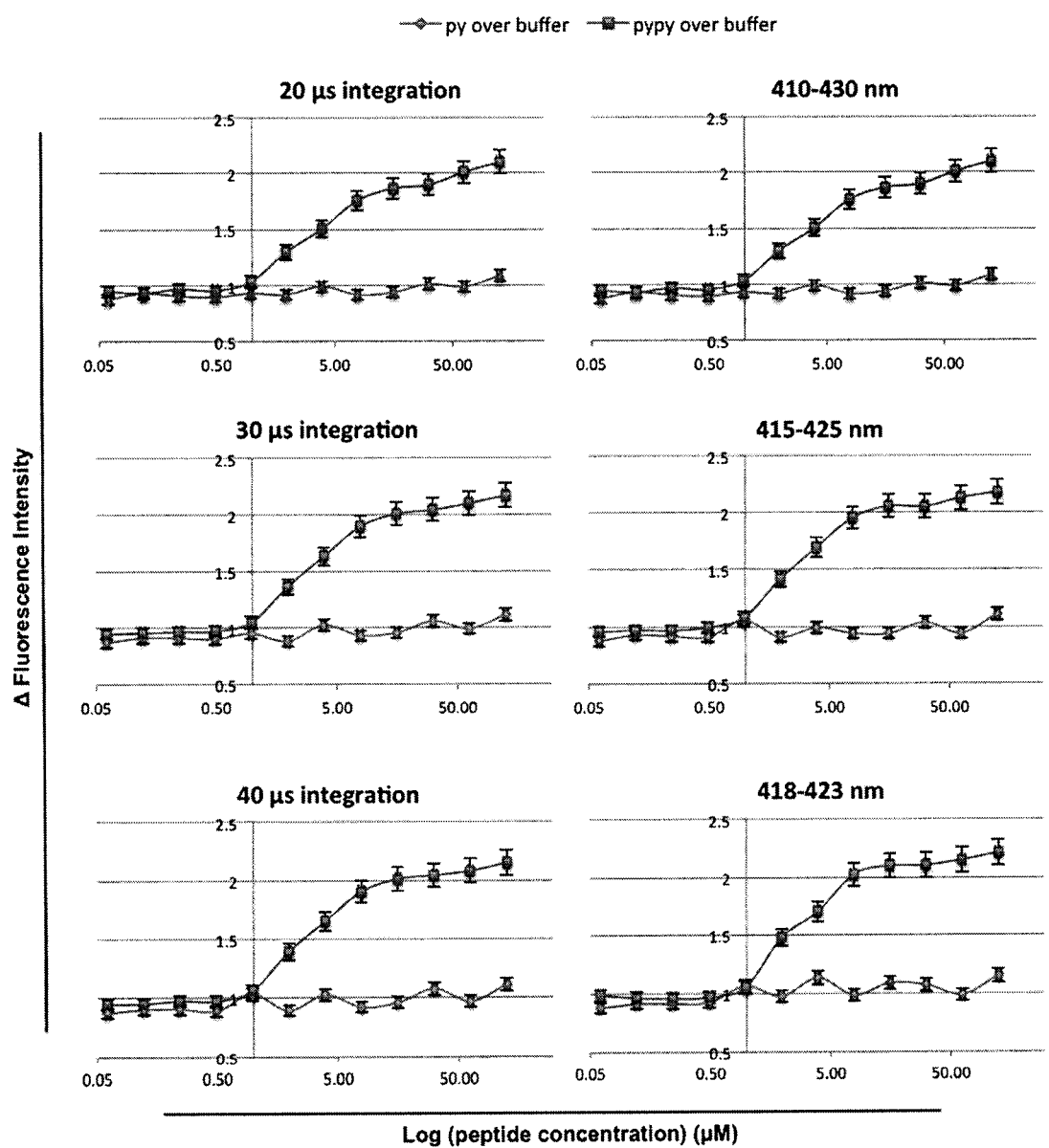
Figure 23:
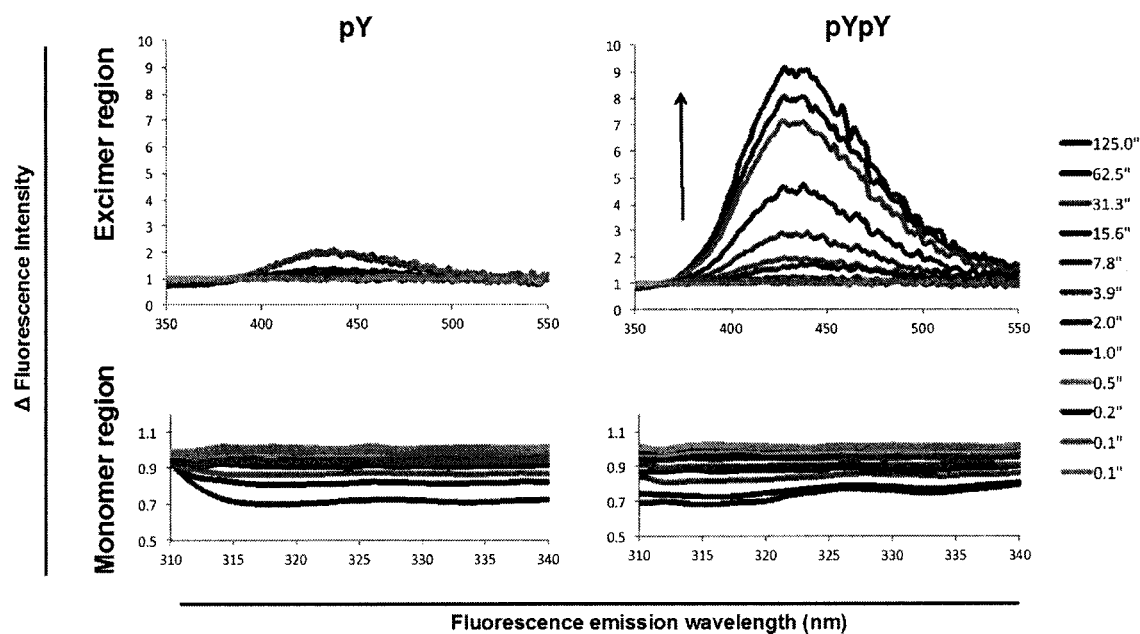
Figure 24:
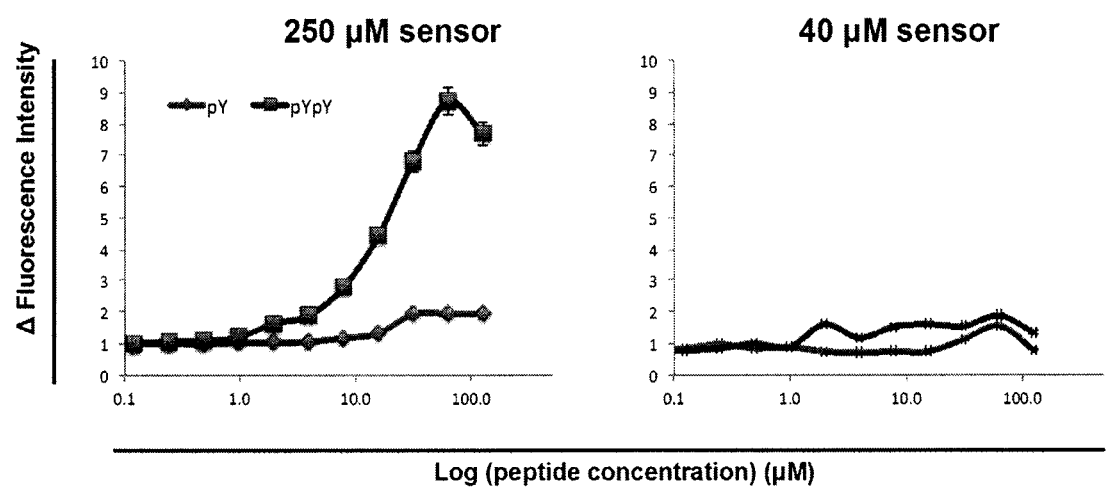
Figure 25:
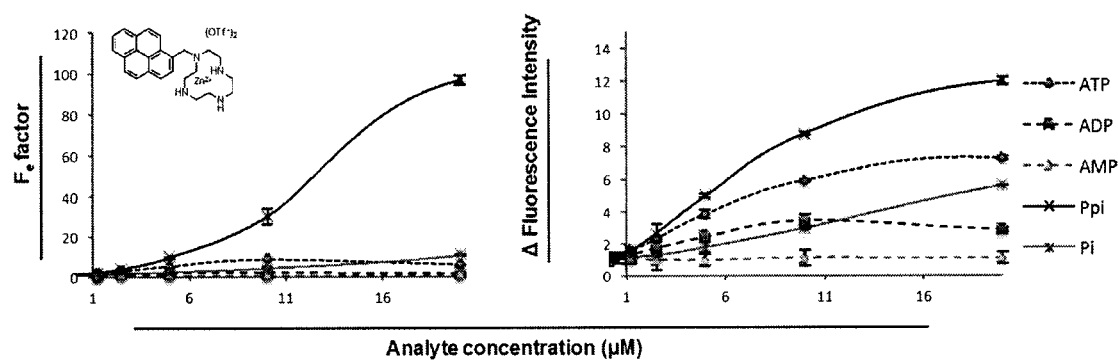
Figure 26:
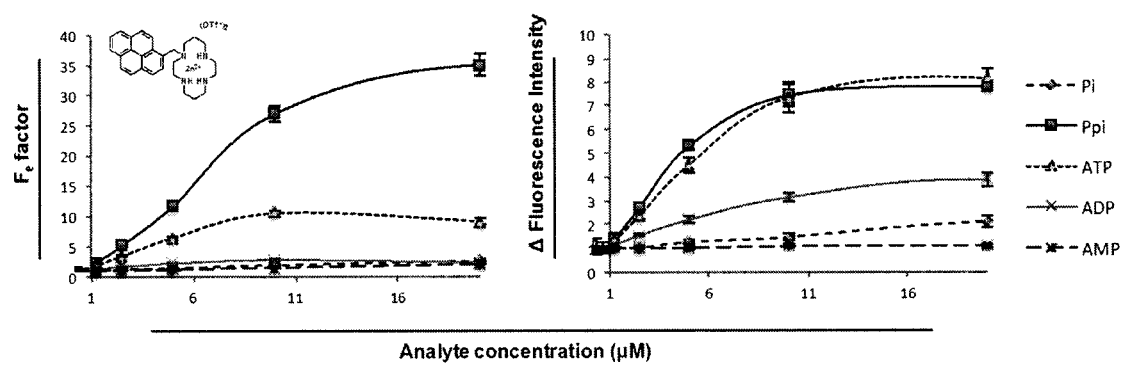
Figure 27:
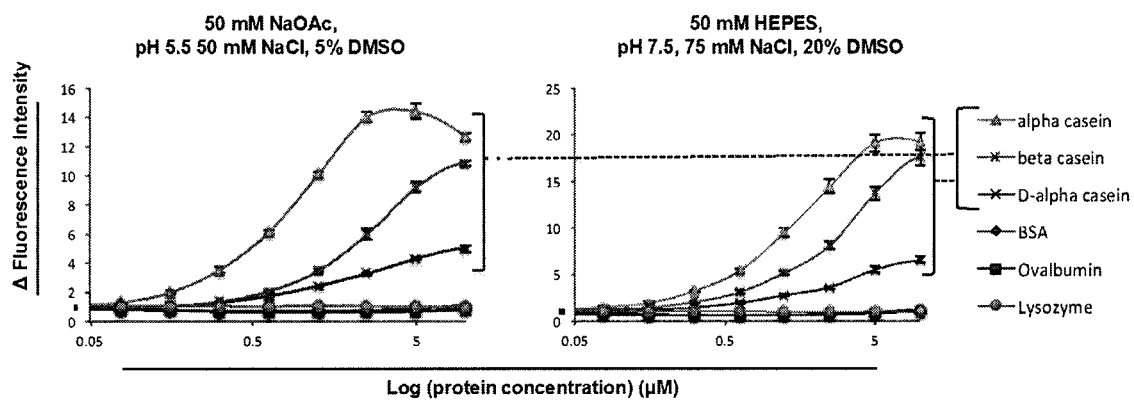
Figure 28:
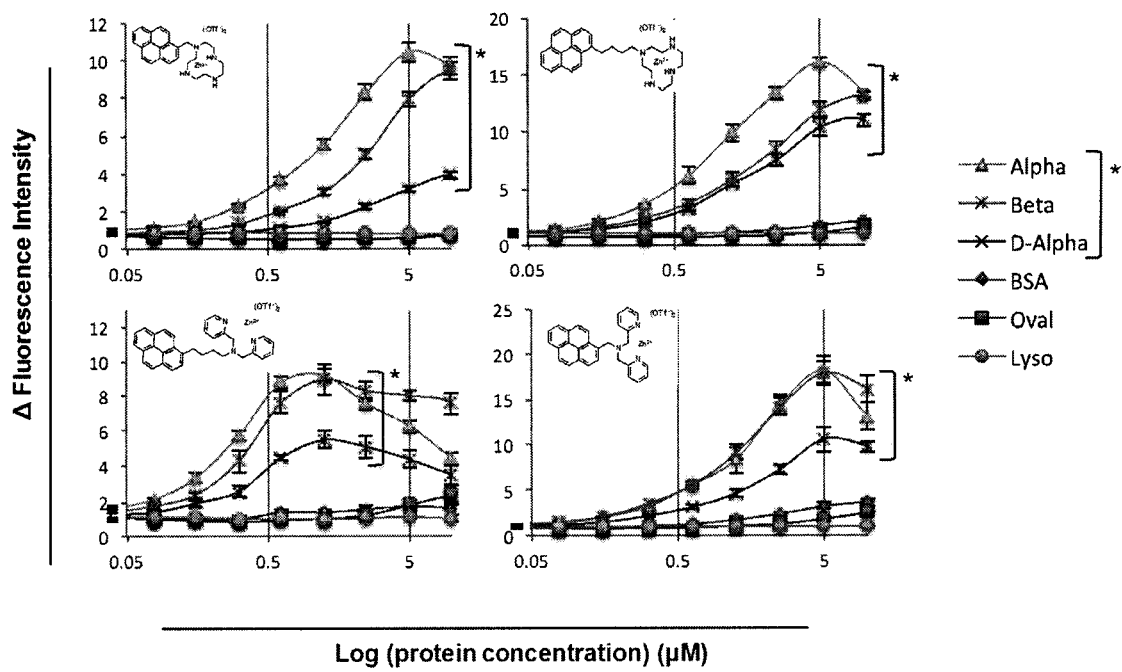
Figure 29:
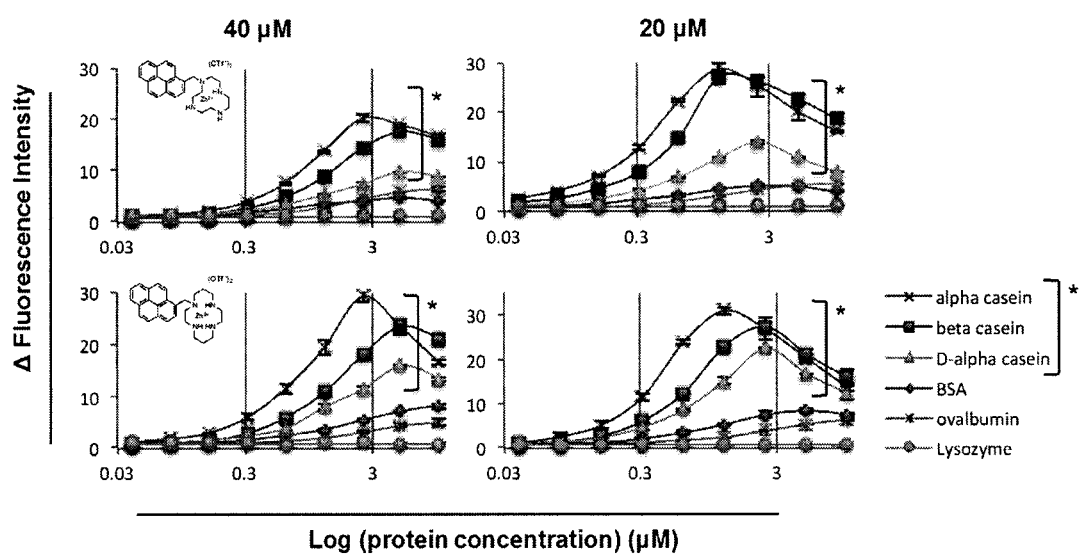
Figure 30:
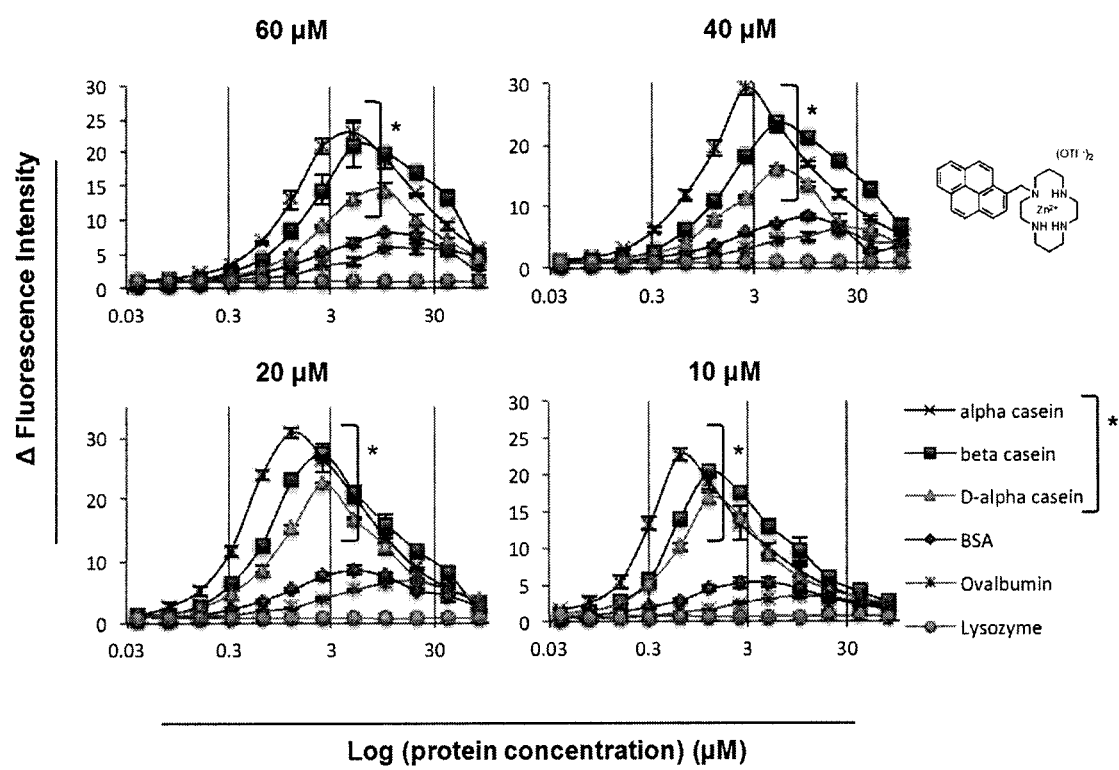
Figure 31:
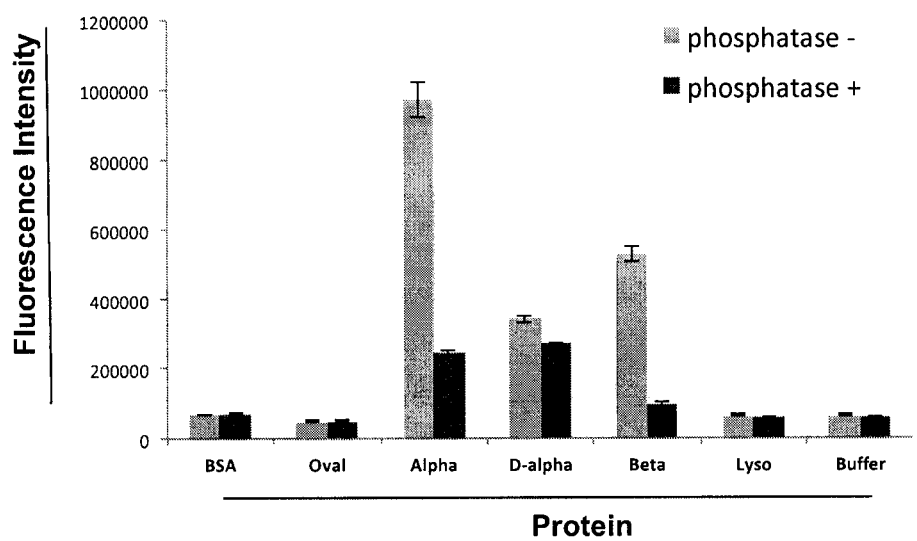
Figure 32:
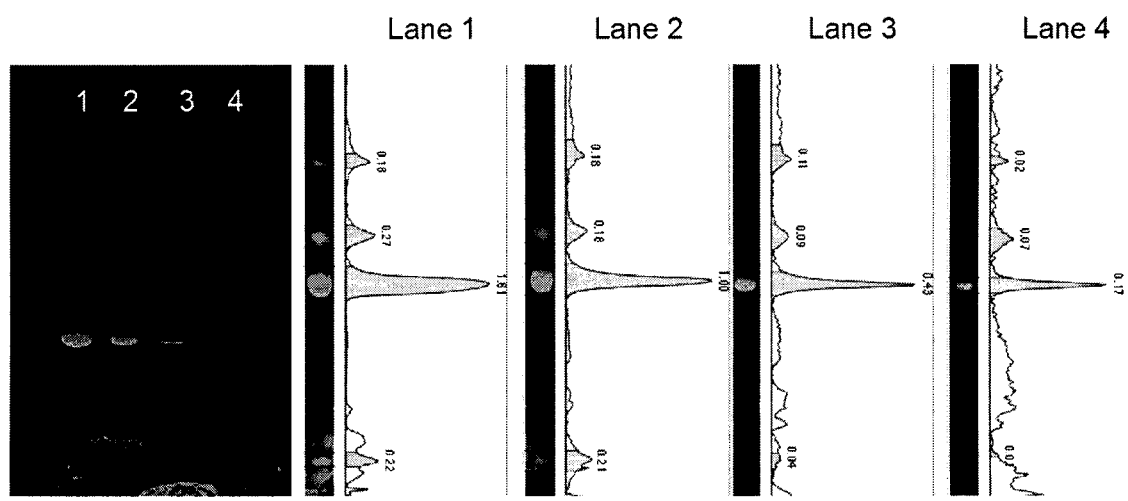
Figure 33:
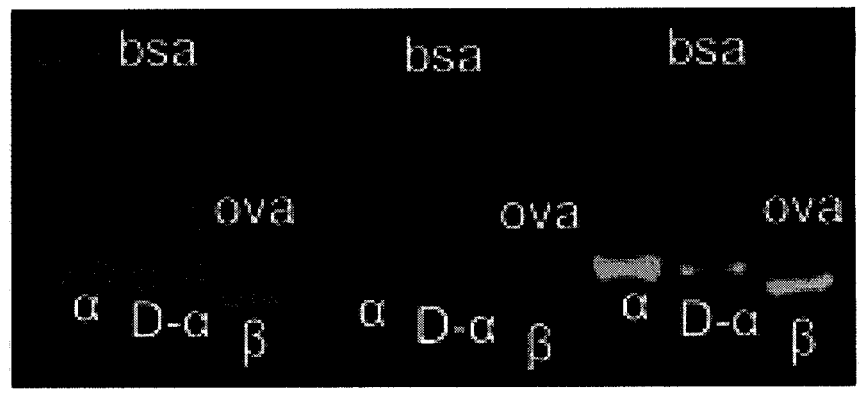
Figure 34:
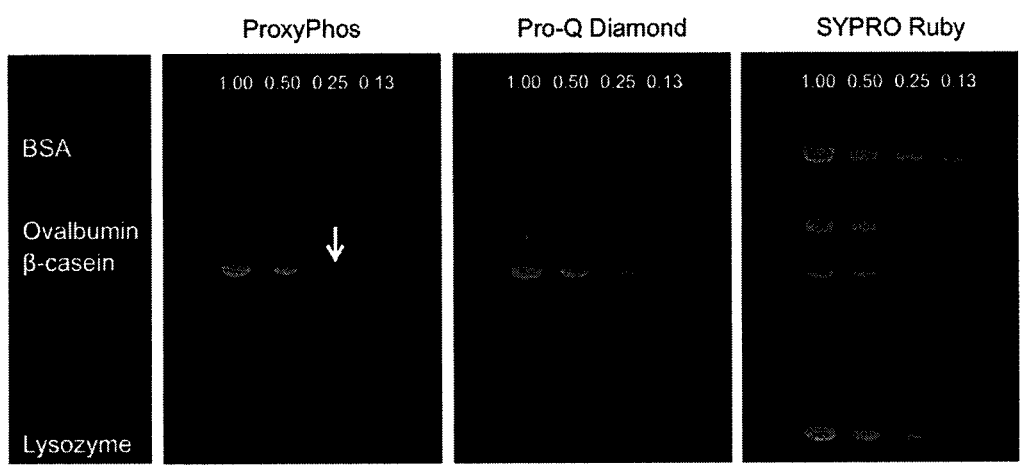
Figure 35:
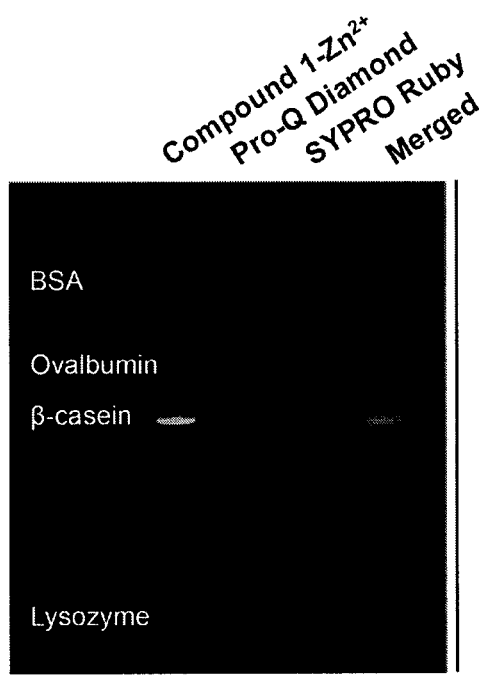
Figure 36:
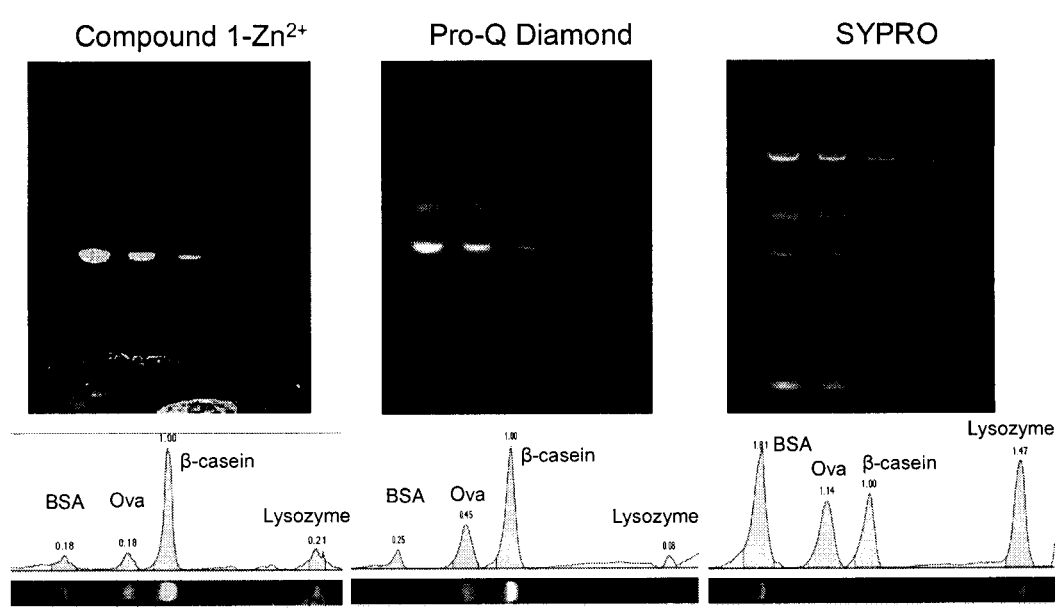
Figure 37:
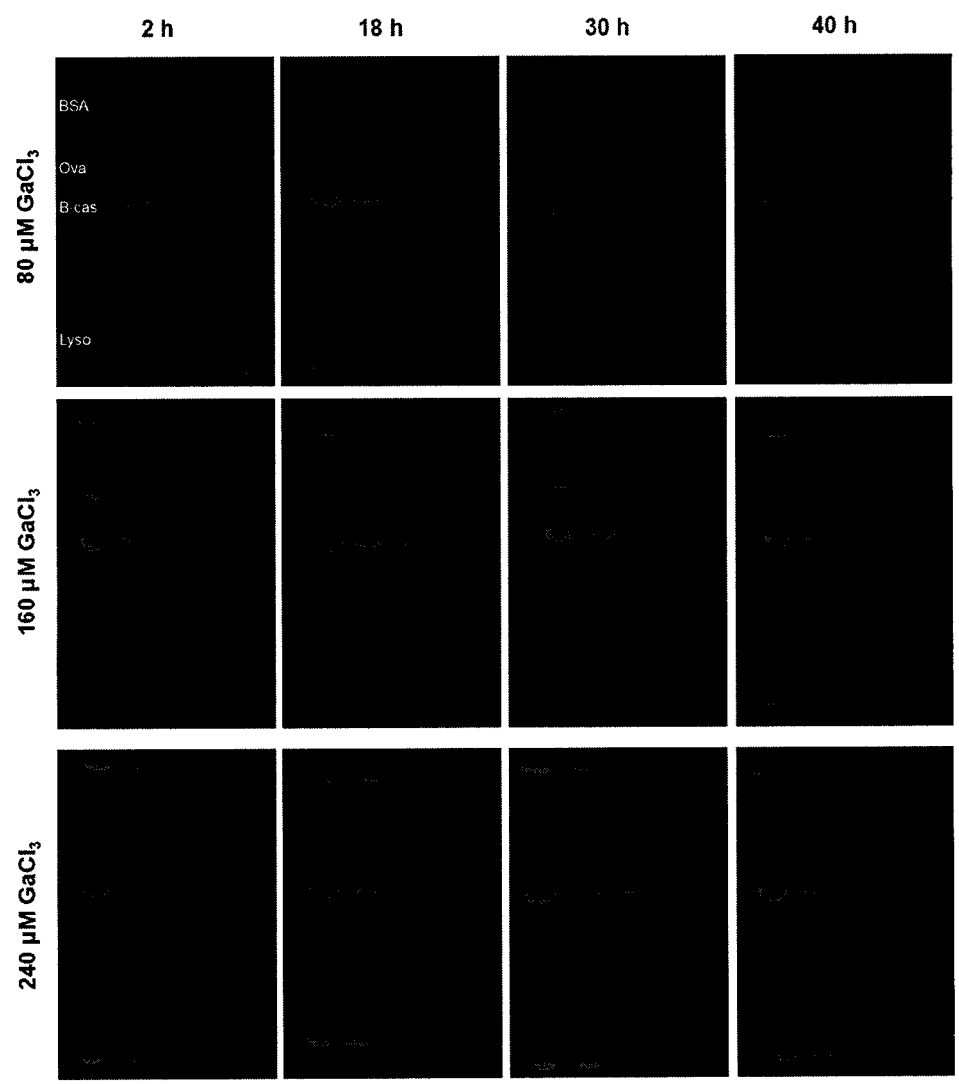
Figure 38:
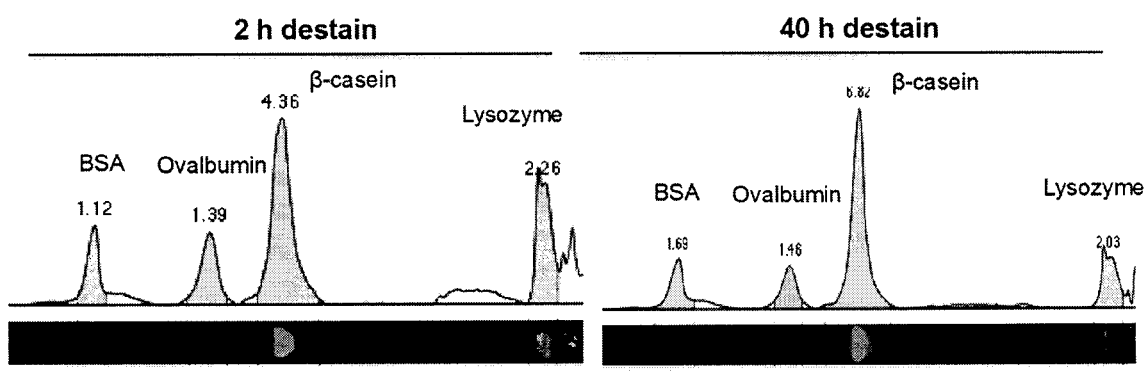
Figure 39:
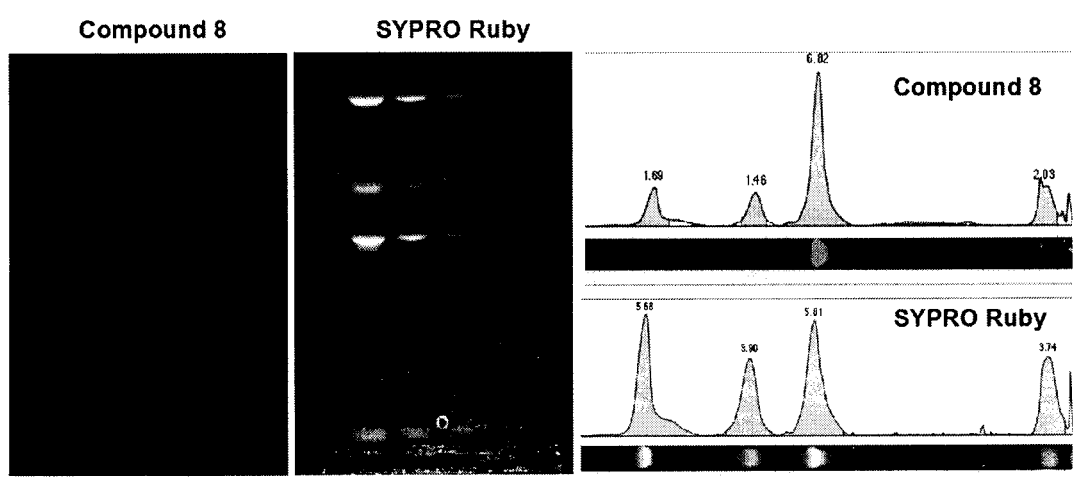
Figure 40:
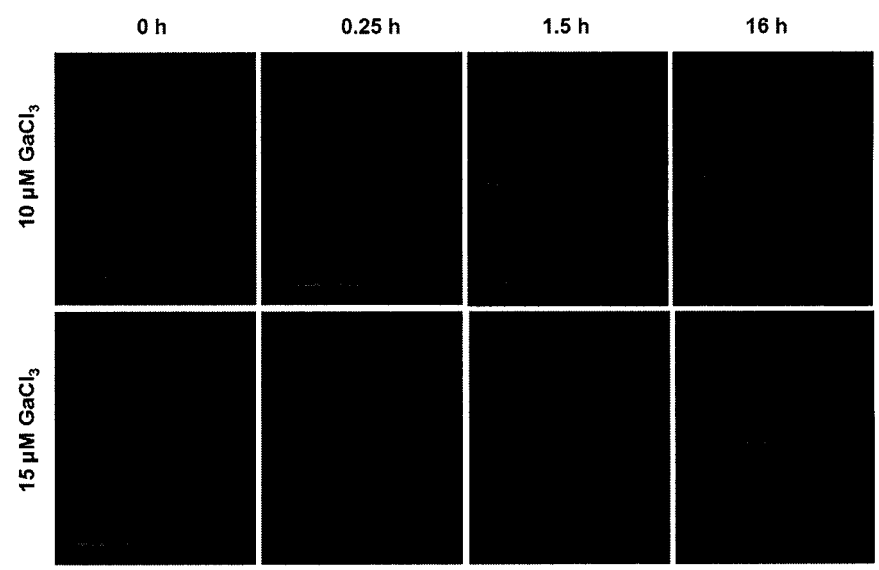
Figure 41:
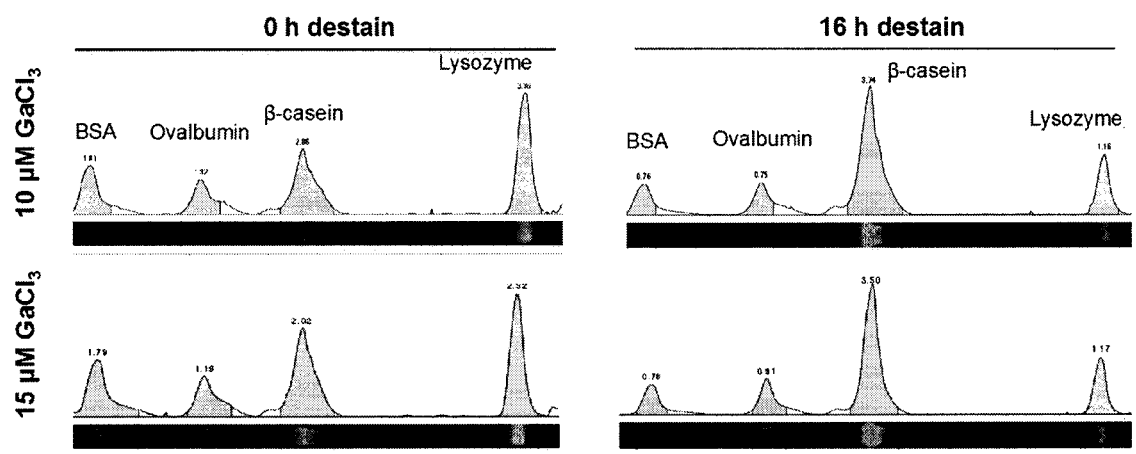
Figure 42:
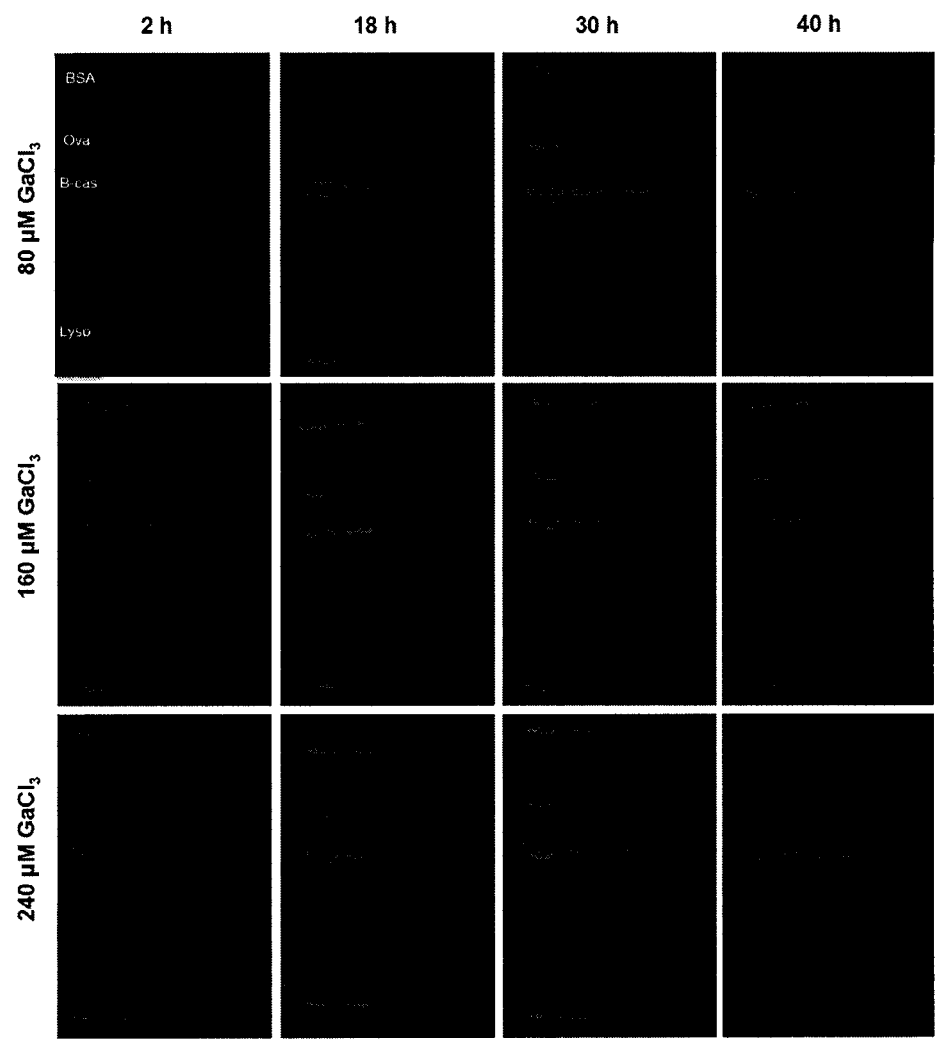
Figure 43:
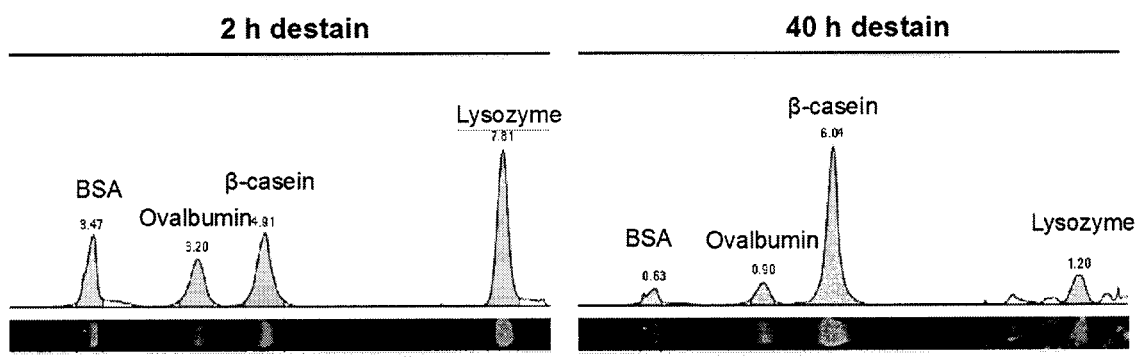
Figure 44:
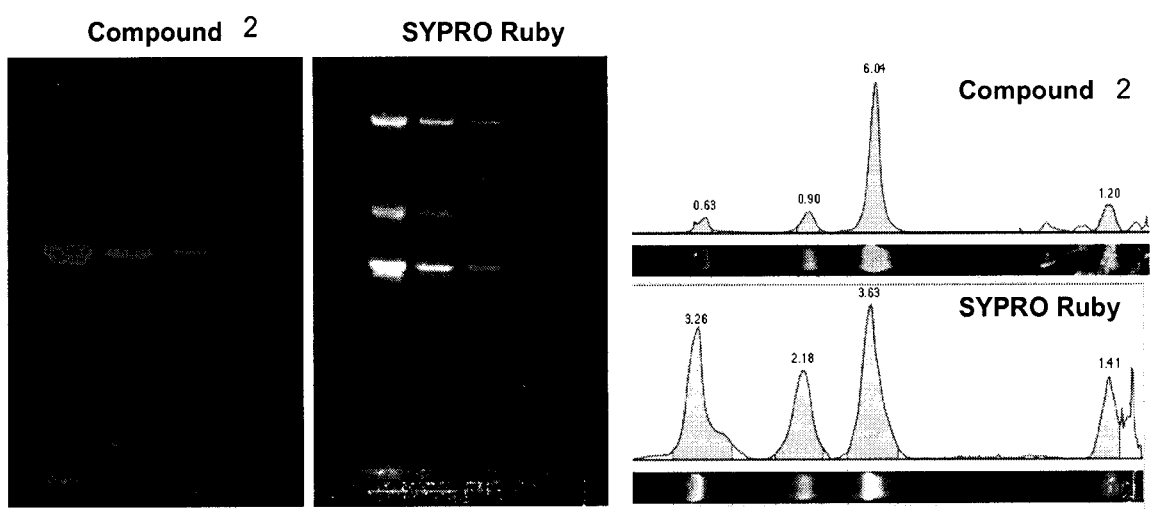
Figure 45:
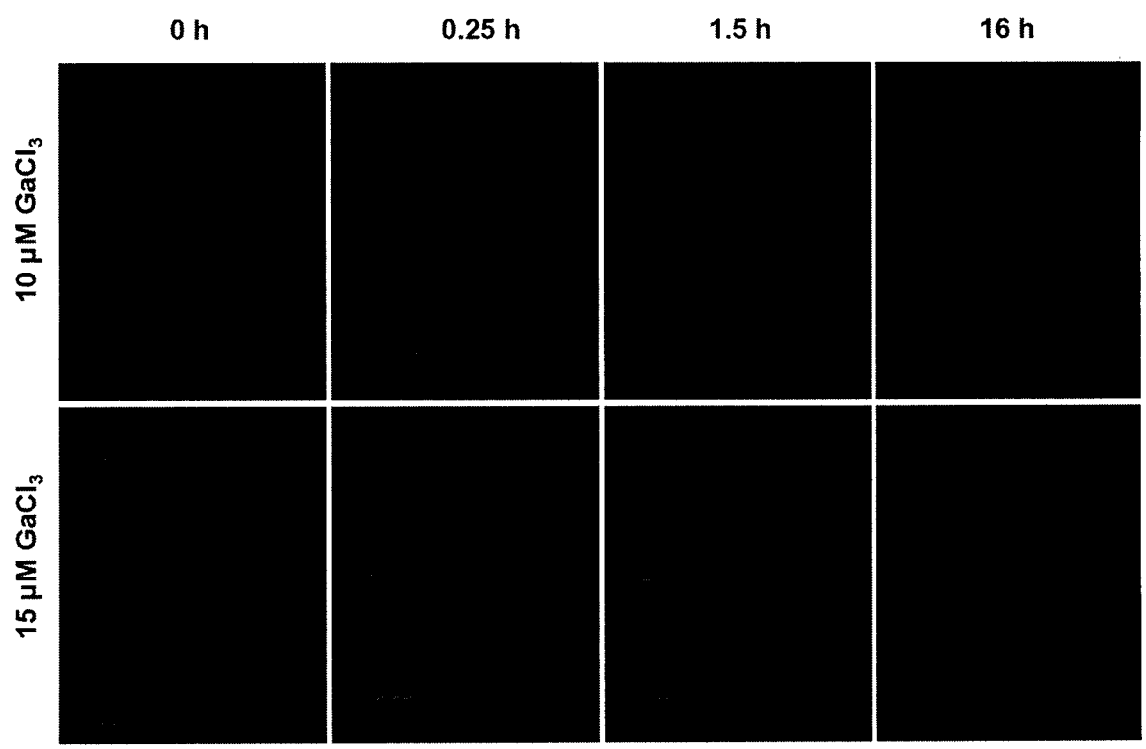
Figure 46:
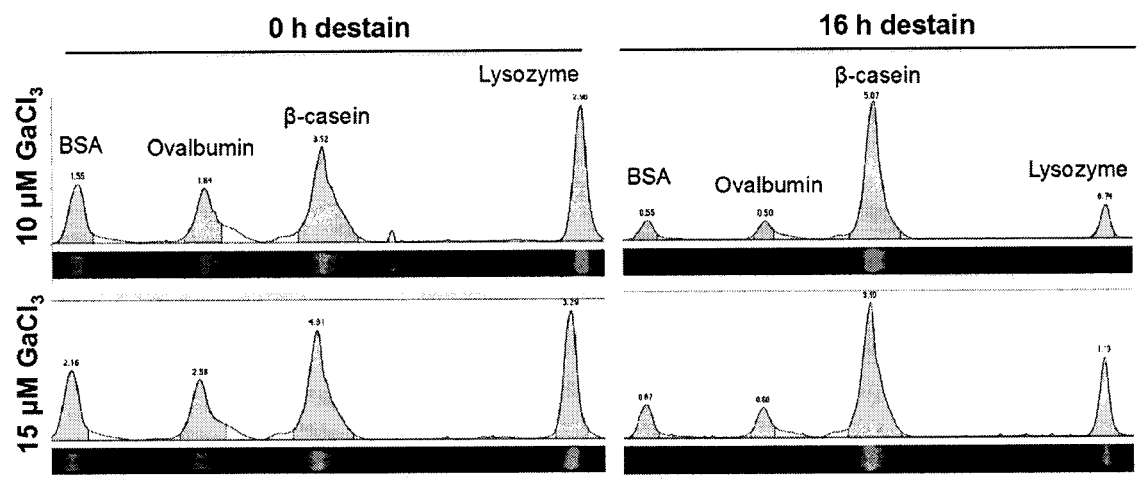
Figure 47:
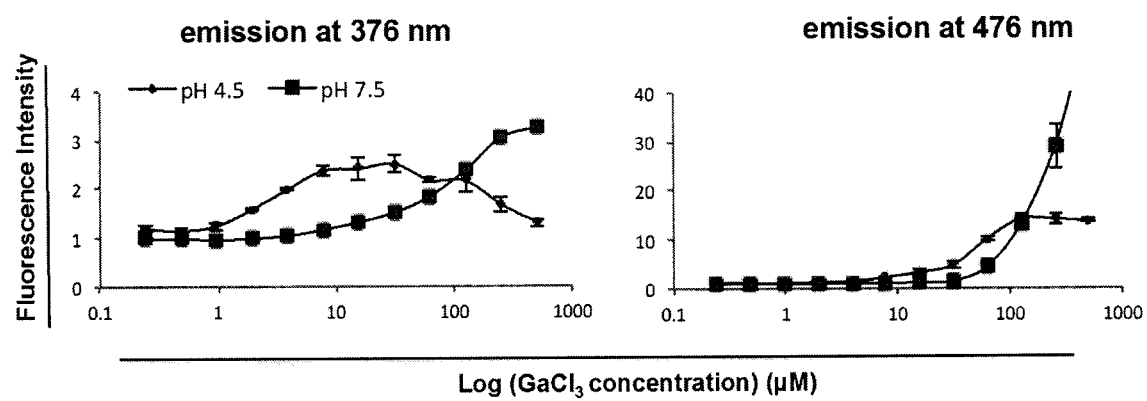
Figure 48:
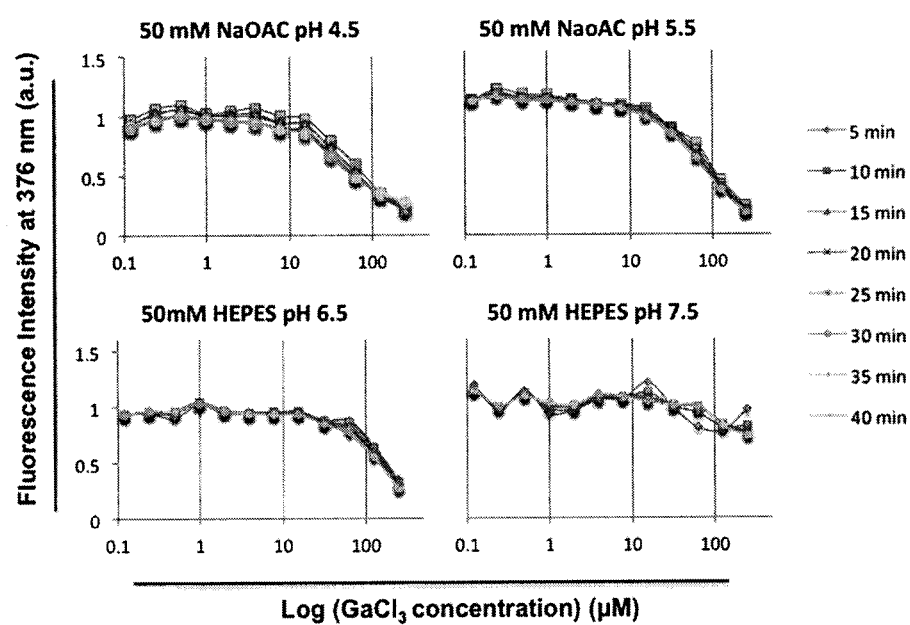
Figure 49:
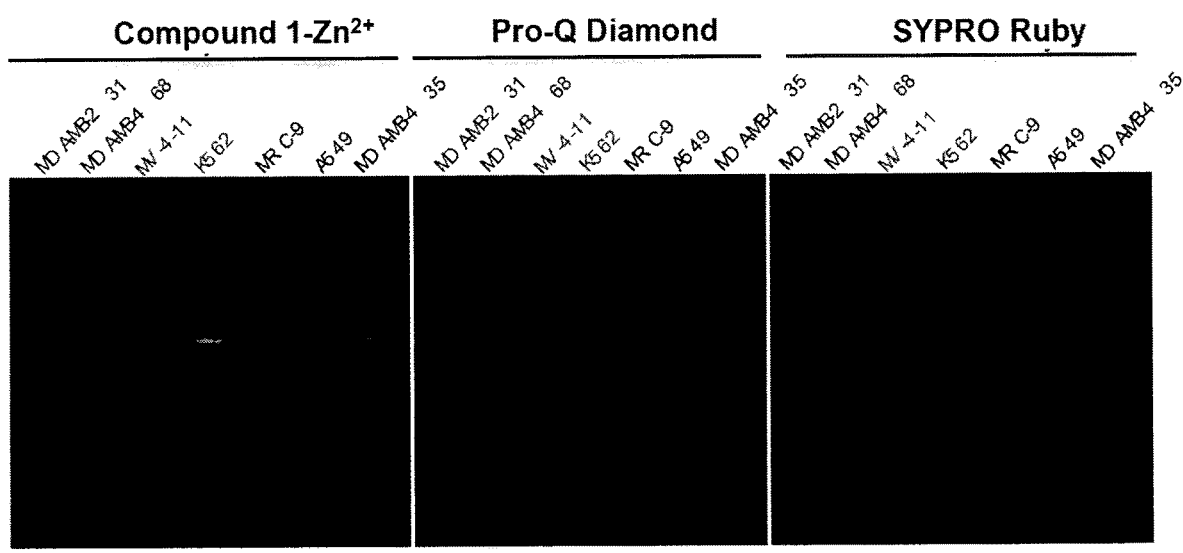
Figure 50:
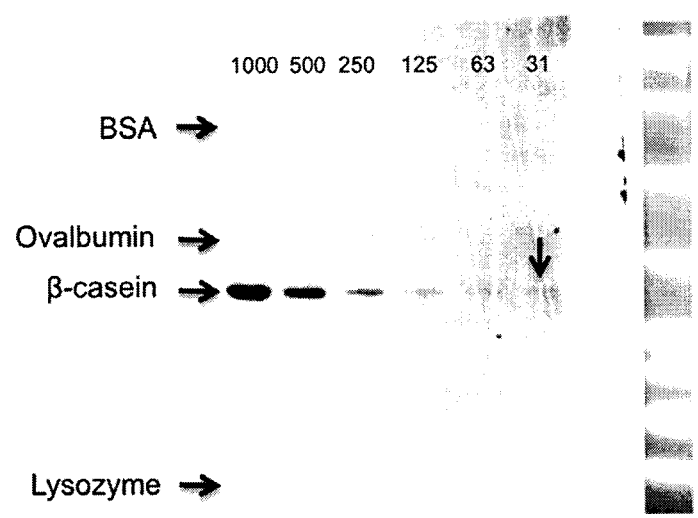
Figure 51:
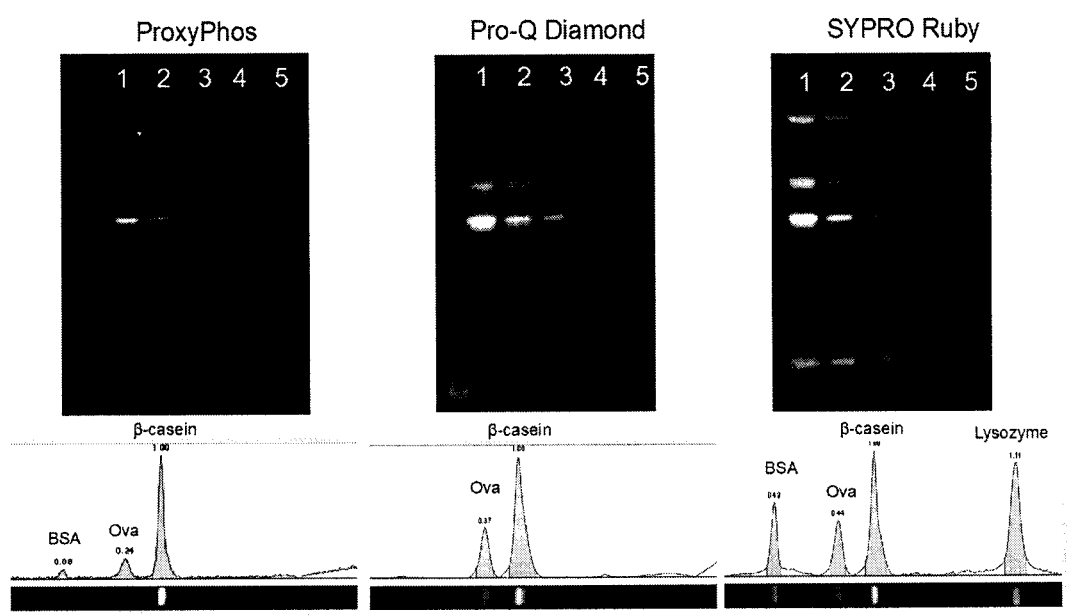
Figure 52:
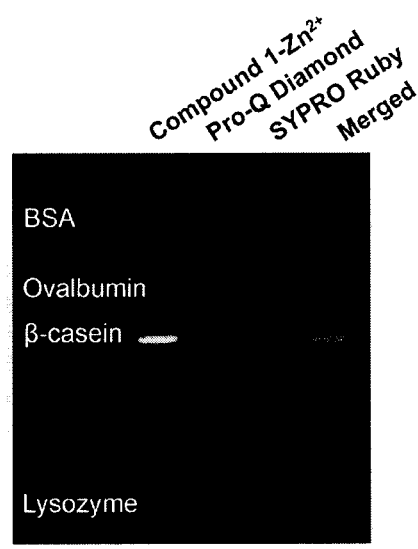
Figure 53:
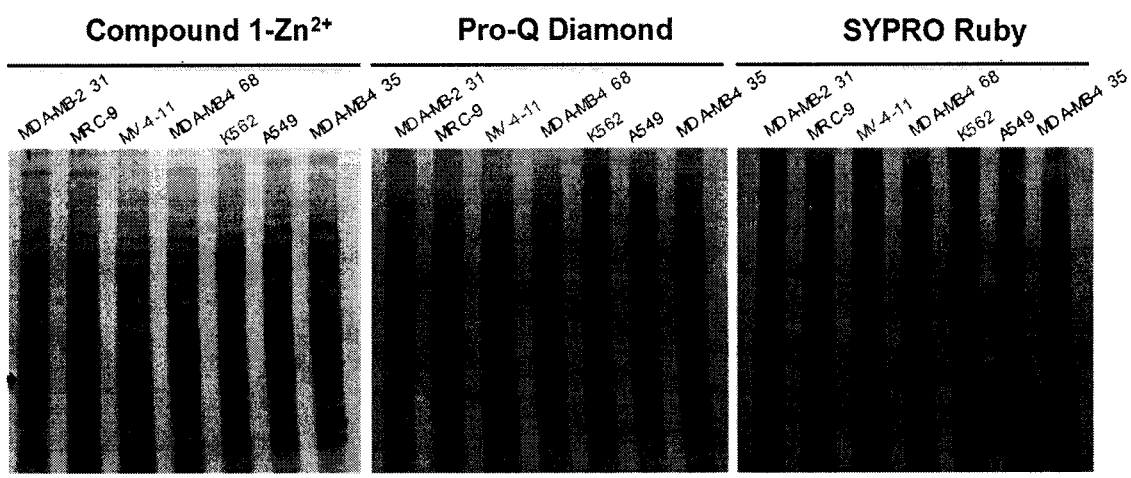
Figure 54:
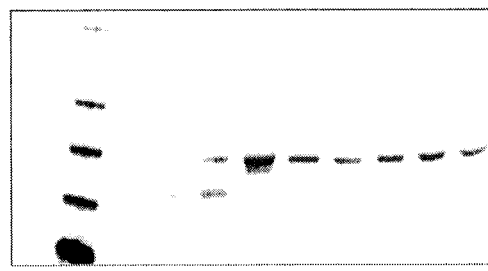
Figure 55:
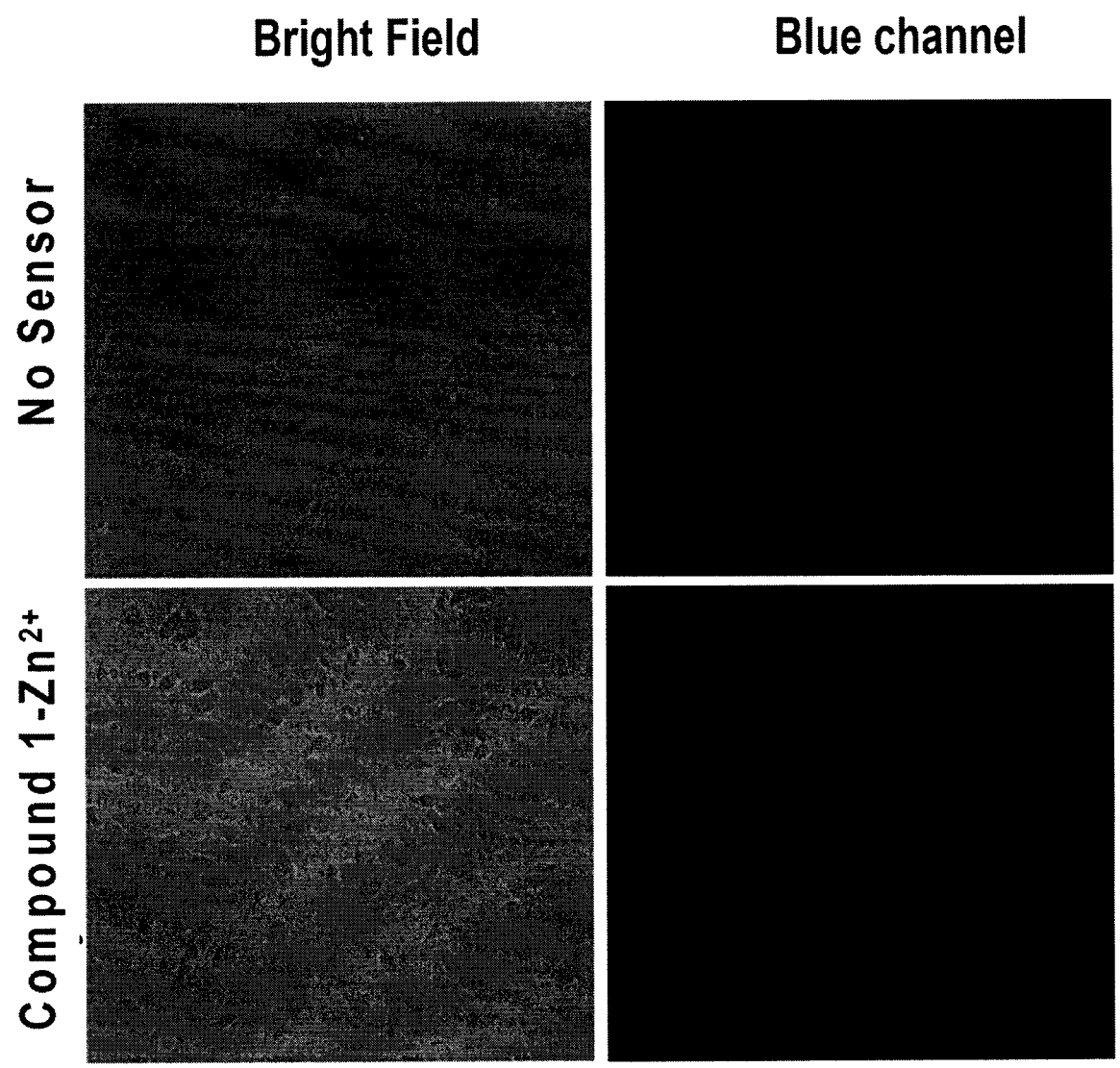
Figure 56:
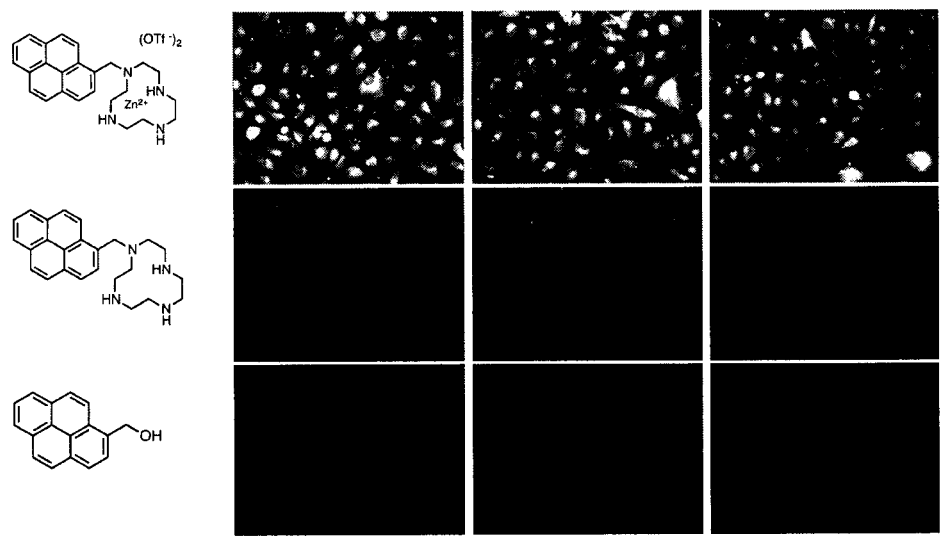
Figure 57:
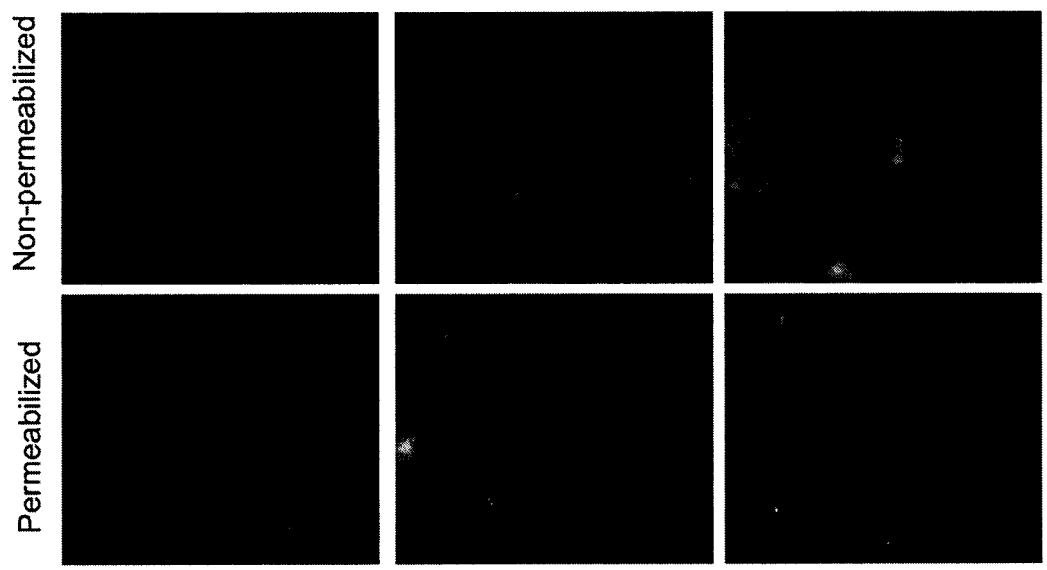
Figure 58:
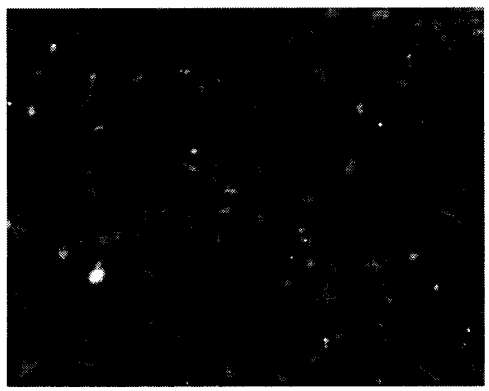
Figure 58:
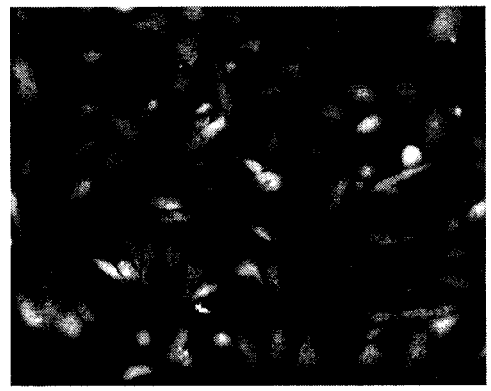
Figure 59:
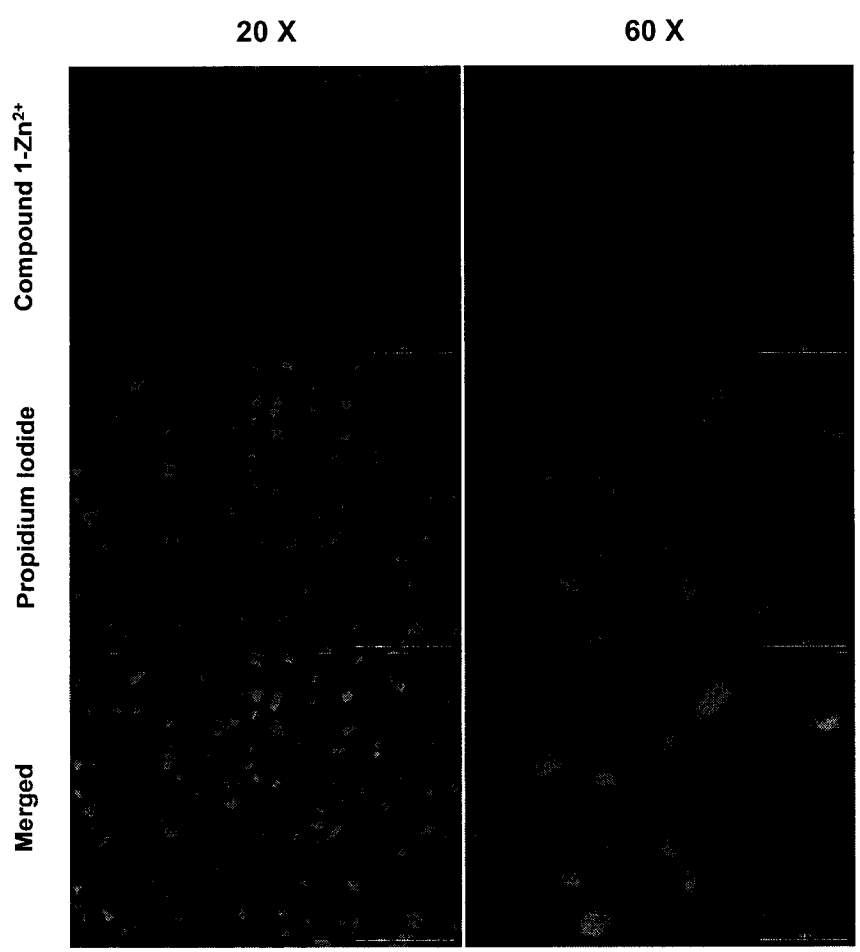
Figure 60:
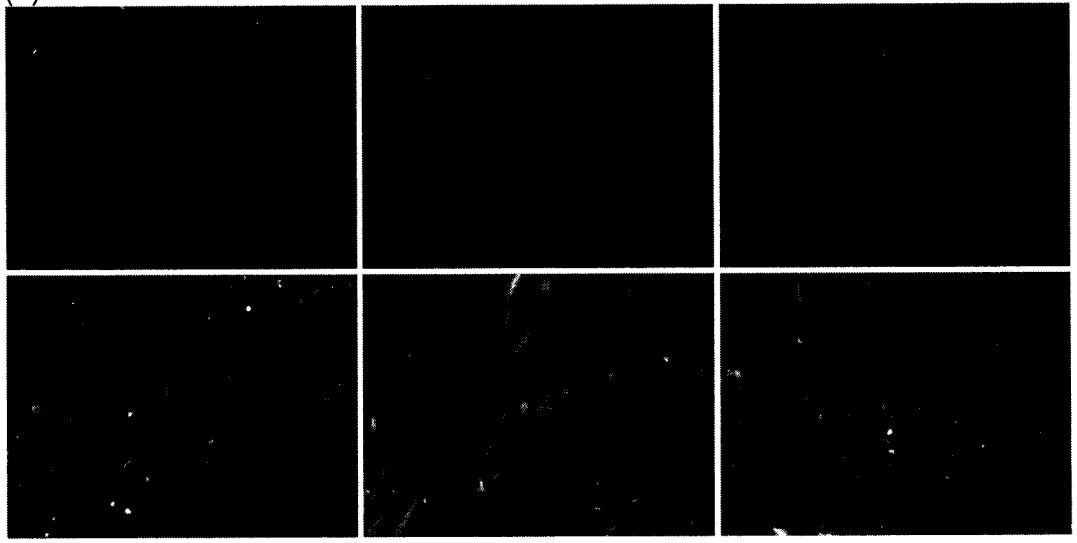
Figure 60:
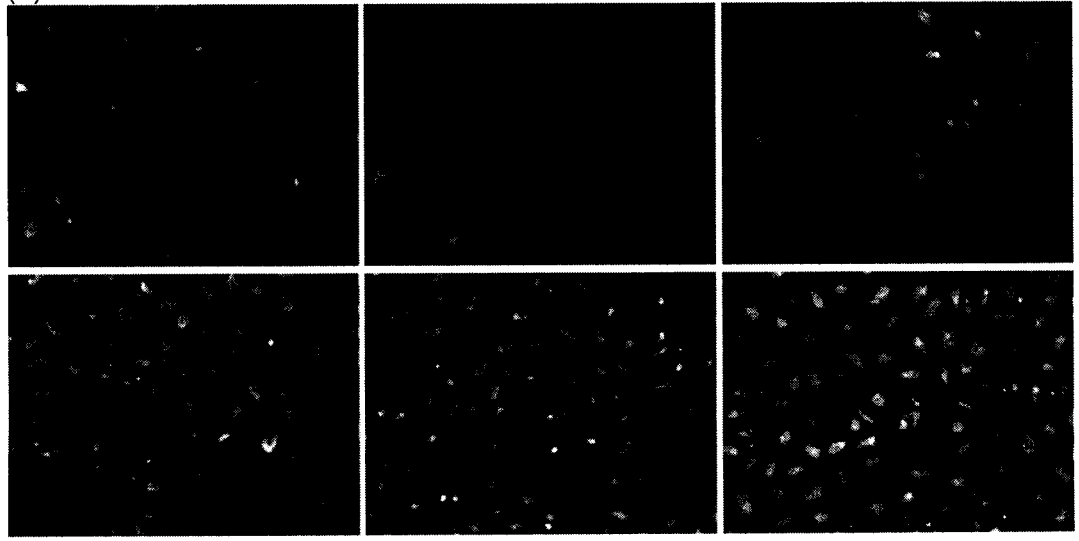
Figure 61:
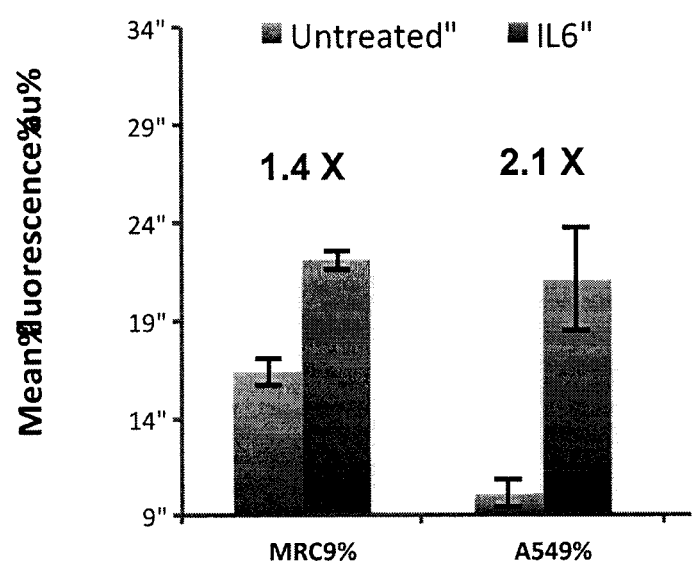
Figure 62:
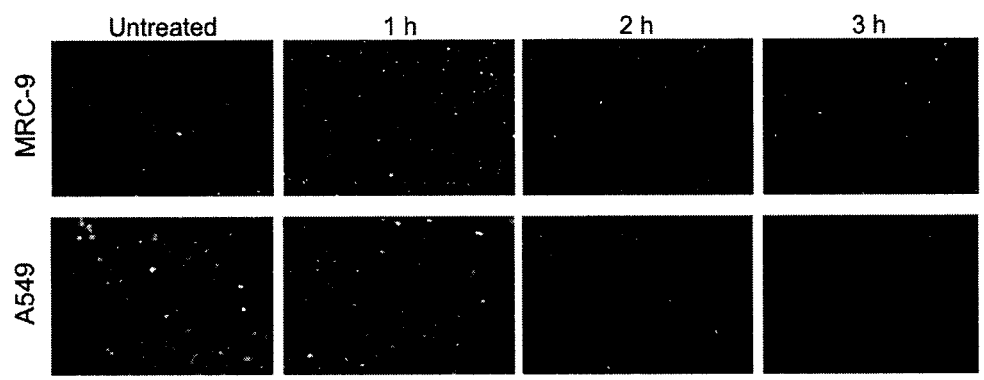
Figure 63:
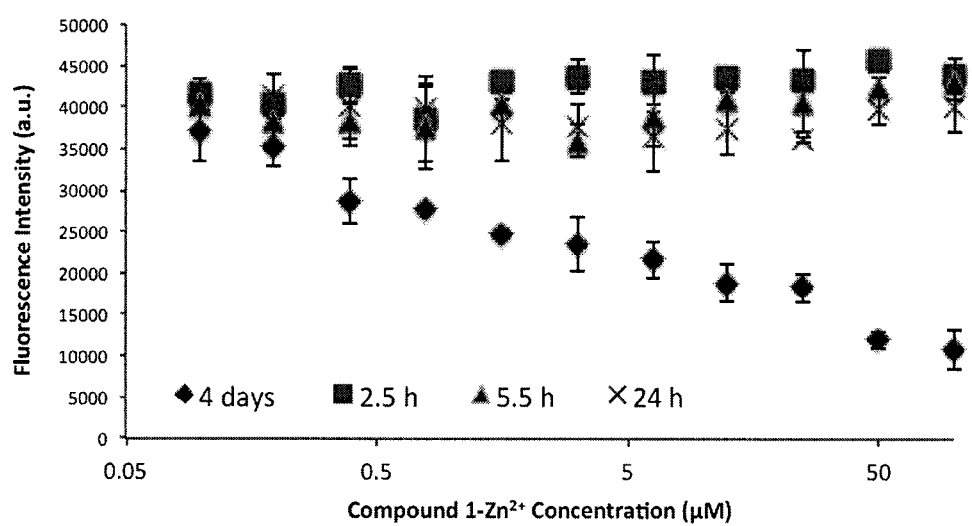
Figure 64:
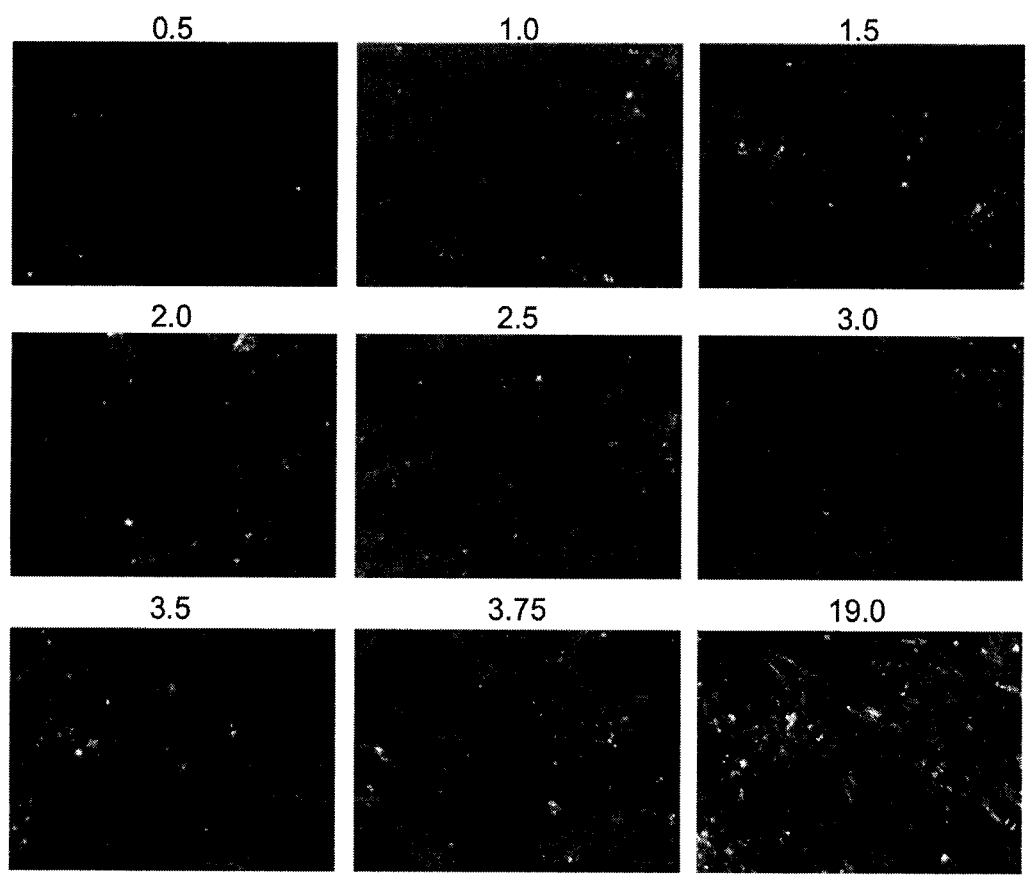
Figure 65:
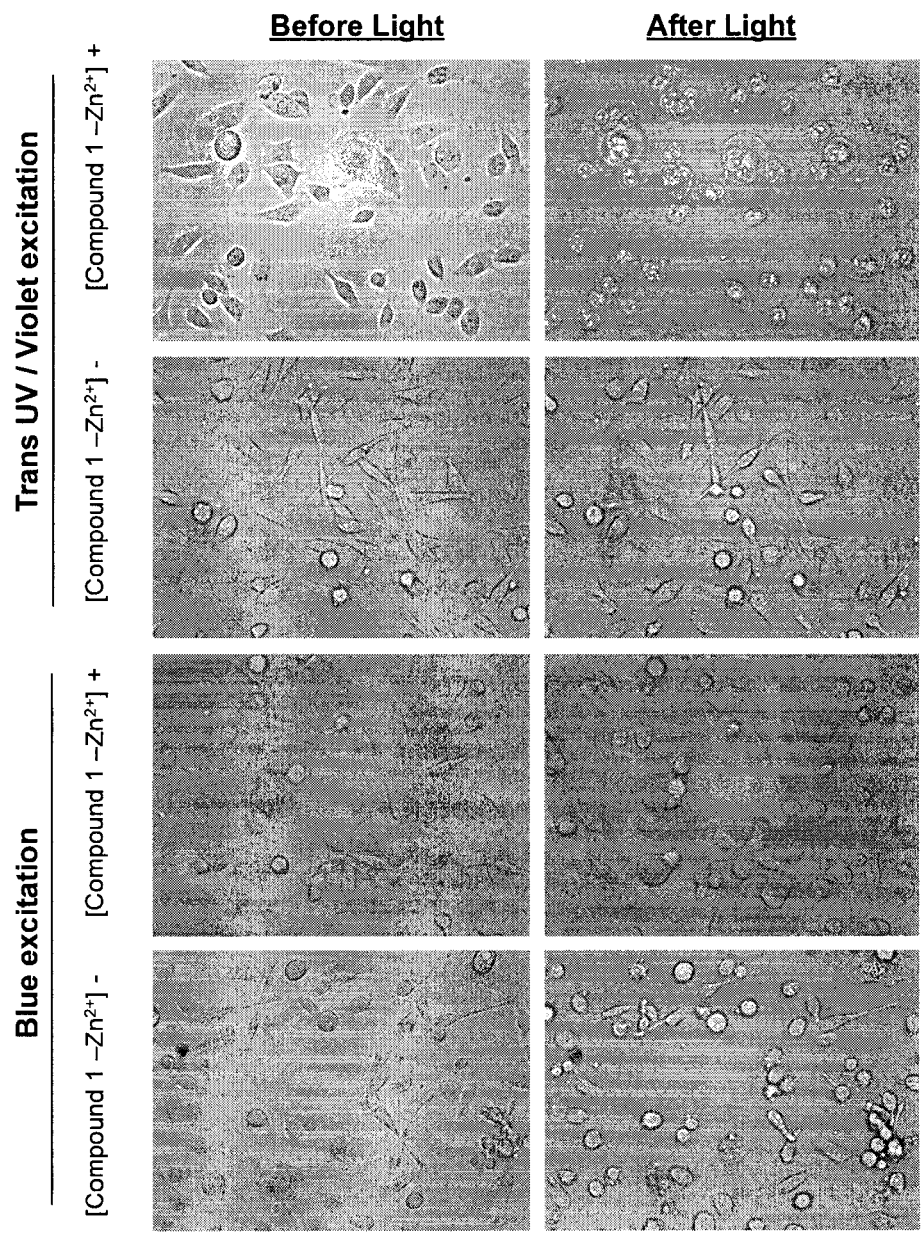
Figure 66:
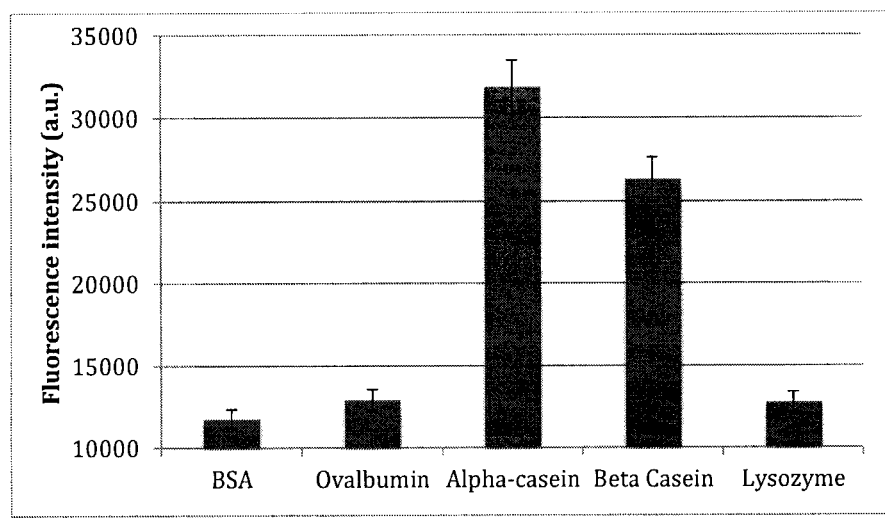

FIG. 20 shows titration of a binding solution in one embodiment of the disclosure with varying concentrations of pYpY and pY peptides; fluorescence emission was acquired using a fluorescence scan with 2 nm steps from 410-430 nm or by measuring fluorescence intensity at 420 nm using 20 nm bandwidth;

FIG. 21 shows titration of a binding solution in one embodiment of the disclosure with varying concentrations of pYpY and pY peptides using variable time-resolved settings;

FIG. 22 shows titration of a binding solution in one embodiment of the disclosure with varying concentrations of pYpY and pY peptides using (left panel) variable integration time and (right panel) variable bandwidth for acquisition of fluorescence emission;

FIG. 23 shows fluorescence emission spectra of the monomer and excimer regions of a binding solution in one embodiment of the disclosure with varying concentrations of pYpY and pY peptides;

FIG. 24 shows titration of a binding solution in one embodiment of the disclosure with varying concentrations of pYpY and pY peptides;

FIG. 25 shows titration of a binding solution in one embodiment of the disclosure with varying concentrations of small phospho-anions, calculated using (left) fluorescence enhancement factor and (right) Δ fluorescence intensity formula;

FIG. 26 shows titration of a binding solution in one embodiment of the disclosure with varying concentrations of small phospho-anions, calculated using (left) fluorescence enhancement factor and (right) Δ fluorescence intensity formula;

FIG. 27 shows titration of a binding solution in one embodiment of the disclosure with varying concentrations of the proximally phosphorylated positive control proteins (alpha casein, beta casein, D-alpha-casein), and negative control proteins (distally phosphorylated ovalbumin, and non-phosphorylated lysozyme and BSA);

FIG. 28 shows titration of a binding solution in one embodiment of the disclosure with varying concentrations of the proximally phosphorylated positive control proteins (alpha casein, beta casein, D-alpha-casein), and negative control proteins (distally phosphorylated ovalbumin, and non-phosphorylated lysozyme and BSA);

FIG. 29 shows titration of a binding solution in one embodiment of the disclosure with varying concentrations of the proximally phosphorylated positive control proteins (alpha casein, beta casein, D-alpha-casein), and negative control proteins (distally phosphorylated ovalbumin, and non-phosphorylated lysozyme and BSA);

FIG. 30 shows titration of a binding solution in one embodiment of the disclosure with varying concentrations of the proximally phosphorylated positive control proteins (alpha casein, beta casein, D-alpha-casein), and negative control proteins (distally phosphorylated ovalbumin, and non-phosphorylated lysozyme and BSA);

FIG. 31 shows a bar graph of fluorescence intensity of the excimer region of a binding solution in one embodiment of the disclosure with 10 μM of the proximally phosphorylated positive control proteins (alpha casein, beta casein, D-alpha-casein), and negative control proteins (distally phosphorylated ovalbumin, and non-phosphorylated lysozyme and BSA) with and without treatment with phosphatase;

FIG. 32 shows fluorescent image of a polyacrylamide gel stained with a binding solution in one embodiment of the disclosure, and the corresponding lane analysis. Lanes 1, 2, 3, and 4 contain 1.0, 0.5, 0.25 and 0.125 μg of each of the four proteins. Proteins included in each lane are (top to bottom) BSA, ovalbumin, β-casein and lysozyme. Proximally phosphorylated protein β-casein results in the strongest signal;

FIG. 33 shows fluorescent image of a single polyacrylamide gel sequentially stained with a binding solution in one embodiment of the disclosure, Pro-Q Diamond and SYPRO Ruby stains. Each protein was loaded in the amount of 1 μg;

FIG. 34 shows fluorescent image of a single polyacrylamide gel sequentially stained with a binding solution in one embodiment of the disclosure, Pro-Q Diamond and SYPRO Ruby stains. The amount of each protein loaded per lane is labeled in μg;

FIG. 35 shows fluorescent image of a single polyacrylamide gel sequentially stained with a binding solution in one embodiment of the disclosure, Pro-Q Diamond and SYPRO Ruby stains. The amount of each protein loaded per lane is 0.5 μg of protein. Each stain is color-coded and merged lane provides a color-map of the phosphorylation status of a protein (i.e. proximally phosphorylated, distally phosphorylated and non-phosphorylated appear in different colors);

FIG. 36 shows fluorescent image of a single polyacrylamide gel sequentially stained with a binding solution in one embodiment of the disclosure, Pro-Q Diamond and SYPRO Ruby stains, and their lane analyses. The amount of each protein loaded per lane is 1, 0.5, 0.25 and 0.125 μg (left to right). Proteins included in each lane are (top to bottom) BSA, ovalbumin, β-casein and lysozyme;

FIG. 37 shows fluorescent image of polyacrylamide gels stained with a binding solution in one embodiment of the disclosure and de-stained for variable time intervals. The amount of each protein loaded per lane is 1, 0.5, 0.25 and 0.125 µg (left to right). Proteins included in each lane are (top to bottom) BSA, ovalbumin, β-casein and lysozyme;

FIG. 38 shows lane analysis of the fluorescent image of polyacrylamide gels stained with a binding solution in one embodiment of the disclosure and de-stained for variable time intervals. The analysis was performed on the lane containing 1 µg of protein;

FIG. 39 shows lane analysis of the fluorescent image of polyacrylamide gels sequentially stained with a binding solution in one embodiment of the disclosure and SYPRO Ruby stain. The analysis was performed on the lane containing 1 µg of protein;

FIG. 40 shows fluorescent image of polyacrylamide gels stained with a binding solution in one embodiment of the disclosure and de-stained for variable time intervals. The amount of each protein loaded per lane is 1, 0.5, 0.25 and 0.125 µg (left to right). Proteins included in each lane are (top to bottom) BSA, ovalbumin, β-casein and lysozyme;

FIG. 41 shows lane analysis of the fluorescent image of polyacrylamide gels stained with a binding solution in one embodiment of the disclosure and de-stained for variable time intervals. The analysis was performed on the lane containing 1 µg of protein;

FIG. 42 shows fluorescent image of polyacrylamide gels stained with a binding solution in one embodiment of the disclosure and de-stained for variable time intervals. The amount of each protein loaded per lane is 1, 0.5, 0.25 and 0.125 µg (left to right). Proteins included in each lane are (top to bottom) BSA, ovalbumin, β-casein and lysozyme;

FIG. 43 shows lane analysis of the fluorescent image of polyacrylamide gels stained with a binding solution in one embodiment of the disclosure and de-stained for variable time intervals. The analysis was performed on the lane containing 1 µg of protein;

FIG. 44 shows lane analysis of the fluorescent image of polyacrylamide gels sequentially stained with a binding solution in one embodiment of the disclosure and SYPRO Ruby stain. The analysis was performed on the lane containing 1 µg of protein;

FIG. 45 shows fluorescent images of polyacrylamide gels stained with a binding solution in one embodiment of the disclosure and de-stained for variable time intervals. The amount of each protein loaded per lane is 1, 0.5, 0.25 and 0.125 µg (left to right). Proteins included in each lane are (top to bottom) BSA, ovalbumin, β-casein and lysozyme;

FIG. 46 shows lane analysis of the fluorescent image of polyacrylamide gels stained with a binding solution in one embodiment of the disclosure, and de-stained for variable time intervals. The analysis was performed on the lane containing 1 µg of protein;

FIG. 47 shows titration of a compound of the Formula I with variable concentration of a metal ion salt at different pH;

FIG. 48 shows titration of a compound of the Formula I with variable concentration of a metal ion salt at different pH;

FIG. 49 shows fluorescent images of the same polyacrylamide gel sequentially stained with a binding solution in one embodiment of the disclosure, Pro-Q Diamond and SYPRO Ruby stains. Each of the 7 lanes contains 40 µg of cell lysate obtained from different cell lines;

FIG. 50 shows fluorescent images of a PVDF membrane stained with a binding solution in one embodiment of the disclosure. The amount of proteins loaded per lane is shown in ng;

FIG. 51 shows fluorescent images of a single PVDF membrane sequentially stained with a binding solution in one embodiment of the disclosure, Pro-Q Diamond and SYPRO Ruby. The amount of proteins loaded per lane is 1, 0.5, 0.25, 0.125 and 0.063 µg;

FIG. 52 shows fluorescent image of a single PVDF membrane sequentially stained with a binding solution in one embodiment of the disclosure, Pro-Q Diamond and SYPRO Ruby stains. Each stain is color-coded and merged lane provides a color-map of the phosphorylation status of a protein (i.e. proximally phosphorylated, distally phosphorylated and non-phosphorylated appear in different colors);

FIG. 53 shows fluorescent images of the same PVDF membrane sequentially stained with a binding solution in one embodiment of the disclosure, Pro-Q Diamond and SYPRO Ruby stains. Each of the 7 lanes contains 40 µg of cell lysate obtained from different cell lines;

FIG. 54 shows fluorescent images of the western blot analysis for β-actin protein on the PVDF membrane which was first sequentially stained with a binding solution in one embodiment of the disclosure, Pro-Q Diamond and SYPRO Ruby stains. Each of the 7 lanes contains 40 µg of cell lysate obtained from different cell lines;

FIG. 55 shows fluorescent images acquired using fluorescence microscopy of fixed cells which were either treated or not treated with a binding solution in one embodiment of the disclosure;

FIG. 56 shows fluorescent images acquired using fluorescence microscopy of fixed cells which were treated with a binding solution in one embodiment of the disclosure, it's non-metallated derivative and a derivative lacking metal-coordinating moiety;

FIG. 57 shows fluorescent images acquired using fluorescence microscopy of fixed cells which were treated with a binding solution in one embodiment of the disclosure, with or without prior permeabilization;

FIG. 58 shows fluorescent images acquired using fluorescence microscopy of fixed cells which were treated with a binding solution in one embodiment of the disclosure, with or without pre-treatment with RNase enzyme;

FIG. 59 shows fluorescent images acquired using fluorescence microscopy of fixed cells which were co-stained with a binding solution in one embodiment of the disclosure and a nuclear stain propidium iodide;

FIG. 60 shows fluorescent images acquired using fluorescence microscopy of fixed (a) MRC-9 and (b) A549 cells which were treated with a binding solution in one embodiment of the disclosure, with or without pre-treatment with Interleukin-6;

FIG. 61 shows a bar graph which demonstrates quantification of the change in fluorescence intensity of fixed cells which were treated with a binding solution in one embodiment of the disclosure, with or without pre-treatment with Interleukin-6;

FIG. 62 shows fluorescent images acquired using fluorescence microscopy of fixed cells which were treated with a binding solution in one embodiment of the disclosure, with or without pre-treatment with staurosporine;

FIG. 63 shows time-dependent cytotoxicity of a binding solution in one embodiment of the disclosure;

FIG. 64 shows fluorescent images acquired using fluorescence microscopy of live cells, which were treated with a binding solution in one embodiment of the disclosure for variable time intervals;

FIG. 65 shows images of live cells acquired using bright field microscopy before and after excitation with laser, which were treated with a binding solution in one embodiment of the disclosure; and FIG. 66 is a graph demonstrating selective detection of proximally phosphorylated proteins using a binding solution of the disclosure in a solid support assay.

DESCRIPTION OF VARIOUS EMBODIMENTS (I) Definitions

The term "excimer forming fluorophore" as used herein refers to a moiety which upon interacting, overlapping or otherwise associating with a second excimer forming fluorophore results in an increase in fluorescence emission at a longer wavelength and a decrease of monomer emission at a shorter wavelength as compared to the unbound fluorophore.

The term "$C_{1-n}$alkyl" as used herein means straight or branched chain, saturated alkyl groups containing from one to n carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl radical.

The term "$C_{2-n}$alkenyl" as used herein means straight or branched chain, unsaturated alkyl groups containing from two to n carbon atoms and one to three double bonds, and includes (depending on the identity of n) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable n is an integer representing the largest number of carbon atoms in the alkenyl radical.

The term "$C_{2-n}$alkynyl" as used herein means straight or branched chain, unsaturated alkyl groups containing from two to n carbon atoms and one to three triple bonds, and includes (depending on the identity of n) ethynyl, propynyl, 2-methylprop-1-ynyl, but-1-ynyl, but-2-ynyl, but-3-ynyl, 3-methylbut-1-ynyl, 2-methylpent-1-ynyl, 4-methylpent-1-ynyl, 4-methylpent-2-ynyl, 4-methylpent-2-ynyl, penta-1,3-diynyl, hexyn-1-yl and the like, where the variable n is an integer representing the largest number of carbon atoms in the alkynyl radical.

The term "cycloalkyl" as used herein refers to an aliphatic ring system having 3 to "n" carbon atoms including (depending on the identity of n), but not limited to, cyclopropyl, cyclopentyl, cyclohexyl, and the like, where the variable n is an integer representing the largest number of carbon atoms in the cycloalkyl radical.

The term "bicyclic or polycyclic aryl moiety" as used herein refers to a bicyclic or polycyclic conjugated substituted or unsubstituted carbocyclic ring system having two or more rings including, but not limited to, naphthyl, tetrahydronaphthyl, phenanthrenyl, biphenylenyl, indanyl, indenyl, pyrenyl, peryleneyl, tetraceneyl and the like. Non-conjugated or unsaturated rings may also be fused to the conjugated ring system.

The term "bicyclic or polycyclic heteroaryl moiety" as used herein refers to a bicyclic or polycyclic conjugated substituted or unsubstituted carbocyclic ring system having two or more rings containing, of which one or more, for example 1-8, suitably 1-6, more suitably 1-5, and more suitably 1-4, of the atoms are a heteromoiety selected from O, S, NH, $NC_{1-6}$alkyl, and $C(=O)$, with the remaining atoms being C or CH, said ring system. Examples of heteroaryl moieties, include, but are not limited to substituted carbazoles (9-phenyl-9H-carbazole), 1H-benzo[de]isoquinoline-1,3(2H)-dione, anthra[2,1,9-def:6,5,10-d'e'f']diisoquinoline-1,3,8,10(2H,9H)-tetraone and the like. Non-conjugated or unsaturated rings may also be fused to the conjugated ring system.

The term "$C_{6-n}$aryl" as used herein means a monocyclic, bicyclic or tricyclic carbocyclic ring system containing from 6 to n carbon atoms and at least one aromatic ring and includes, depending on the identity of n, phenyl, naphthyl, anthracenyl, 1,2-dihydronaphthyl, 1,2,3,4-tetrahydronaphthyl, fluorenyl, indanyl, indenyl and the like, where the variable n is an integer representing the largest number of carbon atoms in the aryl radical.

The term "heteroaryl" as used herein means a monocyclic, bicyclic or tricyclic ring system containing from 5 to 14 atoms of which one or more, for example 1-8, suitably, 1-6, more suitably 1-5, and more suitably 1-4, of the atoms are a heteromoiety selected from O, S, NH and $NC_{1-6}$alkyl, with the remaining atoms being C or CH, said ring system containing at least one aromatic ring. Examples of heteroaryl groups, include, but are not limited to thienyl, imidazolyl, pyridyl, oxazolyl, indolyl, furanyl, benzothienyl, benzofuranyl and the like.

The suffix "ene" added on to any of the above groups means that the group is divalent, i.e. inserted between two other groups. When the group is a ring system, the two other groups may be located at any location on the ring system, including at adjacent and non-adjacent nodes.

The term "oxo-substituted" as used herein refers to a carbonyl group ($C=O$) generally replacing a $CH_2$ moiety.

The term "halo" as used herein means halogen and includes chlorine, bromine, iodine and fluorine.

The term "linker moiety" as used herein refers to a carbon-based moiety which connects the excimer forming fluorophore with the metal ion coordinating moiety. The linker moiety may be straight-chained, branched, or cyclic, or a combination of all three, and connects one or more metal ion coordinating moieties with the excimer forming fluorophore. The linker moiety optionally contains carbonyl, nitrogen and/or other heteroatom functionalities.

The term "metal ion coordinating moiety" as used herein refers to a moiety which coordinates with a metal ion, for example, a transition metal ion, a lanthanide metal ion or a post-transition metal ion and comprises one or more cyclic or acyclic organic ligands which can coordinate to a metal ion center, for example, amino, amido, carboxyl or hydroxyl groups.

The term "metal ion" as used herein refers to the positively charged forms or cations of metals.

The term "post-transition metal ion" as used herein refers to metal ions in Groups IIIB, IVB, VB, and VIB in the periodic table of the elements, and includes, but is not limited to, aluminum, gallium, germanium, indium, tin, antimony etc.

The term "lanthanide metal ion" as used herein refers to the metal ions with the atomic number from 57 to 71 in the periodic table of the elements, and includes, but is not limited to, terbium, europium, ytterbium etc.

The term "binding solution" as used herein refers to an aqueous solution containing a compound of the Formula (I)

and a suitable metal ion, which optionally forms compounds of the Formula Ia in solution.

The term carboxyl as used herein refers to a group of the formula COOH or COO⁻.

The term "hydroxyl" as used herein refers to a group of the formula OH.

The term "amino" as used herein refers to an unsubstituted amino radical or a primary, secondary or tertiary amino moiety substituted by alkyl or aryl groups. The term amino also includes unsaturated amino groups such as imines, or aromatic amine such as pyridine.

The term "polypeptide" as used herein means a polymer of amino acids and does not refer to any particular length of polymer. Such term also includes genetically expressed peptides, post-translationally modified polypeptides or proteins (e.g., glycosylated, acetylated, phosphorylated, etc.), synthetic peptides, such as short synthetic peptides, crude synthetic peptides, purified synthetic peptides. The term "polypeptide" also encompasses the term "protein".

The term "phosphorylation" as used herein refers to the addition of a phosphate group to a biological or organic molecule including macromolecules, including, but not limited to proteins, polypeptides, including all amino acids, DNA, RNA, sugars etc.

The term "proximal" as used herein refers to the spacing between phosphorylation sites on polypeptides, nucleic acids or small phospho-anions such as pyrophosphate, such that the sites are sufficiently close to allow a bound excimer containing fluorophore compound at one site to interact, overlap or otherwise associate with a bound excimer-forming fluorophore on the other site. In an embodiment, the term refers to a specific number of amino acids, such as between 1-10 amino acids, optionally 1-4 amino acids between the two sites. The term also refers to the spatial proximity of phosphorylation sites after three-dimensional folding of the polypeptide or other biomolecule. For example, phosphorylation sites that are significantly distant from each other along a polypeptide chain become spatially proximal to each other upon three-dimensional folding and may be between 2 and 100 Angstroms, optionally 3 and 50 Angstroms or suitably 5 and 30 Angstroms.

The term "control" as used herein refers to a sample that has a particular level of proximal phosphorylation. An unphosphorylated, distally phosphorylated or monophosphorylated control contains no proximal phosphorylation and would be a negative control. Alternatively, a control may contain a known amount of proximal phosphorylation and would be a positive control. The control can also be a predetermined standard.

The term "subject" as used herein refers to any member of the animal kingdom. In one embodiment, the subject is a mammal, such as a human.

(II) Excimer Forming Compounds

The present application describes a turn-on dual emission fluorescent sensor which selectively detects proximally phosphorylated sites including those found on proteins, pyrophosphates and RNA, in aqueous solutions, polyacrylamide gels, PVDF membranes, immobilized on solid supports (e.g. polymers, antibody), fixed cells and live cells.

In one embodiment, the turn-on fluorescent sensor is an excimer forming compound, in which the sensor is comprised of an excimer forming fluorophore. When two or more of the excimer forming fluorophores overlap, the fluorescence intensity of the fluorophores decreases at a shorter wavelength and fluorescence intensity increases at a longer wavelength, indicating the presence of at least two spatially proximal sites of phosphorylation.

Accordingly, in one embodiment, the disclosure provides a compound of the Formula I

(I)

wherein,
W is an excimer forming fluorophore;
V is a linker moiety;
Y is a metal ion chelate moiety; and
n is 1, 2 or 3.

In another embodiment, the disclosure provides an excimer forming compound of the Formula Ia

(Ia)

wherein,
W is an excimer forming fluorophore;
V is a linker moiety;
Y is a metal ion chelate moiety containing a metal ion; and
n is 1, 2 or 3.

In one embodiment, the present disclosure also includes a composition comprising a compound of the Formula (I) and a suitable metal ion.

In a further embodiment, the present disclosure also includes an aqueous composition comprising a compound of the Formula (I) and a suitable metal ion.

In one embodiment, the present disclosure includes a binding solution, comprising:
(a) an excimer-forming Compound of the Formula I, and
(b) a suitable metal ion, and
optionally, other additives such as salts, buffers or other organic components.

In another embodiment, the present disclosure includes a binding solution Ia, comprising:
(a) an excimer-forming compound of the Formula Ia, and
optionally, other additives such as salts, buffers or other organic components.

In one embodiment, the excimer forming fluorophore is an optionally substituted bicyclic or polycyclic aryl or heteroaryl moiety, wherein the optional substituents are selected from halo, $C_{1-20}$-alkyl, $C_{2-20}$-alkenyl, $C_{2-20}$-alkynyl, $C_{6-14}$-aryl, and $C_{5-14}$-heteroaryl.

In another embodiment, the excimer forming fluorophore is optionally substituted $C_{10-40}$-aryl or optionally substituted $C_{9-40}$-heteroaryl, wherein the optional substituents are selected from halo, $C_{1-20}$-alkyl, $C_{2-20}$-alkenyl, $C_{2-20}$-alkynyl, $C_{6-14}$-aryl, and $C_{5-14}$-heteroaryl. In another embodiment, the excimer forming fluorophore is optionally substituted $C_{10-20}$-aryl or optionally substituted $C_{9-20}$-heteroaryl, wherein the optional substituents are selected from halo, $C_{1-20}$-alkyl, $C_{2-20}$-alkenyl, $C_{2-20}$-alkynyl, $C_{6-14}$-aryl, and $C_{5-14}$-heteroaryl In one embodiment of the disclosure, the excimer forming fluorophore is an optionally substituted moiety shown below with any suitable point of attachment

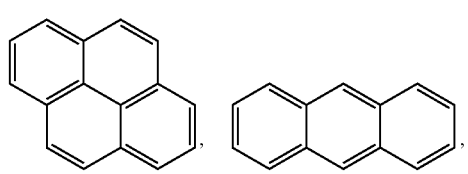

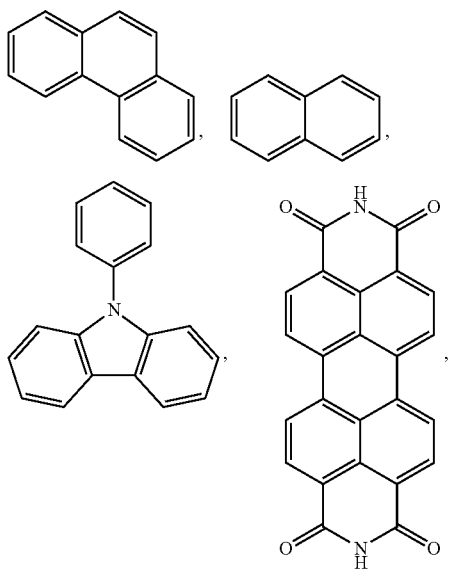

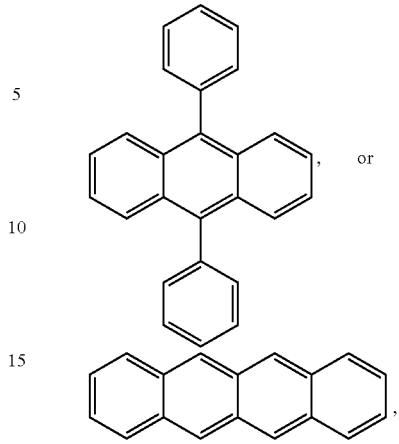

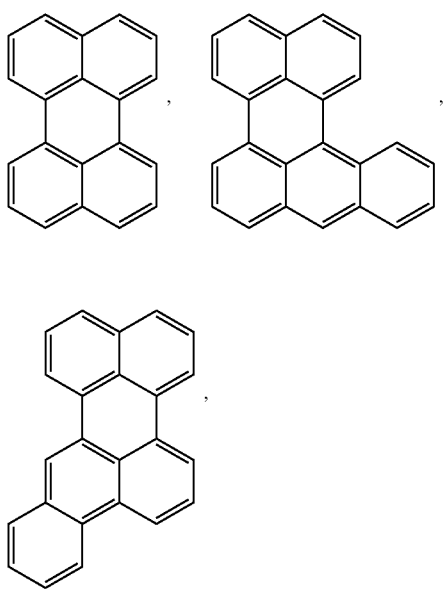

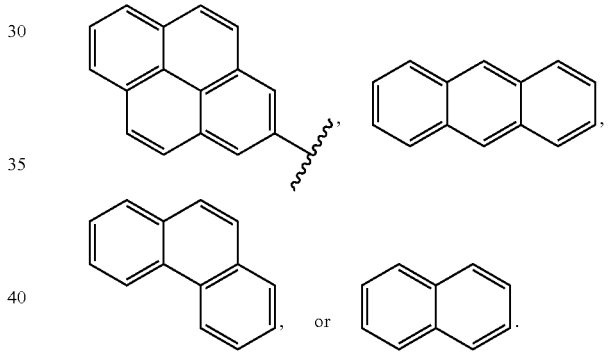

wherein the optional substituents are selected from halo, carboxy, hydroxyl, $C_{1-20}$-alkyl, $C_{2-20}$-alkenyl, $C_{2-20}$-alkynyl, $C_{3-20}$cycloalkyl, $C_{1-20}$alkoxy, —NR'R" $C_{6-14}$-aryl, and $C_{5-14}$-heteroaryl, wherein R' and R" are simultaneously or independently H or $C_{1-6}$alkyl.

In another embodiment, the excimer forming fluorophore is optionally substituted or unsubstituted

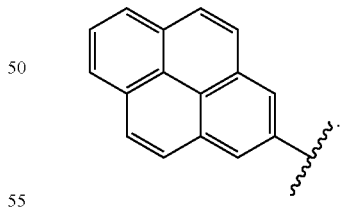

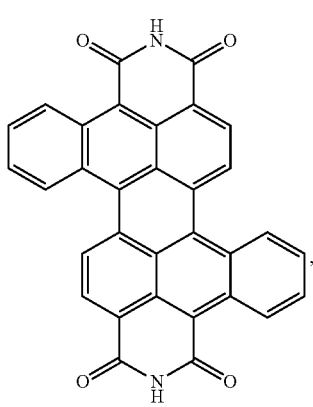

In another embodiment, the excimer forming fluorophore is optionally substituted or unsubstituted In another embodiment of the disclosure, the linker moiety is
  i) $C_{1-40}$-alkylene, $C_{2-40}$-alkenylene, $C_{2-40}$-alkynylene, or $C_{3-20}$-cycloalkyl, each of which is optionally oxo-substituted (=O) 1-6 times, optionally 1-3 times, and in which 1-3 carbon atoms are optionally replaced with a heteroatom selected from N, O, S or Si;
  ii) $C_{6-10}$-aryl, or $C_{5-10}$-heteroaryl, each of which is optionally substituted with 1-4 R groups, wherein
    R is simultaneously or independently $C_{1-20}$-alkylene, $C_{2-20}$-alkenylene or $C_{2-20}$-alkynylene, each of which is optionally oxo-substituted (=O) between 1-3 times, and in which 1-3 carbon atoms are optionally replaced with a heteroatom selected from N, O, S or Si.

In one embodiment, the linker moiety has the following structure with any suitable point of attachment

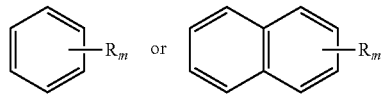

wherein,
R is as defined above;
m is 1, 2, 3 or 4,
and wherein 1-4 of the carbon atoms in the phenyl or naphthyl rings are optionally replaced with nitrogen atoms.

In a further embodiment, the linker moiety is $C_{1-20}$-alkylene, $C_{2-20}$-alkenylene, $C_{2-20}$-alkynylene, or $C_{3-10}$-cyclo each of which is optionally oxo-substituted (=O) 1-3 times, and in which 1-3 carbon atoms are optionally replaced with a heteroatom selected from N, O, S or Si.

In one embodiment, linker moiety is $C_{1-10}$-alkylene, which is optionally oxo-substituted (=O) 1-3 times, and in which 1-3 carbon atoms are optionally replaced with a heteroatom selected from N, O, S or Si. In another embodiment, the linker moiety is $C_{1-6}$-alkylene, which is optionally oxo-substituted (=O) 1-3 times, and in which 1-3 carbon atoms are optionally replaced with a heteroatom selected from N, O, S or Si.

In another embodiment, the linker moiety is methylene, butylene,

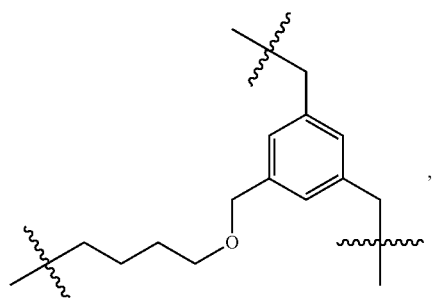

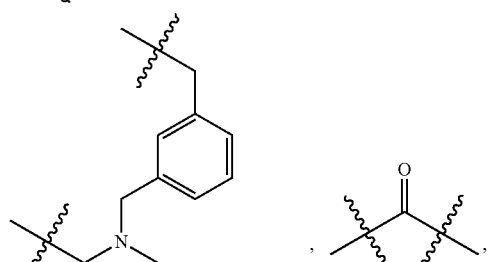

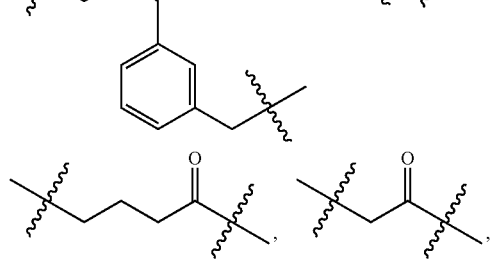

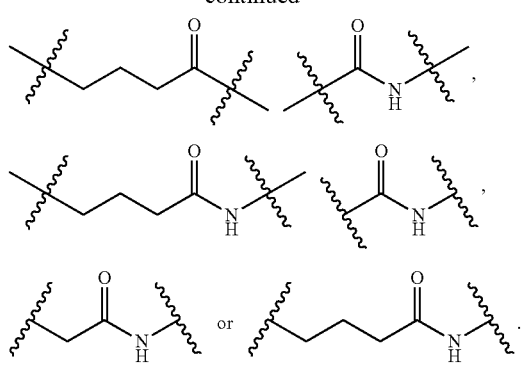

In one embodiment, the linker moiety is methylene.
In another embodiment, the linker moiety is

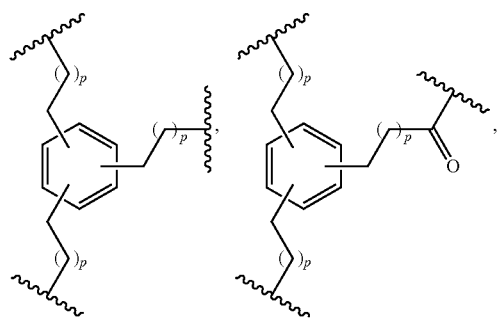

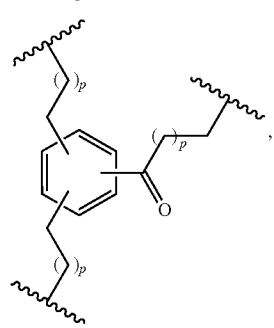

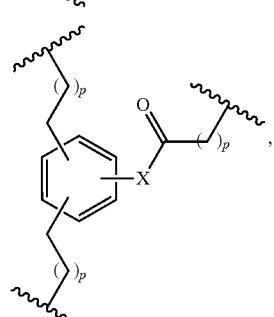

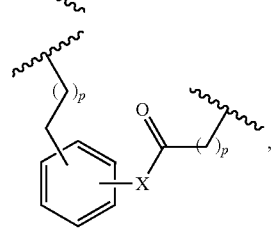

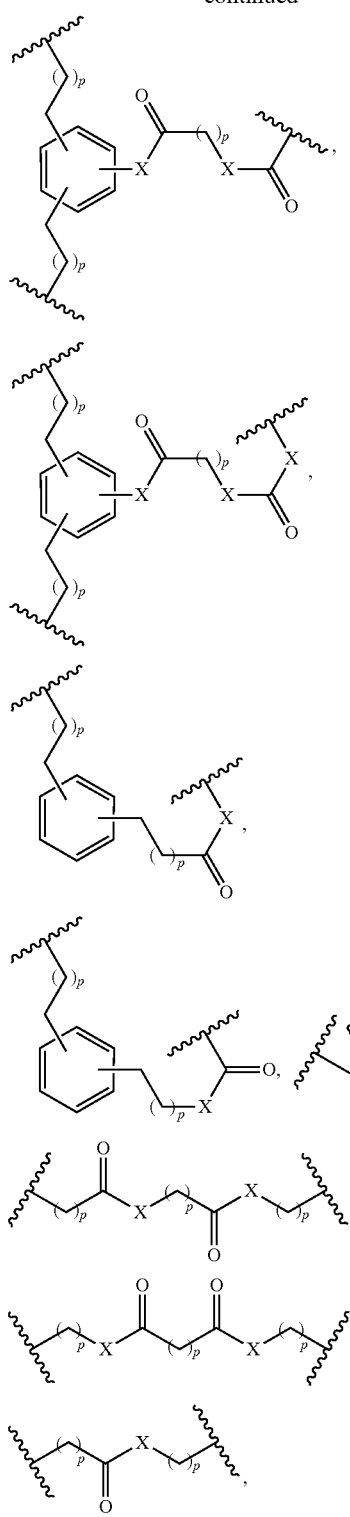

indicates the attachment to W or Y.

In another embodiment of the disclosure, the metal ion coordinating moiety is a multi-dentate moiety comprising amino, carboxyl, hydroxyl, amide, or ether groups, or other heteroatom containing moieties, wherein the heteroatom is O, S, or N.

In one embodiment, the metal ion coordinating moiety is a tri- or tetra-dentate amino group. In one embodiment, the tetra-dentate amino group is optionally substituted with any suitable point of attachment

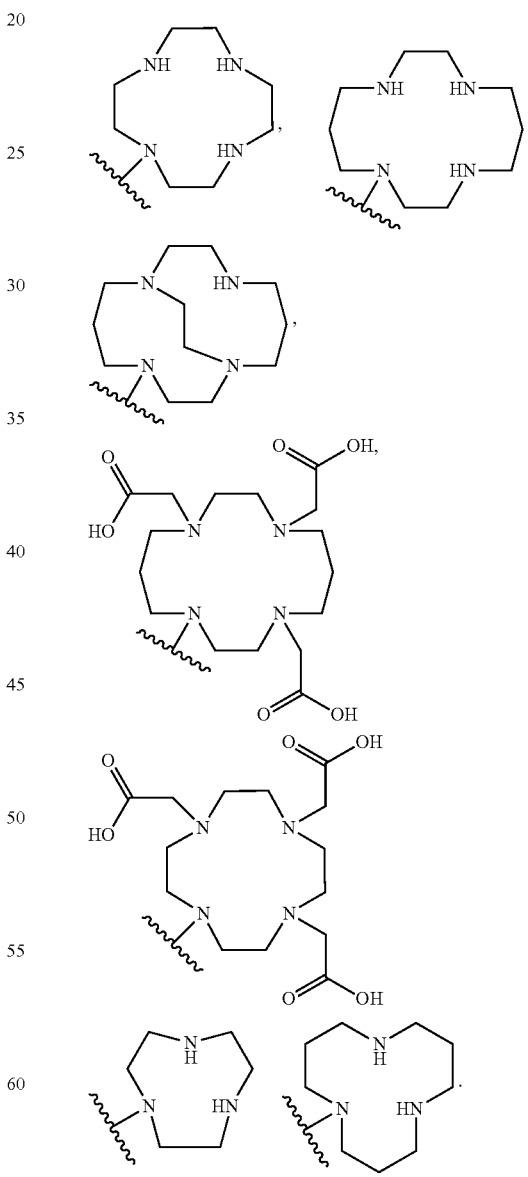

wherein X is a heteroatom selected from O, S, Si, or NH and p is an integer from 1-20, wherein the alkylene groups are further optionally oxo-substituted (=O) 1-3 times, and in which 1-3 carbon atoms are further optionally replaced with a heteroatom selected from N, O, S or Si, and wherein 1-4 of the carbon atoms in the phenyl or naphthyl rings are optionally replaced with nitrogen atoms, and where In another embodiment, the metal ion coordinating moiety is

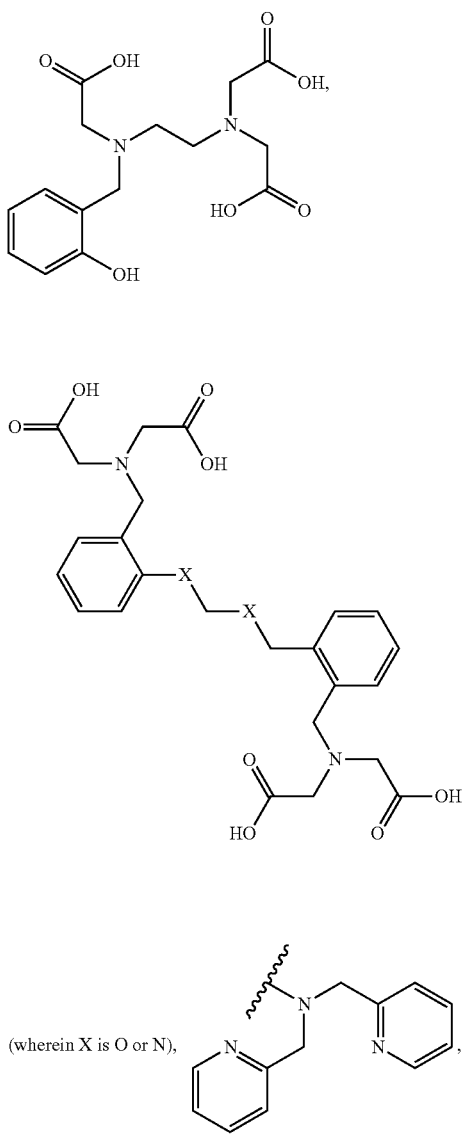
(wherein X is O or N),
or
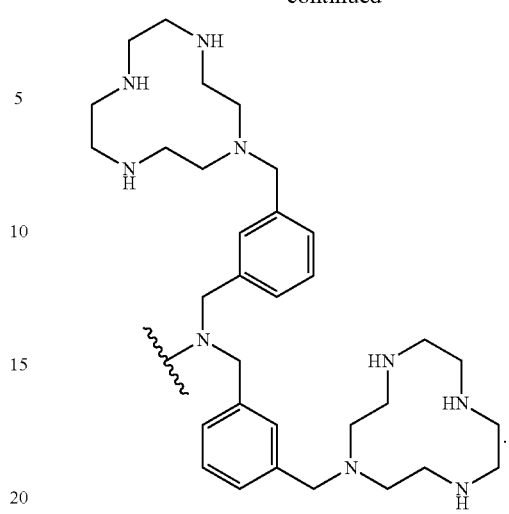
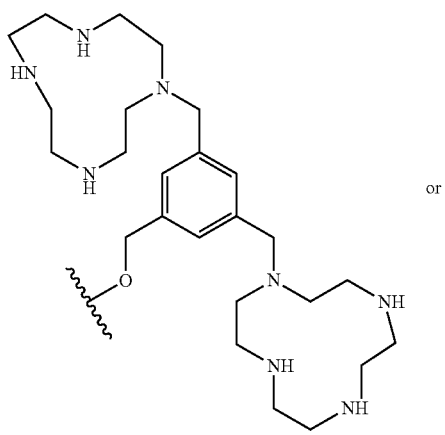
In another embodiment, the metal ion coordinating moiety is
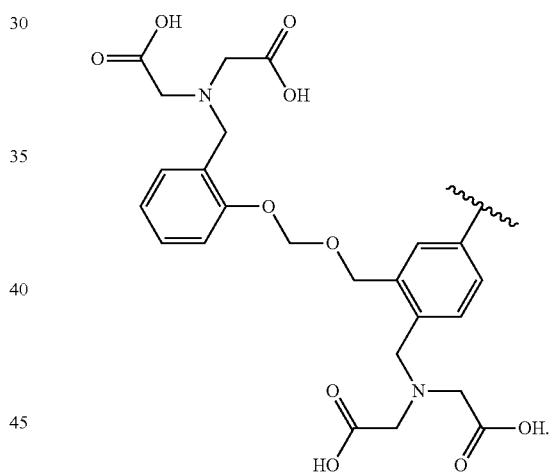
In one embodiment of the disclosure, the excimer forming compound of the Formula I is
compound 1
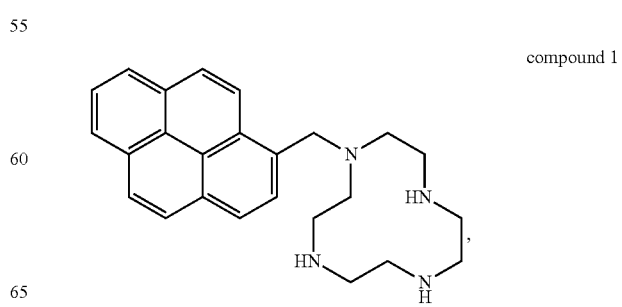

compound 2
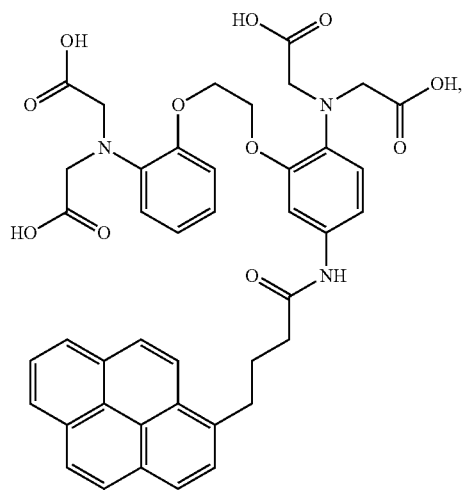
compound 3
compound 4
compound 5
compound 6
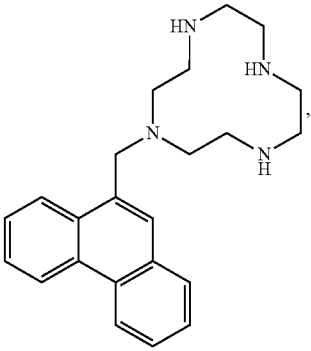
compound 7
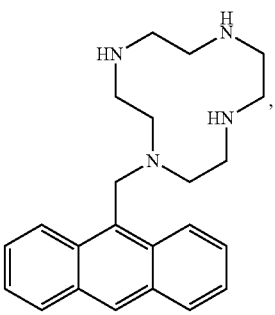
compound 8
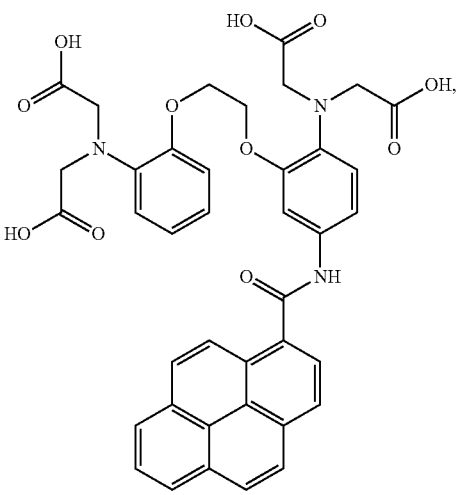
compound 9
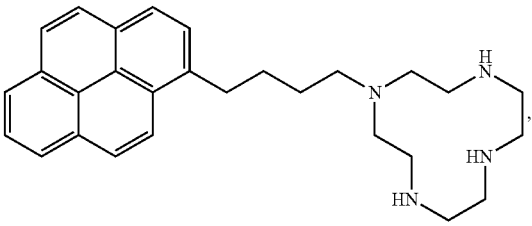

compound 10
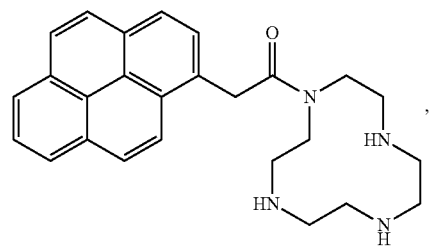

compound 11
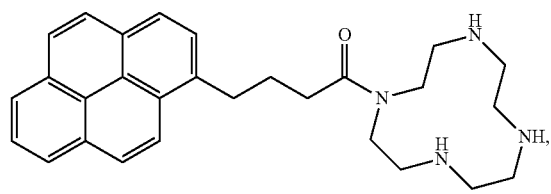

compound 12
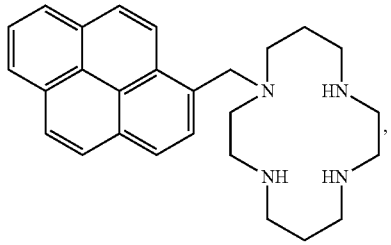

compound 13
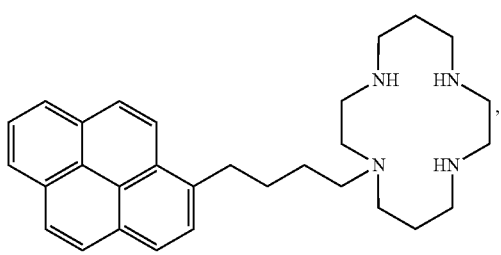

compound 14
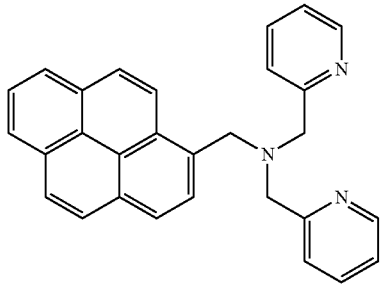

compound 15
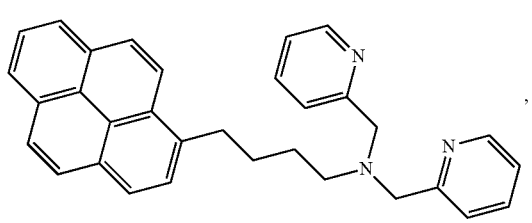

compound 16
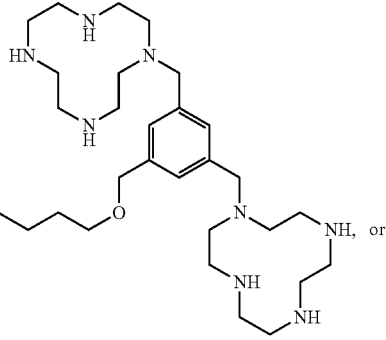

, or compound 17
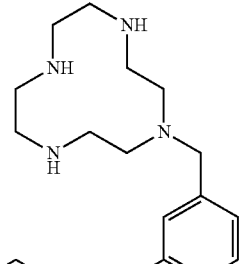

.

In another embodiment, the excimer forming compounds of the Formula I further comprise a metal ion coordinated to the metal ion coordinating moiety to optionally form compounds of the Formula Ia in solution. In one embodiment, the metal ion is any suitable metal ion which coordinates, or otherwise interacts (i.e. through hydrogen bonding, ionic bonding, dipole interactions, metal-ligand interactions etc.) with the metal ion coordinating moiety, and which simultaneously binds to a phosphorylated moiety (on a protein, peptide, enzyme, nucleic acid etc.) or pyrophosphate. In one embodiment, the metal ion is a transition metal ion, a lanthanide metal ion or post-transition metal ion. In one embodiment, the transition metal ion is Zn(II), Cu(II), Mn(II), Ni(II), Fe(II), Cd(II) Al(III), Fe(III). In one embodiment the post-transition metal ion is Al(III) or Ga(III). In one embodiment, the lanthanide metal ion is Tb(III), Eu(III), YB(III). In one embodiment, the suitable metal ions are in the form of salts, such as any metal ion salt, for example, zinc(II) trifluoromethanesulfonate, gallium(III) chloride or terbium(III) chloride.

In one embodiment, the compounds of the Formula Ia are formed in situ, for example by preparing a binding solution of a compound of the Formula I with a suitable metal ion to form in solution compounds of the Formula Ia. In one embodiment, the binding solution comprises (i) a compound of the Formula I; and (ii) a suitable metal ion, for example in the form of a salt. In one embodiment, the components of the binding solution are kept separate until ready for use.

The present disclosure also includes a kit, comprising:
(i) a compound of the Formula (I);
(ii) a suitable metal ion, for example in the form of a salt; and
(iii) instructions for use.

(III) Methods

The excimer forming compounds of the Formula I and Ia of the present disclosure and binding solutions and compositions of the disclosure are useful for detecting proximally phosphorylated polypeptide residues, and other proximally phosphorylated molecules. Such detection is useful for a variety of applications, including without limitation, detecting and quantifying proximally phosphorylated proteins in protein expression and purification; assessing activation status of proteins that are activated by proximal phosphorylation; monitoring de-phosphorylation rate and progress of proximally phosphorylated protein sites; comparing the abundance of proximally phosphorylated proteins in protein extracts of various cells lines and samples; detecting diseases in which abundance of proximal phosphorylation is increased; and detecting pyrophosphates.

In one embodiment, excimer formation is accompanied by a decrease in monomer-region fluorescence and the extent of excimer formation can be detected and quantified by measuring the decrease in monomer fluorescence. Likewise, excimer formation is accompanied by an increase in fluorescence at the excimer-forming region of a fluorophore and the extent of excimer formation can be detected and quantified by measuring the increase in fluorescence. In one embodiment, ratios of the decrease in monomer-region fluorescence and the increase in fluorescence at the excimer-forming region can be calculated to detect and quantify changes at both regions.

In one embodiment, the methods of the disclosure are performed by measuring fluorescence intensity in the excimer and/or monomer regions. In another embodiment, analysis of the fluorescence is performed using fluorescence polarization, as the tertiary complex between a proximally phosphorylated target and two excimer units limits the tumbling rate of the excimer fluorophore and increase fluorescence polarization and anisotropy values.

Accordingly, in one embodiment, the present disclosure provides a method of detecting proximal phosphorylation of a molecule, such as a polypeptide (or protein), comprising:
(a) contacting a sample of the molecule, such as a polypeptide sample, with a binding solution of the disclosure;
(b) detecting a fluorescence signal at a wavelength specific for the excimer forming fluorophore of a binding solution of the disclosure;
wherein detection of a signal having a fluorescence intensity greater than a signal of a sample containing a distal phosphorylation, monophosphorylation or no phosphorylation indicates that the molecule, such as the polypeptide, contains phosphorylation of at least two sites proximal to each other.

In an embodiment, the signal from a sample comprising only a monophosphorylated site is undetectable or similar to background levels or to the level of a sample containing no phosphorylation.

In one embodiment, the method is performed on a gel as a gel-based assay in which the molecule, such as a polypeptide, is separated on polyacrylamide gels and detected directly on the gel without need for excising the band(s).

In another embodiment, the present disclosure provides a method of detecting proximal phosphorylation of a polypeptide comprising:
(a) contacting a polypeptide sample with a binding solution of the disclosure;
(b) detecting a fluorescence signal at a wavelength specific for the excimer forming fluorophore of a binding solution of the disclosure;
(c) comparing the fluorescence signal of (b) with the fluorescence intensity of a distally phosphorylated, monophosphorylated or unphosphorylated control;
wherein detection of a signal having a fluorescence intensity greater than the control indicates that the polypeptide contains phosphorylation of at least two sites proximal to each other. It will be understood that the increase in fluorescence intensity depends on the protein concentration in the sample, and the concentration of the excimer forming compound in a binding solution of the disclosure, and the number of proximally phosphorylated sites. For quantification, a calibration curve is generated based on the protein of known concentration and compositions which is used to compare the fluorescence signal from the sample under investigation.

In one embodiment, the method is performed on a gel as a gel-based assay in which polypeptide is separated on polyacrylamide gels and detected directly on the gel without need for excising the band(s). In another embodiment, quantification can also be performed on the gel by comparison of the signal intensity of the bands.

In one embodiment, the amino acids that are proximally phosphorylated are sufficiently close in a native or denatured state, for example within 1-6, suitably 1-4, amino acid residues. In another embodiment, the amino acids that are proximally phosphorylated are sufficiently close when the protein is in its 3D conformation.

In a further embodiment, the present disclosure provides a method of quantifying proximal phosphorylation comprising:
(a) contacting a sample with a binding solution of the disclosure;
(b) detecting a fluorescence signal at a wavelength specific for the excimer forming fluorophore of a binding solution of the disclosure;
(c) comparing the fluorescence signal of (b) with the fluorescence intensity of control samples of known quantities of proximal phosphorylation;
wherein detection of a signal having a fluorescence intensity similar to one of the control samples indicates the amount of proximal phosphorylation in the sample. In one embodiment, the relative number of proximally phosphorylated sites can be monitored over time to determine, for example, whether in the process of a reaction (e.g. enzymatic or chemical phosphorylation or dephosphorylation of a peptide) the proximally phosphorylated sites increase or decrease over time.

In an embodiment, the polypeptide sample is a protein extract from a bacterial, yeast, insect or mammalian cell line including human cell lines.

In another embodiment, the polypeptide sample is from a subject suffering from a disease associated with increased proximal phosphorylation of proteins, such as cancer, Alzheimer's etc. In another embodiment, the polypeptide sample is a sample synthesized using a peptide synthesizer or is a sample from a genetically modified protein expressed on a vector.

In another embodiment, the present disclosure provides a method of assessing the activation status of a protein that is activated by proximal phosphorylation comprising:
(a) contacting a sample of the protein with a binding solution of the disclosure;
(b) detecting a fluorescence signal at a wavelength specific for the excimer forming fluorophore of a binding solution of the disclosure;
(c) comparing the fluorescence signal of (b) with the fluorescence intensity of an unactivated protein sample;
wherein detection of a signal having a fluorescence intensity greater than the unactivated protein sample indicates that the protein sample is activated. In an embodiment, the protein that is activated by proximal phosphorylation is an enzyme or kinase, including but not limited to Jak2 or Erk2.

In another embodiment, the present disclosure provides a method for identification of phosphatase or kinase substrates, comprising:
(a) contacting a sample of a protein (or peptide) with a binding solution of the disclosure and a phosphatase or kinase;
(b) detecting a fluorescence signal at a wavelength specific for the excimer forming fluorophore of a binding solution of the disclosure;
(c) comparing the fluorescence signal of (b) with the fluorescence intensity of a second sample which does not contain a phosphatase or kinase;
wherein detection of a decrease for the phosphatase or an increase for the kinase in the intensity of the fluorescence signal from (b) compared to the signal from (c) indicates that the protein is a substrate of the phosphatase or kinase. In one embodiment, this method can be used to determine the kinetic parameters of a kinase/phosphatase by measuring fluorescence over time.

In one embodiment, the identification and quantification of phosphatase or kinase substrates can be conducted on gels in a gel-based assay by pre-treating a peptide/protein sample with a kinase/phosphatase and then separating the sample on the gel. The gel is then treated with a binding solution of the disclosure and bands displaying signals different from the untreated control are potential substrates of the phosphatase or kinase. In one embodiment, the kinase and/or phosphatase are capable of phosphorylating or de-phosphorylating, respectively, proximal sites.

In yet another embodiment, the present disclosure provides a method of detecting pyrophosphates comprising:
(a) contacting a sample with a binding solution of the disclosure;
(b) detecting a fluorescence signal at a wavelength specific for the excimer forming fluorophore of a binding solution of the disclosure;
(c) comparing the fluorescence signal of (b) with the fluorescence intensity of a control sample;
wherein detection of a signal having a fluorescence intensity greater than the control sample indicates that the protein sample contains pyrophosphates. In one embodiment, pyrophosphates are selectively detected over ATP, ADP, AMP and Pi, wherein a ratiometric data analysis is performed, wherein a ratio of monomer excimer emission is calculated (fluorescence enhancement factor).

In a further embodiment, the present disclosure provides a method of quantifying pyrophosphates comprising:
(a) contacting a sample with a binding solution of the disclosure;
(b) detecting a fluorescence signal at a wavelength specific for the excimer forming fluorophore of a binding solution of the disclosure;
(c) comparing the fluorescence signal of (b) with the fluorescence intensity of control samples of known quantities of pyrophosphates;
wherein detection of a signal having a fluorescence intensity similar to one of the control samples indicates the amount of pyrophosphates in the sample. In one embodiment, the relative amount of pyrophosphate can be monitored over time to determine, for example, whether in the process of a reaction (e.g. enzymatic or chemical driven consumption or liberation of pyrophosphate), pyrophosphate increases or decreases over time.

In an embodiment, the sample is a bodily sample, such as urine, synovial fluid or blood, or any sample which releases or consumes PPi. In one embodiment, the sample is used in an assay for the detection and/or quantification of the release or consumption of PPi, such as an assay measuring ATP consumption, which is used to monitor enzyme activity or a PCR reaction to monitor the progress of the reaction by release of PPi.

In an embodiment, the methods disclosed herein are performed in solution, such as an aqueous buffer.

In another embodiment, the methods disclosed herein are performed in a gel, for example, a 1-D or 2-D gel. In one embodiment, the gel is run first, and then incubated in a binding solution of the disclosure. In one embodiment, the fluorescence is detected on a membrane, such as a PVDF (polyvinylidene fluoride) membrane.

In one embodiment, due to the non-covalent nature of the excimer forming compounds of the disclosure, binding solutions of the disclosure do not alter the post-translational modifications or the primary sequence of the proteins/peptides. In one embodiment therefore, on gel-based assays, a binding solution of the disclosure can be first used to stain the gel to visualize the proximally phosphorylated sites and then a binding solution of the disclosure can be washed away and the gel can be subject to many other commercially available stains or other manipulations known to a person skilled in the art. For example, in one embodiment, following staining with a binding solution of the disclosure (for the detection of proximally phosphorylated sites), the gel can be further analyzed for the total phosphorylation or any other post-translational modification. Additionally, following staining with a binding solution of the disclosure (for the detection of proximally phosphorylated sites), the gel can be also additionally analyzed for the total protein content. In one embodiment, by applying a binding solution of the disclosure in conjunction with a total phospho-protein stain on the same gel, the number of proximally phosphorylated sites as compared to total phosphorylation level per protein/peptide band can be ratiometrically assessed. In another embodiment, bands isolated from gel-based assays can be analyzed by mass spectroscopy, or by performing protein digestion (e.g. trypsin digestion) and analyzing the peptides by LC-MS/MS (liquid chromatography tandem mass spectrometry).

In another embodiment, gels and membranes stained with a binding solution of the disclosure can be visualized using trans-UV light.

In another embodiment, the methods of the disclosure can also be performed on blotting membranes, which can also include a Western blot analysis following staining of the membranes with a binding solution of the disclosuredisclosure. In one embodiment, polyvinylidene fluoride (PVDF) low fluorescence blotting membranes are compatible with a binding solution of the disclosure. In one embodiment, the gels are separated using polyacrylamide gel electrophoresis (PAGE), electro-blotted to a blotting membrane, and stained with a binding solution of the disclosure for the detection of proximally phosphorylated sites. Alternatively, a sample of interest can be DOT-blotted onto the blotting membrane using standard protocols.

In another embodiment, a binding solution of the disclosure can also be used for the detection of proximally phosphorylated sites, which are attached or immobilized by any biological or synthetic means (e.g. antibody, polymer).

In another embodiment, a binding solution of the disclosure can be used for the detection of proximally phosphorylated sites in fixed cells or live cells. For example in one embodiment, levels of intracellular RNA can be monitored due to association of the compound of a binding solution of the disclosure with the phosphate backbone. In one embodiment, a binding solution of the disclosure can be used to monitor the changes in the amount of proximally phosphorylated sites including those on proteins in response to changing cellular environment, for example assessment of effect of drugs, hormones, pollutants, or any other biological or synthetic agent (e.g. efficiency of agonists or antagonist of kinase or phosphatase pathways can be assessed).

In one embodiment, RNA and DNA can be visualized by applying a binding solution of the disclosure and detecting proximally phosphorylated sites of the phosphate backbone of these nucleic acids on agarose gels.

In another embodiment, a binding solution of the disclosure may be useful as photosensitizers of cells, for example, by inducing selective cytotoxicity.

It will be understood that the above methods can be conducted with a binding solution or kit, in which a compound of the Formula I and a suitable metal ion are contacted in situ to optionally form the compound of the Formula Ia or the binding solution. In one embodiment, the binding solution is formed before contact with a sample; for example, a binding solution comprising a compound of the Formula I and a suitable metal ion are combined in an aqueous solution to form the binding solution which is then combined with a sample to detect proximal phosphorylation. In another embodiment, the binding solution is formed after contact with a sample; for example, an aqueous solution of a sample of a compound of the Formula I is first prepared, followed by addition of a suitable metal ion to form the binding solution.

The following non-limiting examples are illustrative of the disclosure:

EXAMPLES

Materials and Methods

All reagents and solvents were purchased from Sigma-Aldrich. Silica gel chromatography was performed with Silica Gel 60 (particle size 40-63 μm) obtained from EMD. Thin layer chromatrography (TLC) plates were obtained from EMD. Peptides were purchased from CanPeptide at 95% purity. Stat5 protein was purchased from SignalChem at 95% purity. Bovine serum albumin (BSA), α-casein, β-casein and dephosphorylated α-casein (α-casein-D) were purchased from Sigma Aldrich as lyophilized powders. Pro-Q Diamond stain was purchased from Invitrogen/Molecular Probes. Criterion TGX precast 10% polyacrylamide gels were purchased from BIORAD.

All peptides were purchased from CanPeptide at 95% purity as lyophilized powder. Following abbreviations were used for peptides: YpY or pY—Ac-AYpYAA-NH$_2$, YY—Ac-AYYAA-NH$_2$, pYpY—Ac-ApYpYAA-NH$_2$, pSpS—Ac-ApSpSAA-NH$_2$, SpS or pS—Ac-ASpSAA-NH$_2$, pSApS—Ac-ApSApSAA-NH$_2$, pTAY or pT—Ac-ApTAYAA-NH$_2$, pTApY—Ac-ApTApYAA-NH$_2$, pYAApY—Ac-ApYAApYA-NH$_2$, pYAAApY—Ac-pYAAApY-NH$_2$, pYAAAApY—Ac-pYAAAApY-NH$_2$, pYAAAAApY—Ac-pYAAAAApY-NH$_2$.

Example 1

Synthesis and Characterization

Care was taken to minimize exposure of compounds to light during synthesis, storage and testing. Molecular sieves were activated by heating to 125° C. under vacuum overnight. NMR spectra were recorded on a Bruker Avance III spectrometer at 23° C., operating at 400 MHz for $^1$H NMR and 100 MHz for $^{13}$C NMR spectroscopy in either CDCl$_3$ or CD$_3$CN. Chemical shifts (δ) are reported in parts per million (ppm) referenced to residual isotopic solvent. Coupling constants (J) are reported in Hertz (Hz). High Resolution Mass Spectrometry (HRMS) was performed on an AB/Sciex QStar mass spectrometer with an ESI source, MS/MS and accurate mass capabilities, associated with an Agilent 1100 capillary LC system. Low Resolution Mass Spectrometry (LRMS) was performed on a Waters Micromass ZQ model MM1. UV-vis spectra were collected using a Hewlett Packard 8452A diode array spectrophotometer with 200 μL quartz cuvettes. Purifications by prep-HPLC were performed using Atlantis Prep T3 10 μm C18 (2) 250×19 mm column run at 20 mL/min (preparative) using gradient mixtures of water with 0.1% TFA and 10:1 acetonitrile/water with 0.1% TFA. The crude mixture was injected as a solution 4:1 0.1% TFA in water/acetonitrile. Analysis by rpHPLC was performed using a Phenomex Luna 5 μm C18 (2) 150×4.60 mm column run at 1.2 mL/min (analytical) using gradient mixtures of 0.1% TFA in water and acetonitrile. Condition (A) started with 0.1% TFA water with a gradient going to 100% acetonitrile over 30 min, followed by 5 min at 100% acetonitrile. Condition (B) started with 0.1% TFA in water with a gradient going to 100% acetonitrile over 50 min, followed by 5 min at 100% acetonitrile. All final compounds, except compound 15, were lyophilized from water/acetonitrile after purification by chromatography prior to testing. Titanic solvent was made using 92% DCM, 7% methanol and 1% ammonium hydroxide.

Example 1.1a

Tri-tert-butyl 10-(pyren-1-ylmethyl)-1,4,7,10-tetraazacyclododecane-1,4,7-tricarboxylate (1)

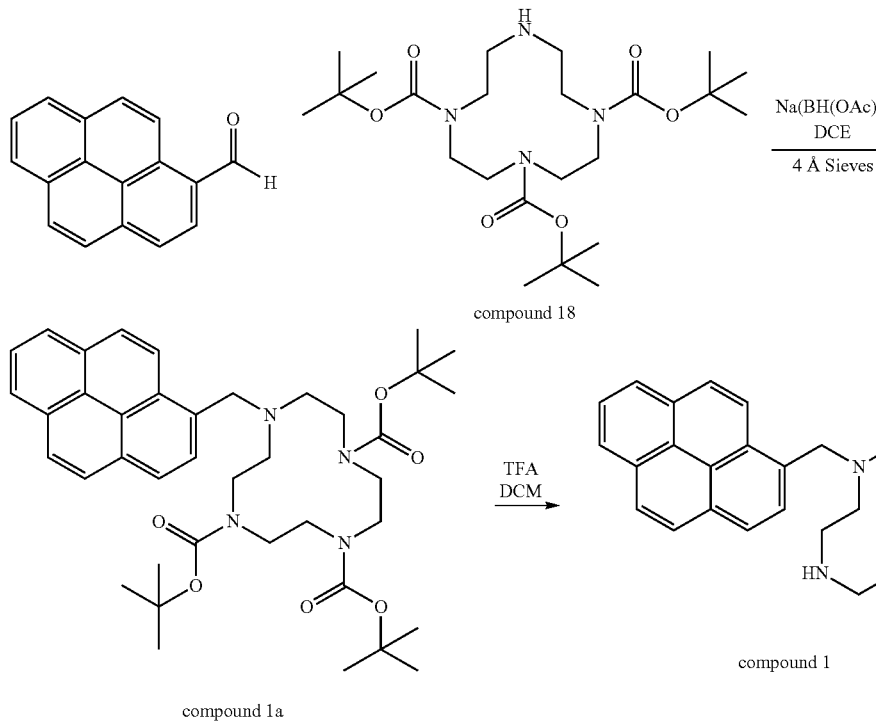

To a stirred solution of 1-pyrene aldehyde (200 mg, 0.87 mmol) in 9 mL 1,2-dichloroethane was added Boc₃Cyclen (compound 18) (410 mg, 0.87 mmol), sodium triacetoxyborohydride (552 mg, 2.60 mmol) and 5-10 4 Å molecular sieves. This reaction mixture was allowed to stir at ambient temperature over 24 h under $N_2$ atmosphere. Subsequently, the reaction mixture was extracted with 40 mL of DCM and washed 3 times with 40 mL aliquots of saturated $NaHCO_3$ $_{(aq)}$. The extract was concentrated down in vacuo. Flash column chromatography was performed (20% EtOAc in toluene) to afford a white solid (484 mg, 81%): mp 87-91° C.; $^1$H NMR (400 MHz, CD₃CN) δ 8.47-8.40 (d, J=9.4 Hz, 1H), 8.20-8.15 (d, J=7.8 Hz, 2H), 8.12-8.05 (m, 2H), 8.04-7.96 (m, 4H), 4.30 (s, 2H), 3.60-3.49 (br, 4H), 3.42-2.92 (m, 8H), 2.71-2.51 (br, 4H), 1.43 (s, 9H), 1.39-0.98 (br, 18H); $^{13}$C NMR (100 MHz, CD₃CN) δ 155.5, 155.1, 132.3, 131.1, 130.6, 130.4, 129.7, 129.1, 127.2, 127.0, 126.9, 125.9, 124.9, 124.8, 124.42, 124.35, 123.8, 78.6, 55.6, 55.1, 49.0, 47.6, 47.3, 27.8, 27.4; UV-Vis (MeOH) λ$_{max}$ 224, 258, 264, 326 nm; LRMS (ESI+) m/z calc'd for $C_{40}H_{55}N_4O_6$ [M+H]⁺ 687.41. found 687.42.

Example 1.1 b 1-(Pyren-1-methyl)-1,4,7,10-tetraazacyclododecane

To a solution of 1a (200 mg, 0.29 mmol) in 5 mL of DCM was added 5 mL of TFA with stirring. After 2 hours the reaction mixture was concentrated down in vacuo and the TFA was azeotroped off in vacuo with MeOH. The crude product was taken up in MeOH and passed through a column packed with Amberlite IRN-78, followed by evaporation of the solvent in vacuo. The crude product was then purified by preparative HPLC. The product was again passed through a column packed with Amberlite IRN-78 to afford an off white solid (108 mg, 96%): mp 65-68° C.; $^1$H NMR (400 MHz, CDCl₃) δ 8.52-8.47 (d, J=9.3 Hz, 1H), 8.18-8.14 (dd, J=7.5 Hz, 3.1 Hz, 2H), 8.13-8.10 (d, J=8.5 Hz, 2H), 8.05-7.95 (m, 4H), 4.30 (s, 2H), 2.78-2.64 (m, 14H), 2.52-2.45 (m, 5H); $^{13}$C NMR (100 MHz, CDCl₃) δ 132.3, 131.2, 130.8, 130.7, 129.7, 128.4, 127.3, 127.2, 127.0, 125.6, 125.0, 124.9, 124.80, 124.76, 124.4, 123.6, 58.4, 52.2, 47.0, 45.9, 45.2; UV-Vis (MeOH) λ$_{max}$ 210, 246, 324, 338 nm; LRMS (ESI+) m/z calc'd for $C_{25}H_{31}N_4$ [M+H]⁺ 387.25. found 387.17; HRMS (ESI+) m/z calc'd for $C_{25}H_{31}N_4$ [M+H]⁺ 387.25487. found 387.25551; rpHPLC t$_R$: condition (A) 11.474 min., condition (B) 16.637 min., purity 99.5% and 98.0% respectively.

Example 1.1c 1-(Pyren-1-methyl)-1,4,7,10-tetraazacyclododecane-zinc(II) trifluoromethanesulfonate

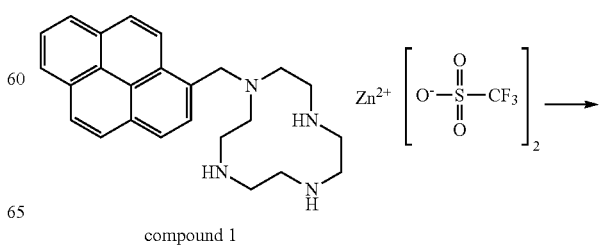

compound 1

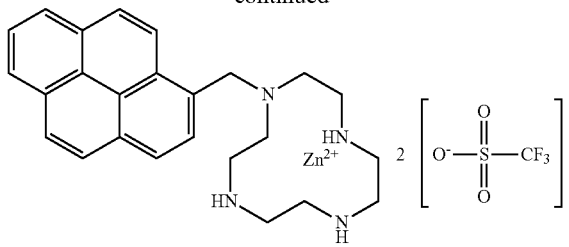

To a solution of 1 (50 mg, 0.13 mmol) in 2 mL acetonitrile was added zinc(II) trifluoromethanesulfonate (47 mg, 0.13 mmol) and allowed to stir for 0.5 h at ambient temperature. The acetonitrile was then removed in vacuo to yield the final product as a white solid (97 mg, quantitative): mp 132-137° C. (decomposed); $^1$H NMR (400 MHz, CD$_3$CN) δ 8.56-8.49 (d, J=9.2 Hz, 1H), 8.36-8.26 (m, 4H), 8.24-8.16 (m, 2H), 8.14-8.05 (m, 2H), 4.77 (s, 2H), 3.75-3.60 (br, 2H), 3.38-3.20 (m, 3H), 3.07-2.92 (m, 6H), 2.79-2.65 (m, 6H); UV-vis (MeOH) $\lambda_{max}$ 240, 266, 314, 326 nm; LRMS (ESI+) m/z calc'd for C$_{26}$H$_{30}$F$_3$N$_4$O$_3$SZn [M−OTf]$^+$ 599.13. found 599.15, m/2z calc'd for C$_{25}$H$_{30}$N$_4$Zn [M−2OTf]$^{2+}$ 225.09. found 225.13.

Example 1.2

Synthesis of Compound 2

Example 1.2a

Synthesis of Compound 2a

To a solution of 1-pyrenebutyric acid (Sigma Aldrich, cat. 257354, 52 mg, 0.18 mmol) in 3 mL DMF, TBTU (70 mg, 0.22 mmol) and DIPEA (41 μL, 0.23 mmol), compound 19 (100 mg, 0.18 mmol) was added. The reaction was stirred at room temperature for 12 h under N$_2$ atmosphere. The mixture was extracted with ethyl acetate. The extract was washed with sodium bicarbonate. This was purified by flash chromatography with ethyl acetate/hexanes to give dimethyl 2,2'-((2-(2-(2-(bis(2-methoxy-2-oxoethyl)amino)-5-(4-(pyren-1-yl)butanamido)phenoxy)ethoxy)phenyl)azanediyl) diacetate (compound 2a) as a white solid (102 mg, 73%); $^1$H NMR (400 MHz, CDCl$_3$) δ 8.25 (d, J=9.3 Hz, 1H), 8.13 (d, J=7.6 Hz, 2H), 8.08-8.02 (m, 2H), 8.01-7.92 (m, 3H), 7.81 (d, J=7.8 Hz, 1H), 7.22-7.15 (m, 1H), 7.00 (d, J=8.6 Hz, 1H), 6.93-6.78 (m, 4H), 6.75 (d, J=8.6 Hz, 1H), 4.17 (s, 4H), 4.11 (s, 4H), 4.07 (s, 4H), 3.52 (s, 12H), 3.41-3.31 (m, 2H), 2.41-2.30 (m, 2H), 2.29-2.20 (m, 2H); $^{13}$C NMR (100 MHz, CDCl$_3$) δ 171.9, 171.7, 170.8, 150.4, 150.2, 138.9, 135.6, 135.3, 133.3, 131.2, 130.7, 129.8, 128.6, 127.3, 127.24, 127.19, 126.5, 125.7, 124.9, 124.79, 124.76, 124.6, 123.2, 122.3, 121.3, 119.2, 119.0, 112.9, 112.4, 106.0, 67.2, 66.8, 53.3, 53.2, 51.5, 51.4, 36.5, 32.4, 27.0.

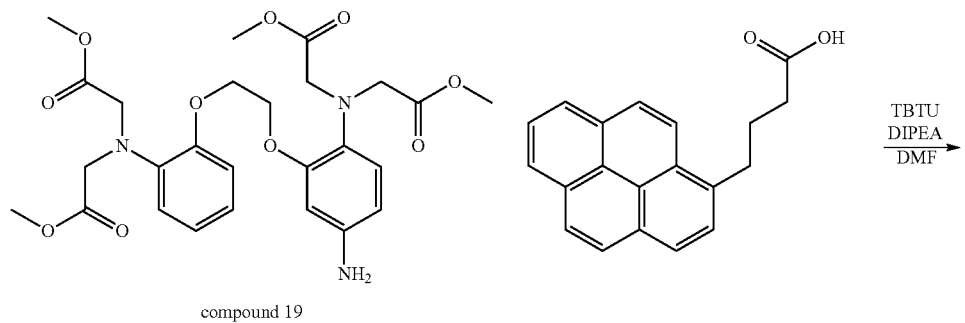

compound 19

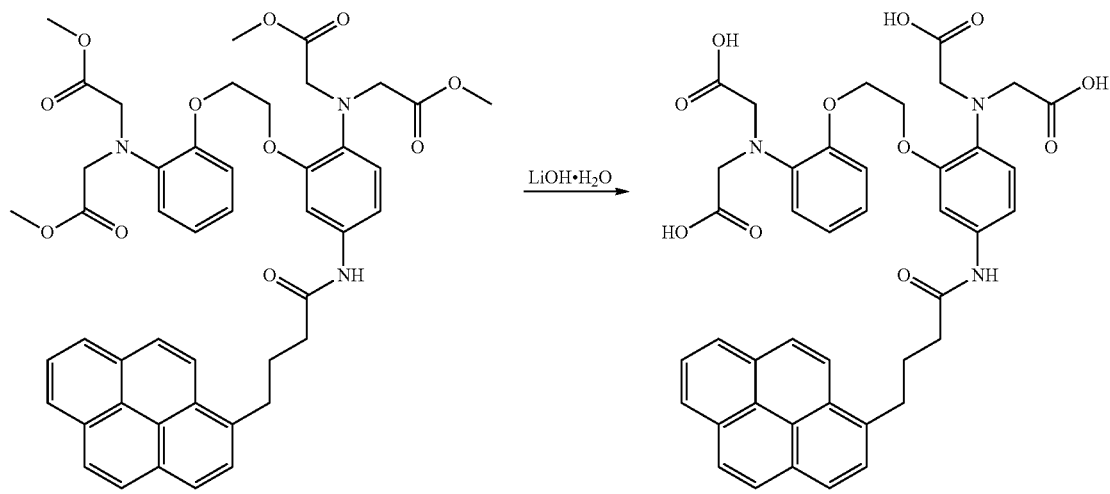

compound 2a compound 2

Example 1.2b

Synthesis of Compound 2

Compound 2a (100 mg, 0.12 mmol) was dissolved in 10 mL of a 1:1 mixture of water and THF. LiOH.H$_2$O (26 mg, 0.62 mmol) was added and the reaction mixture was allowed to stir for 2 hours. 50 mL of 1M NaOH was added the reaction mixture was washed twice with 50 mL of EtOAc. The aqueous layer was then acidified with HCl and extracted 3 times with 50 mL portions of EtOAc. The solvent was removed in vacuo to give 2,2'-((2-(2-(2-(bis(carboxymethyl)amino)-5-(4-(pyren-1-yl)butanamido)phenoxy)ethoxy)phenyl)azanediyl)diacetic acid as an off white solid (90 mg, 97%); $^1$H NMR (400 MHz, CD$_3$OD) δ 8.33 (d, J=9.0 Hz, 1H), 8.14 (d, J=7.6 Hz, 2H), 8.12-8.06 (m, 3H), 8.01-7.93 (m, 4H), 7.89 (d, J=6.7 Hz, 1H), 6.98-6.82 (m, 5H), 4.42-3.98 (m, 10H), 3.48-3.35 (m, 2H), 2.55-2.44 (m, 2H), 2.30-2.19 (m, 2H); LRMS (ESI+) m/z calc'd for C$_{42}$H$_{39}$N$_3$O$_{11}$ [M+H]$^+$ 761.26. found 762.10, [M+Na]$^+$ found 784.13; HRMS, (ESI+) m/z calc'd for C$_{42}$H$_{40}$N$_3$O$_{11}$ [M+H]$^+$ 762.2657. found 762.2663; rpHPLC t$_R$: condition (A) 20.326 min., condition (B) 30.477 min., purity 84.5% and 86.6% respectively.

Example 1.3

Synthesis of Compound 4

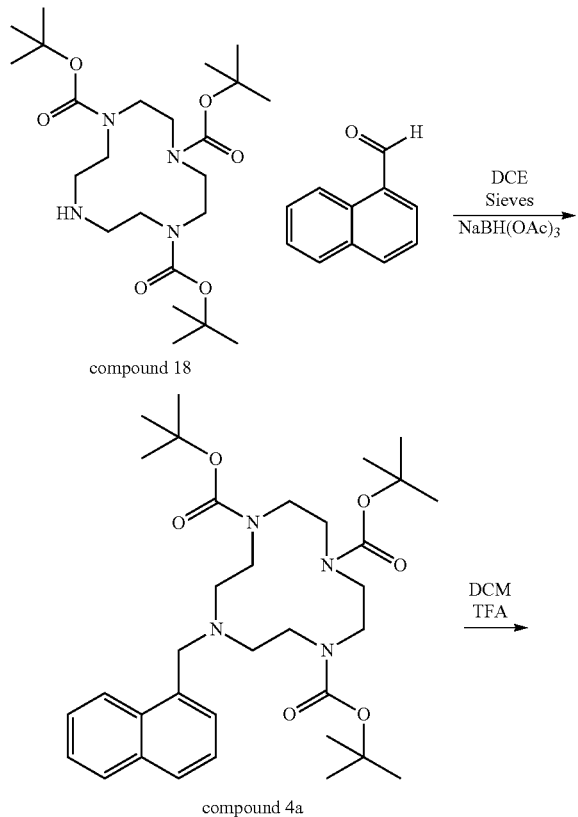

compound 18 compound 4a

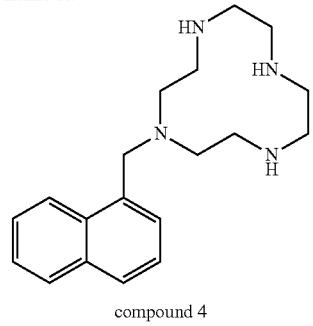

compound 4

Example 1.3a

Synthesis of Compound 4a

To a solution of compound 18 (100 mg, 0.21 mmol) in 2 mL DCE, 1-Napthaldehyde (Sigma Aldrich, cat. N109, 29 µL, 0.31 mmol) was added. To this reaction mixture, 4 Å molecular sieves were added. The reaction was left to stir for 2 h, after which sodium triacetoxyborohydride was added (66 mg, 0.31 mmol) and the reaction was allowed to stir for 24 hours. Subsequently, the mixture was purified by flash chromatography with 30% ethyl acetate/hexanes to give the tri-tert-butyl 10-(naphthalen-1-ylmethyl)-1,4,7,10-tetraazacyclododecane-1,4,7-tricarboxylate as a white solid (109 mg, 85%); $^1$H NMR (400 MHz, CDCl$_3$) δ 8.19 (d, J=6.8 Hz, 1H), 7.82 (d, J=8.3 Hz, 1H), 7.75 (d, J=8.2 Hz, 1H), 7.51-7.42 (m, 3H), 7.39 (t, J=7.5 Hz, 1H), 4.12 (s, 2H), 3.57-2.60 (m, 16H), 1.49-1.29 (m, 27H); LRMS (ESI+) m/z calc'd for C$_{34}$H$_{52}$N$_4$O$_6$ [M+H]$^+$ 612.39. found 613.39; [M+Na]$^+$ found 635.55.

Example 1.3b

Synthesis of Compound 4

To a solution of compound 4a (105 mg, 0.17 mmol) in 10 mL DCM, 5 mL TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78 to give 1-(naphthalen-1-ylmethyl)-1,4,7,10-tetraazacyclododecane as an oil (45 mg, 89%); $^1$H NMR (400 MHz, CD$_3$OD) δ 7.92 (d, J=8.5 Hz, 1H), 7.90-7.86 (m, 2H), 7.85 (s, 1H), 7.54-7.48 (m, 3H), 4.02 (s, 2H), 3.29-3.12 (m, 8H), 3.04-2.87 (m, 8H); $^{13}$C NMR (100 MHz, CD$_3$OD) δ 134.3, 132.0, 131.6, 129.0, 128.9, 128.6, 126.6, 125.8, 125.3, 122.5, 54.7, 48.8, 44.2, 42.1, 41.8; LRMS (ESI+) m/z calc'd for C$_{19}$H$_{28}$N$_4$ [M+H]$^+$ 312.23. found 313.23; HRMS, (ESI+) m/z calc'd for C$_{19}$H$_{29}$N$_4$ [M+H]$^+$ 313.2387. found 313.2380; rpHPLC t$_R$: condition (A) 8.675 min., condition (B) 11.866 min.

Example 1.4

Synthesis of Compound 5

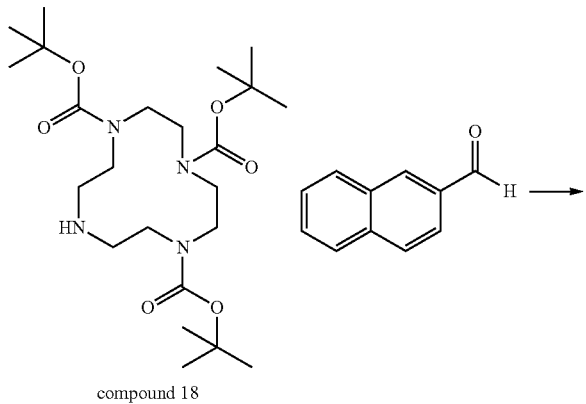

compound 18

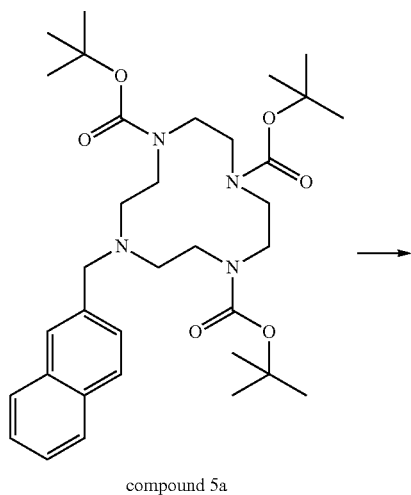

compound 5a

Example 1.4a

Synthesis of Compound 5a

To a solution of compound 18 (300 mg, 0.64 mmol) in 5 mL DCE, 2-Napthaldehyde (Sigma Aldrich, cat. N206, 112 mg, 0.72 mmol) was added. To this reaction mixture, 4 Å molecular sieves were added. The reaction was left to stir for 2 h, after which sodium triacetoxyborohydride was added (270 mg, 1.28 mmol). Subsequently, the mixture was purified by flash chromatography with 30% ethyl acetate/hexanes to give the tri-tert-butyl 10-(naphthalen-2-ylmethyl)-1,4,7,10-tetraazacyclododecane-1,4,7-tricarboxylate as an oil (314 mg, 80%); $^1$H NMR (400 MHz, CDCl$_3$) δ 7.76-7.68 (m, 3H), 7.62 (s, 1H), 7.42-7.33 (m, 3H), 3.82 (s, 2H), 3.68-3.11 (m, 16H), 2.65 (s, 3H), 1.44-1.32 (m, 27H).

Example 1.4b

Synthesis of Compound 5

To a solution of compound 5a (101 mg, 0.16 mmol) in 10 mL DCM, 5 mL TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78 to give 1-(naphthalen-2-ylmethyl)-1,4,7,10-tetraazacyclododecane as an oil (73 mg, 75%); $^1$H NMR (400 MHz, CD$_3$OD) δ 7.92 (d, J=8.5 Hz, 1H), 7.90-7.86 (m, 2H), 7.86-784 (br, 1H), 7.54-7.49 (m, 3H), 4.02 (s, 2H), 3.27-3.10 (m, 8H), 3.05-2.86 (m, 8H); $^{13}$C NMR (100 MHz, CD$_3$OD) δ 133.4, 133.1, 132.4, 128.9, 128.4, 127.5, 127.3, 126.9, 126.2, 126.1, 57.0, 47.8, 44.4, 42.0 41.8; LRMS (ESI+) m/z calc'd for C$_{19}$H$_{28}$N$_4$ [M+H]$^+$ 312.23. found 313.27; HRMS, (ESI+) m/z calc'd for C$_{19}$H$_{29}$N$_4$ [M+H]$^+$ 313.2387. found 313.2395; rpHPLC t$_R$: condition (A) 9.530 min., condition (B) 13.277 min., purity 99.5% and 98.6% respectively.

Example 1.5

Synthesis of Compound 7

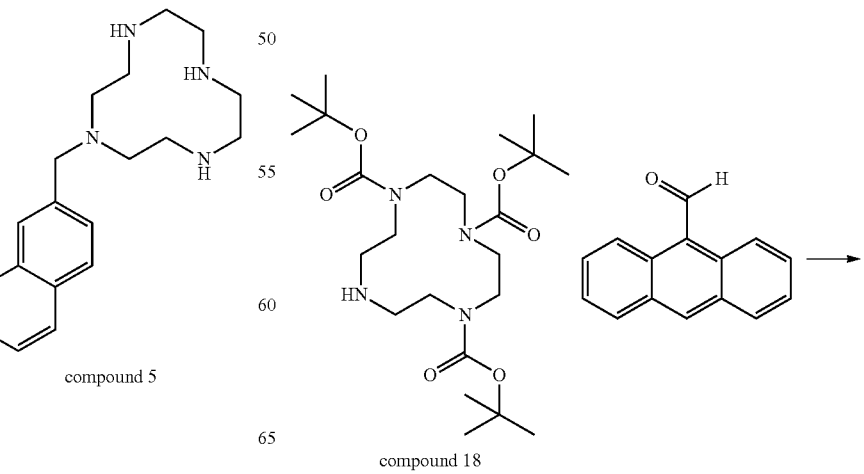

compound 5     compound 18

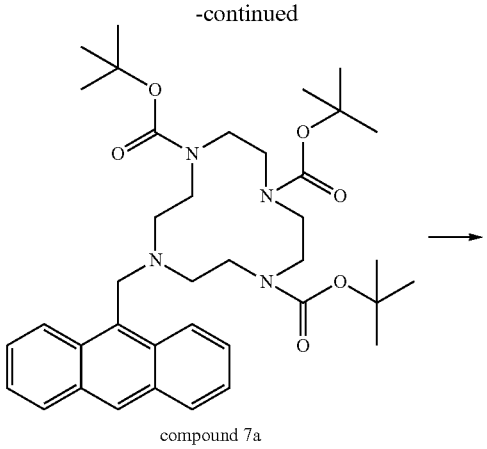

compound 7a

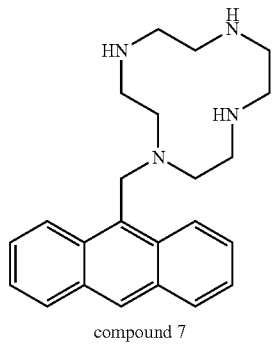

compound 7

Example 1.5a

Synthesis of Compound 7a

To a solution of compound 18 (150 mg, 0.32 mmol) in 3.2 mL DCE, 9-Anthracenecarboxaldehyde (Sigma Aldrich, cat. 278688, 204 mg, 0.99 mmol) was added. To the reaction mixture, 4 Å molecular sieves were added. The mixture was stirred at rt for 3 h, after which sodium triacetoxyborohydride (271 mg, 1.3 mmol) was added. The reaction was left to stir at rt overnight. Upon reaction completion, the crude mixture was filtered through a course porosity sintered glass funnel and the filtrate quenched with water. The aqueous phase was extracted thrice with DCM and the combined organic phase washed with brine. The crude material was purified via flash chromatography employing a 5%-40% gradient of ethyl acetate in hexanes to give 160 mg of the tri-tert-butyl 10-(anthracen-9-ylmethyl)-1,4,7,10-tetraazacyclododecane-1,4,7-tricarboxylate (compound 7a) as a yellow powder; $^1$H NMR (400 MHz, CDCl$_3$) δ 8.47 (d, J=8.8 Hz, 2H), 8.38 (s, 1H), 7.96 (d, J=8.3 Hz, 2H), 7.51-7.40 (m, 4H), 4.67 (s, 2H), 3.43-2.80 (m, 16H), 1.45-1.28 (m, 27H); $^{13}$C NMR (100 MHz, CDCl$_3$) δ 155.7, 155.3, 131.23, 131.20, 128.9, 127.7, 125.7, 125.0, 124.8, 79.1, 60.0, 52.2, 49.1, 47.8, 28.5, 28.3; LRMS (ESI+) m/z calc'd for C$_{38}$H$_{54}$N$_4$O$_6$ [M+H]$^+$ 662.40. found [M+H]$^+$ 663.40. found [M+Na]$^+$ 685.47.

Example 1.5b

Synthesis of Compound 7

To a solution of compound 7a (120 mg, 0.19 mmol) in 3 mL DCM was added 1 mL TFA. The reaction mixture was stirred at −10° C. and the progress of the reaction was monitored using HPLC. Upon completion, the crude mixture was concentrated down in vacuo using MeOH to azeotrope off TFA. The crude mixture was then purified by preparative HPLC to afford 1-(anthracen-9-ylmethyl)-1,4,7,10-tetraazacyclododecane (compound 7) as a slightly brown oil that solidified upon standing; $^1$H NMR (400 MHz, CD$_3$CN) δ 7.23 (s, 1H), 6.98 (d, J=9.1 Hz, 2H), 6.75 (d, 8.6 Hz, 2H), 6.30 (t, J=7.3 Hz, 2H), 6.17 (t, J=7.6 Hz, 2H), 3.47 (s, 2H), 1.77-1.71 (m, 4H), 1.68-1.60 (m, 8H), 1.59-1.50 (m, 4H); $^{13}$C NMR (100 MHz, CD$_3$CN) δ 130.1, 129.4, 128.1, 127.5, 125.6, 125.0, 123.5, 121.5, 48.5, 47.7, 42.4, 40.4, 40.2; LRMS (ESI+) m/z calc'd for C$_{23}$H$_{30}$N$_4$ [M+H]$^+$ 362.25. found 363.34; rpHPLC t$_R$: condition (A) 10.287 min., condition (B) 14.659 min., purity 99.1% and 99.0% respectively.

Example 1.6

Synthesis of Compound 8

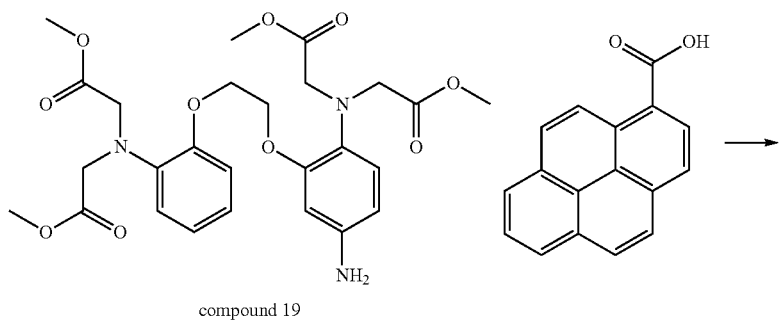

compound 19

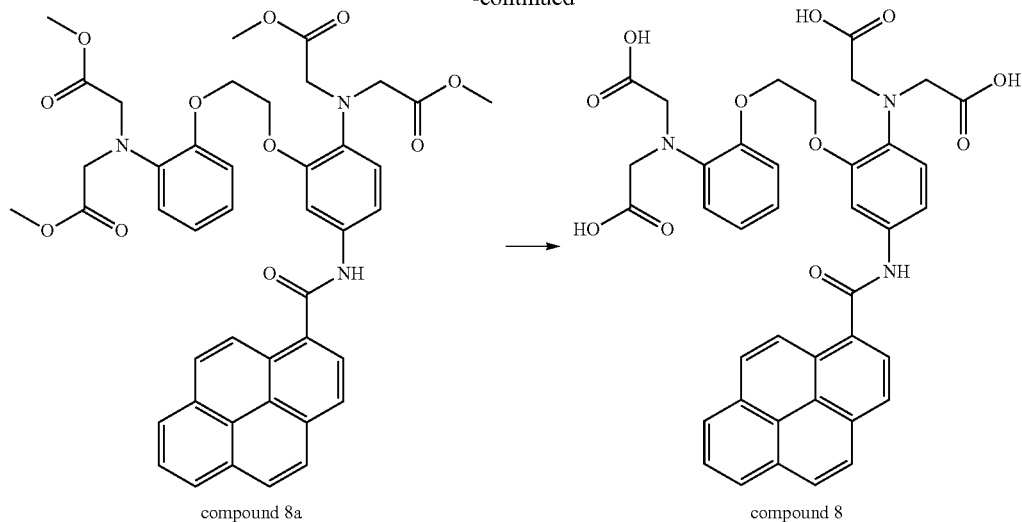

compound 8a → compound 8

Example 1.6a

Synthesis of Compound 8a

A solution of 1-Pyrene carboxylic acid (42 mg, 0.17 mmol) in 4 mL DMF was incubated with TBTU (108 mg, 0.34 mmol) and DIPEA (88 μL, 0.51 mmol) for 20 min. Following incubation, compound 19 (92 mg, 0.17 mmol) was added. The reaction mixture was stirred at rt for 24 h under $N_2$ atmosphere. The reaction mixture was extracted with EtOAc washing 3 times with saturated $NaHCO_{3(aq)}$ and purified by silica gel column chromatography using 1:19 MeOH:DCM eluent to yield dimethyl 2,2'-((2-(2-(2-(bis(2-methoxy-2-oxoethyl)amino)-5-(pyrene-1-carboxamido)phenoxy)ethoxy)phenyl)azanediyl)diacetate as a white solid (85 mg, 65%). $^1$H NMR (400 MHz, $CDCl_3$) δ 8.55 (s, 1H), 8.45 (d, J=9.2 Hz, 1H), 8.13 (t, J=7.7 Hz, 2H), 8.01-7.94 (m, 4H), 7.88 (d, J=9.0 Hz, 1H), 7.50 (s, 1H), 7.32 (d, J=8.5 Hz, 1H), 6.93-6.72 (m, 5H), 4.27 (s, 2H), 4.19 (s, 2H), 4.16-4.06 (m, 9H), 3.55 (s, 6H), 3.47 (s, 6H); $^{13}$C NMR (100 MHz, $CDCl_3$) δ 171.8, 171.7, 150.5, 150.3, 138.9, 135.8, 133.6, 132.3, 130.9, 130.8, 130.4, 128.5, 128.45, 128.36, 127.6, 126.8, 126.1, 125.7, 125.6, 124.45, 124.36, 124.0, 123.9, 122.3, 121.2, 119.2, 119.1, 113.7, 112.9, 112.8, 106.5, 67.4, 66.8, 53.3, 53.1, 51.5, 51.4.

Example 1.6b

Synthesis of Compound 8

Compound 8a (100 mg, 0.12 mmol) was dissolved in 10 mL of a 1:1 mixture of water and THF. $LiOH.H_2O$ (26 mg, 0.62 mmol) was added and the reaction mixture was allowed to stir for 2 hours. 50 mL of 1M NaOH was added the reaction mixture was washed twice with 50 mL of EtOAc. The aqueous layer was then acidified with HCl and extracted 3 times with 50 mL portions of EtOAc. The solvent was removed in vacuo to yield a white solid. The product was lyophilised to give 2,2'-((2-(2-(2-(bis(carboxymethyl)amino)-5-(pyrene-1-carboxamido)phenoxy)ethoxy)phenyl)azanediyl)diacetic acid (compound 8) as a white solid (92 mg, quant.); $^1$H NMR (400 MHz, $CD_3OD$) δ 8.48 (d, J=9.3 Hz, 1H), 8.25 (t, J=7.0 Hz, 3H), 8.17 (t, J=9.8 Hz, 3H), 8.13-8.02 (m, 2H), 7.61 (s, 1H), 7.29 (d, J=8.8 Hz, 1H), 7.05-6.82 (m, 5H), 4.37 (d, J=7.2 Hz, 4H), 4.18-4.05 (m, 8H); HRMS, (ESI+) m/z calc'd for $C_{39}H_{34}N_3O_{11}$ $[M+H]^+$ 720.2188. found 720.2193; rpHPLC $t_R$: condition (A) 18.478 min., condition (B) 27.506 min.

Example 1.7

Synthesis of Compound 9

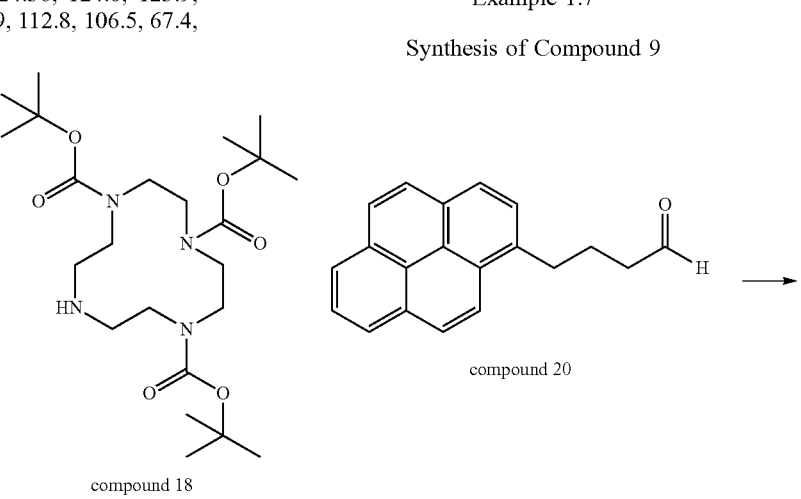

compound 18                    compound 20

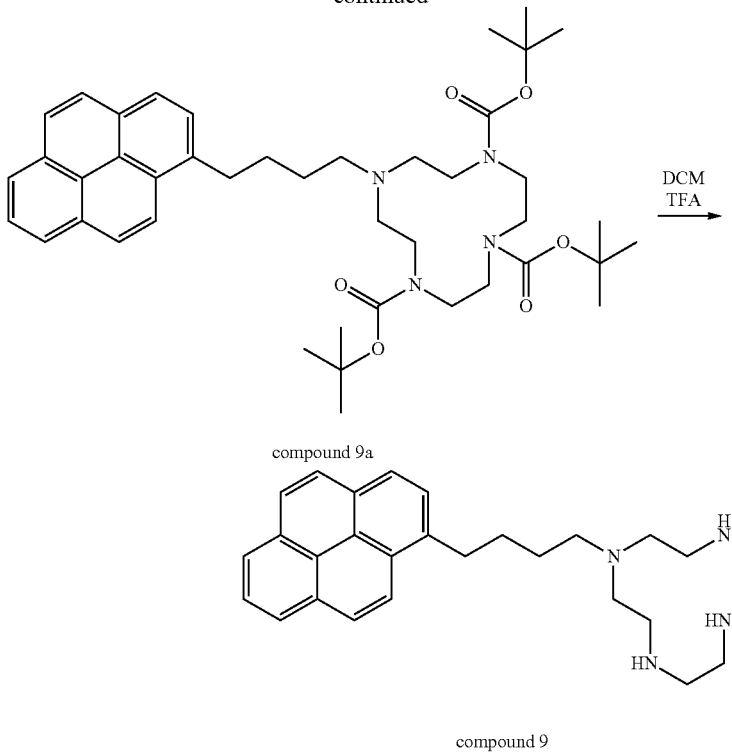

compound 9a compound 9

Example 1.7a

Synthesis of Compound 9a

To a solution of compound 20 (96 mg, 0.35 mmol) in 10 mL 1,2-dichloroethane (DCE), compound 18 (167 mg, 0.35 mmol) was added and stirred together with 4 Å molecular sieves for 2 h under $N_2$ atmosphere. To this solution sodium triacetoxyborohydride (90 mg, 0.42 mmol) was added and the reaction mixture was allowed to stir at ambient temperature over 24 h under $N_2$ atmosphere. Subsequently, the reaction mixture was extracted with ethyl acetate (EtOAc) and washed three times with sodium bicarbonate. The extract was purified by flash chromatography with ethyl acetate/hexanes (1:1) to give the tri-tert-butyl 10-(4-(pyren-1-yl)butyl)-1,4,7,10-tetraazacyclododecane-1,4,7-tricarboxylate (compound 9a) as a white solid (212 mg, 83%); $^1$H NMR (400 MHz, $CDCl_3$) δ 8.25 (d, J=9.2 Hz, 1H), 8.18-8.13 (m, 2H), 8.12-8.07 (m, 2H), 8.05-7.95 (m, 3H), 7.84 (d, J=7.8 Hz, 1H), 3.37-3.08 (m, 14H), 2.56 (s, 2H), 2.43-2.36 (m, 3H), 1.87-1.73 (m, 4H), 1.68-1.54 (m, 4H), 1.51-1.37 (m, 27H); $^{13}$C NMR (100 MHz, $CDCl_3$) δ 155.5, 155.4, 136.7, 131.3, 130.8, 129.6, 128.4, 127.4, 127.09, 127.05, 126.4, 125.7, 124.95, 124.89, 124.72, 124.66, 124.5, 123.2, 79.2, 55.2, 51.3, 46.9, 45.5, 33.4, 29.7, 28.4, 28.3, 26.6.

Example 1.7b

Synthesis of Compound 9

To a solution of compound 9a (100 mg, 0.14 mmol) in 15 mL DCM, 1 mL TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78 to give 1-(4-(pyren-1-yl)butyl)-1,4,7,10-tetraazacyclododecane (compound 9) as an oil (54 mg, 90%); $^1$H NMR (400 MHz, $CDCl_3$) δ 8.27 (d, J=9.3 Hz, 1H), 8.16-8.11 (m, 2H), 8.10-8.06 (m, 2H), 8.03-7.94 (m, 3H), 7.85 (d, J=7.8 Hz, 1H), 3.33 (t, J=7.8 Hz, 2H), 2.69-2.64 (m, 4H), 2.61-2.56 (m, 4H), 2.53-2.44 (m, 10H), 1.87 (quint, J=7.8 Hz, 2H), 1.66 (quint, J=7.5 Hz, 2H); $^{13}$C NMR (100 MHz, $CDCl_3$) δ 136.9, 131.3, 130.8, 129.6, 128.4, 127.4, 127.1, 126.9, 126.3, 125.6, 124.91, 124.88, 124.65, 124.63, 124.5, 123.4, 54.4, 51.5, 47.0, 45.8, 45.2, 33.4, 29.7, 27.5; LRMS (ESI+) m/z calc'd for $C_{28}H_{36}N_4$ [M+H]$^+$ 428.29. found 429.17; HRMS, (ESI+) m/z calc'd for $C_{28}H_{37}N_4$ [M+H]$^+$ 429.3013. found 429.3021; rpHPLC $t_R$: condition (A) 12.949 min., condition (B) 20.751 min., purity 99.6% and 99.2% respectively.

Example 1.8

Synthesis of Compound 10

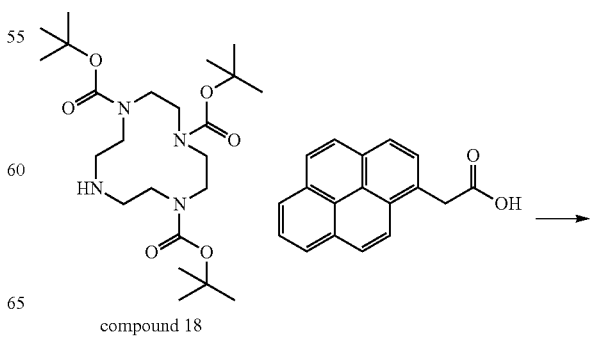

compound 18

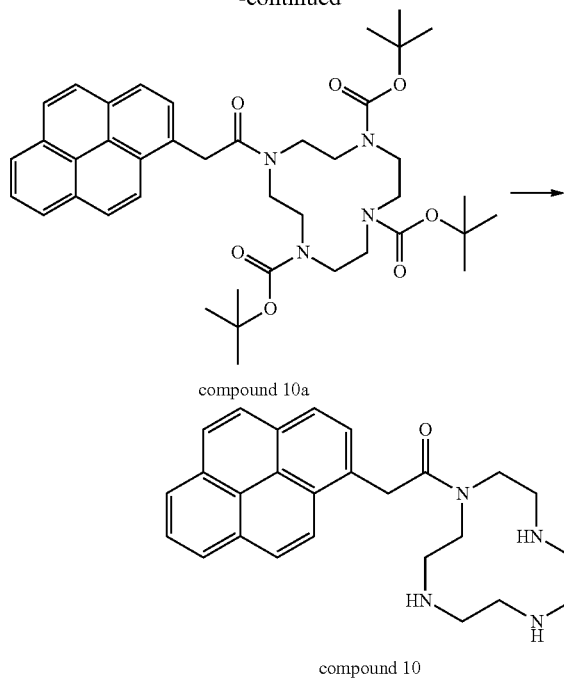

compound 10a compound 10

Example 1.8a

Synthesis of Compound 10a

To a solution of 1-Pyreneacetic acid (Sigma Aldrich, cat. 392189, 100 mg, 0.38 mmol) in 3.8 mL DMF was added compound 18 (179 mg, 0.38 mmol) and TBTU (297 mg, 0.77 mmol) and the reaction mixture was stirred for 20 min. DIPEA (196 μL, 1.14 mmol) was then added to this reaction mixture and stirred at rt for 16 h. Subsequently, this was extracted using sodium bicarbonate. The extract was purified by flash chromatography with 30-40% ethyl acetate/hexanes (1:1) to give the tri-tert-butyl 10-(2-(pyren-1-yl)acetyl)-1,4,7,10-tetraazacyclododecane-1,4,7-tricarboxylate (compound 10a) (217 mg, 80%); $^1$H NMR (400 MHz, CDCl$_3$) δ 8.25 (d, J=8.9 Hz, 1H), 8.19-8.11 (m, 4H), 8.03 (s, 2H), 7.99 (d, J=7.6 Hz, 1H), 7.91 (d, J=7.8 Hz, 1H), 4.43 (s, 2H), 3.87-3.23 (m, 16H), 1.56-1.43 (m, 27H).

Example 1.8a

Synthesis of Compound 10

To a solution of compound 10a (106 mg, 0.15 mmol) in 10 mL DCM, 5 mL TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78. This was lyophilized with water/acetonitrile to give 1-(1,4,7,10-tetraazacyclododecan-1-yl)-2-(pyren-1-yl)ethan-1-one (compound 10) as an off white powder (45 mg, 72%); mp 75-79° C.; $^1$H NMR (400 MHz, CDCl$_3$) δ 8.23 (d, J=9.2 Hz, 1H), 8.18-8.06 (m, 4H), 8.04-7.94 (m, 3H), 7.84 (d, J=7.8 Hz, 1H), 4.47 (s, 2H), 3.60-3.54 (br, 4H), 3.39 (s, 1H), 2.88 (s, 1H), 2.84 (s, 1H), 2.79-2.72 (m, 4H), 2.72-2.65 (m, 2H), 2.62-2.52 (m, 6H); LRMS (ESI+) m/z calc'd for C$_{26}$H$_{31}$N$_4$O [M+H]$^+$ 415.25. found 416.27; HRMS (ESI+) m/z calc'd for C$_{26}$H$_{31}$N$_4$O [M+H]$^+$ 415.2498. found 415.2502; rpHPLC t$_R$: condition (A) 12.241 min., condition (B) 17.924 min., purity 100.0% and 97.887% respectively.

Example 1.9

Compound 3

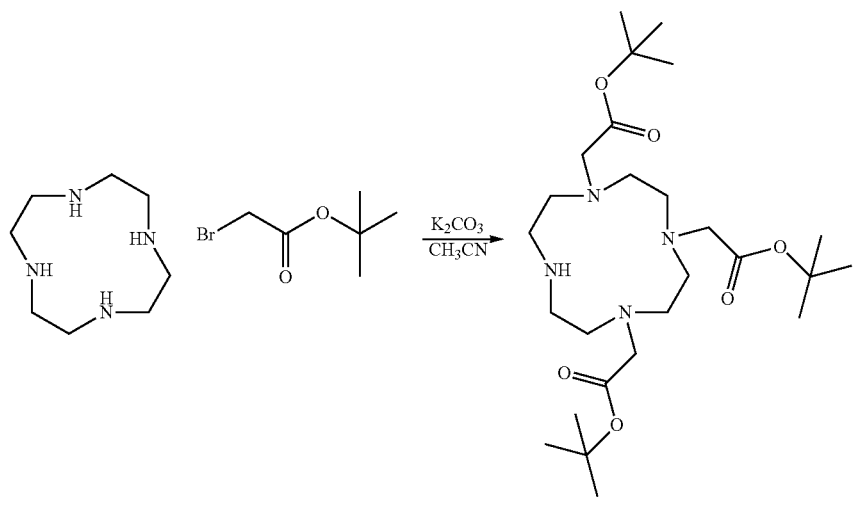

compound 3a

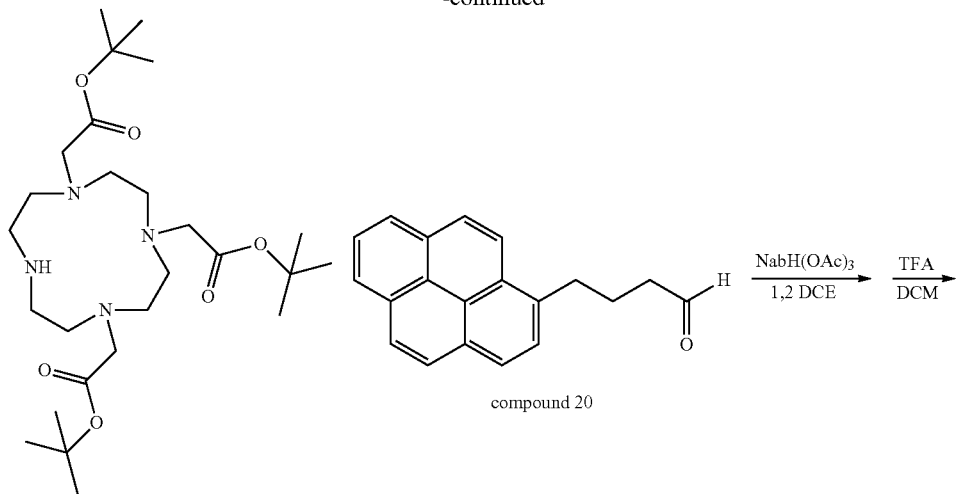

compound 3a

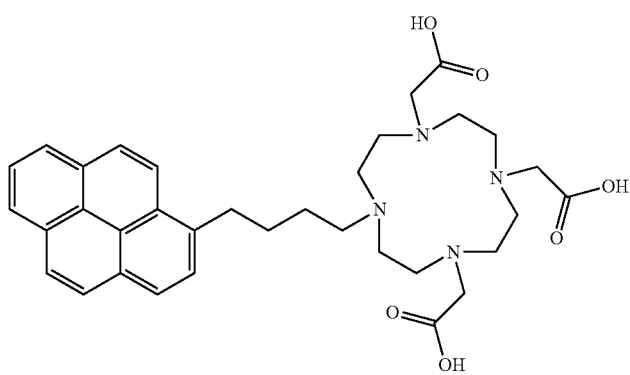

compound 3

To a solution of compound 3a (90 mg, 0.1749 mmol) in 1.3 mL 1,2-DCE, compound 20 (47.63 mg, 0.1749 mmol) was added. To this mixture, 4 Å molecular sieves were added. The reaction mixture was stirred for 4 h. To this reaction mixture, sodium triacetoxyborohydride (44.51 mg, 0.2099 mmol) was added and the reaction was left to stir at rt overnight under $N_2$ atmosphere.

The solvent was removed in vacuo and the obtained residue was re-dissolved in 2.5 mL of DCM, to which 1.5 mL of TFA was added. The reaction mixture was stirred at rt. The progress of the reaction was monitored using MS. The reaction mixture was concentrated down in vacuo and the TFA was azeotroped off in vacuo with MeOH. The mixture was then purified by preparative HPLC to give 2,2',2''-(10-(4-(pyren-1-yl)butyl)-1,4,7,10-tetraazacyclodo-decane-1,4,7-triyl)triacetic acid (compound 3) (24 mg, 22%). $^1$H NMR (400 MHz, $CD_3OD$) δ 8.34 (d, J=9.2 Hz, 1H), 8.22-8.11 (m, 4H), 8.05 (s, 2H), 8.00 (t, J=7.6 Hz, 1H), 7.92 (d, J=7.9 Hz, 1H), 4.14 (s, 2H), 3.71-3.32 (m, 14H), 3.16-2.82 (m, 8H), 2.14 (s, 2H), 2.07-1.90 (m, 4H); $^{13}$C NMR (100 MHz, $CD_3OD$) δ 173.2, 167.5, 135.5, 131.3, 130.7, 129.9, 128.3, 127.0, 126.9, 126.3, 125.5, 124.7, 124.54, 124.48, 124.3, 122.7, 118.0, 115.1, 54.7, 54.3, 52.0, 51.4, 49.6, 48.3, 48.0, 32.2, 28.1, 23.0; LRMS (ESI+) m/z calc'd for $C_{34}H_{44}N_4O_6$ $[M+H]^+$ 604.30. found 604.30, $[M+Na]^+$ found 625.27; HRMS, (ESI+) m/z calc'd for $C_{34}H_{43}N_4O_6$ $[M+H]^+$ 603.3177. found 603.3188; rpHPLC $t_R$: condition (A) 14.205 min., condition (B) 21.115 min., purity 98.5% and 92.0% respectively.

Example 1.10

Compound 6

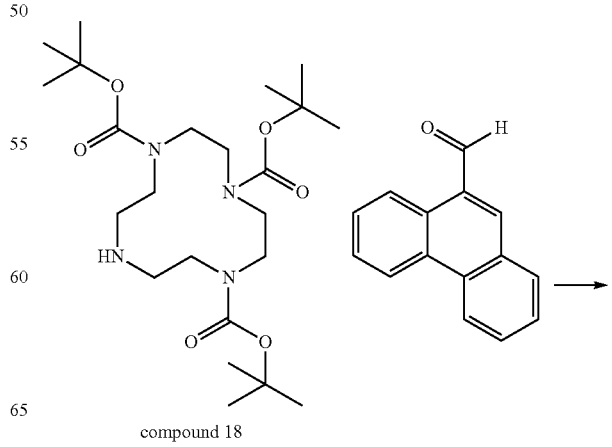

compound 18

-continued

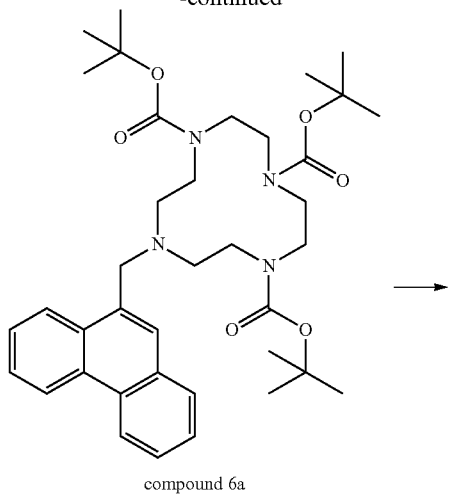

compound 6a

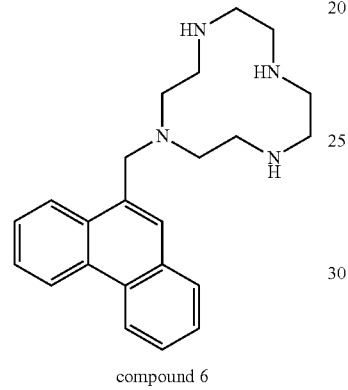

compound 6

To a solution of compound 6a (100 mg, 0.15 mmol) in 10 mL DCM, 10 mL TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-1-(phenanthren-9-ylmethyl)-1,4,7,10-tetraazacyclododecane (compound 6) (39 mg, 71%) as an oil; $^1$H NMR (400 MHz, CD$_3$CN) δ 8.81 (d, J=8.5 Hz, 1H), 8.72 (d, J=8.2 Hz, 1H), 8.07 (d, J=8.7 Hz, 1H), 7.95 (d, J=7.9 Hz, 1H), 7.83 (s, 1H), 7.77-7.64 (m, 4H), 4.31 (s, 2H), 3.21-2.85 (m, 16H); $^{13}$C NMR (100 MHz, CD$_3$CN) δ 131.0, 130.8, 130.3, 130.1, 129.1, 128.7, 127.4, 127.3, 127.02, 126.96, 123.7, 123.4, 122.5, 114.4, 55.9, 49.3, 44.1, 42.4, 41.9; LRMS (ESI+) m/z calc'd for C$_{23}$H$_{30}$N$_4$ [M+H]$^+$ 362.25. found 362.42; HRMS, (ESI+) m/z calc'd for C$_{23}$H$_{31}$N$_4$ [M+H]$^+$ 363.2543. found 363.2547; rpHPLC t$_R$: condition (A) 10.693 min., condition (B) 15.298 min., purity 100% and 100% respectively.

y

Example 1.11

Compound 11

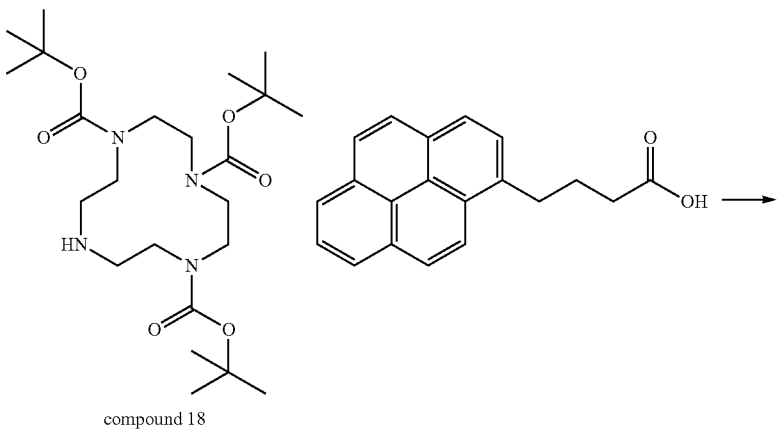

compound 18

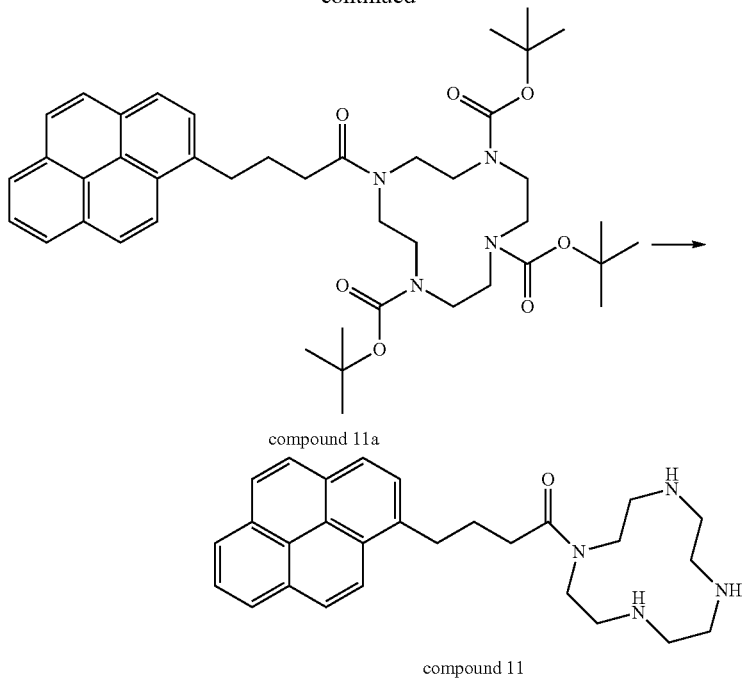

compound 11a compound 11

To a solution of compound 11a (102 mg, 0.14 mmol) in 10 mL DCM, 5 mL TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78 to give 1-(1,4,7,10-tetraazacyclododecan-1-yl)-4-(pyren-1-yl)butan-1-one (compound 11) (49 mg, 79%); mp 83-86° C.; $^1$H NMR (400 MHz, CD$_3$OD) δ 8.31 (d, J=9.3 Hz, 1H), 8.15-8.10 (m, 2H), 8.09-8.04 (m, 2H), 8.01-7.91 (m, 3H), 7.84 (d, J=7.8 Hz, 1H), 3.60-3.53 (m, 4H), 3.36-3.29 (m, 2H), 3.10 (br, 10H), 3.00 (br, 2H), 2.53 (t, J=7.3 Hz, 2H), 2.08 (quint, J=7.7 Hz, 2H); LRMS (ESI+) m/z calc'd for C$_{28}$H$_{35}$N$_4$O [M+H]$^+$ 443.28. found 444.22; HRMS (ESI+) m/z calc'd for C$_{28}$H$_{35}$N$_4$O [M+H]$^+$ 443.2811. found 443.2815; rpHPLC t$_R$: condition (A) 13.382 min., condition (B) 19.843 min., purity 100.0% and 99.8% respectively.

Example 1.12

Compound 12

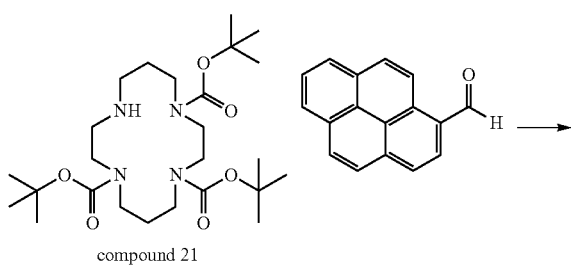

compound 21

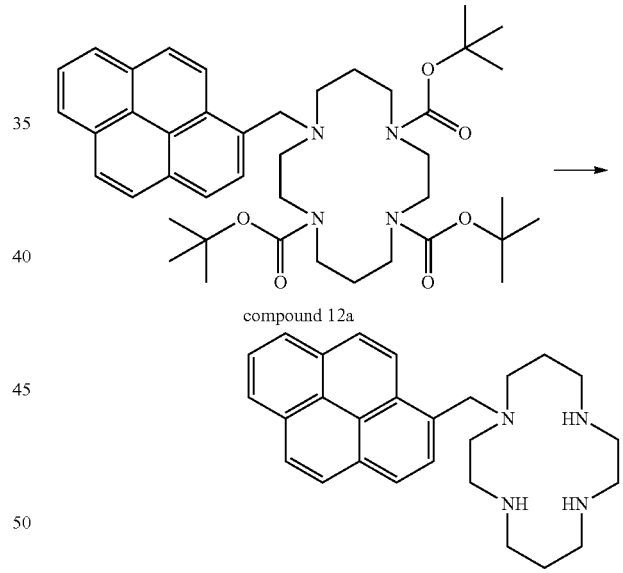

compound 12a compound 12

To a solution of compound 12a (108 mg, 0.15 mmol) in 10 mL DCM, 5 mL TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78 to give 1-(pyren-1-ylmethyl)-1,4,8,11-tetraazacyclotetradecane (compound 12) (45 mg, 72%); mp 101-104° C.; $^1$H NMR (400 MHz, CDCl$_3$) δ 8.47 (d, J=9.3 Hz, 1H), 8.18-8.05 (m, 5H), 8.02 (s, 2H), 7.97 (t, J=7.6 Hz, 1H), 4.19 (s, 2H), 2.90-2.79 (m, 6H), 2.78-2.74 (m, 2H), 2.70-2.64 (m, 6H), 2.62-2.57 (m, 2H), 2.56-2.48 (m, 4H), 1.87 (quint, J=5.3 Hz, 2H), 1.60 (quint, J=5.3 Hz, 2H); $^{13}$C NMR (100 MHz, CDCl$_3$) δ 132.8, 131.2, 130.6, 130.4, 129.5, 128.0, 127.3, 127.0, 126.9, 125.7, 124.9, 124.8, 124.74, 124.72, 124.4, 123.5, 56.8, 54.8, 54.1, 50.3, 48.9, 48.6, 48.3, 47.5, 47.4, 27.9, 26.4; LRMS (ESI+) m/z calc'd for C$_{27}$H$_{35}$N$_4$ [M+H]$^+$ 415.29. found 415.20; HRMS (ESI+) m/z calc'd for C$_{27}$H$_{35}$N$_4$ [M+H]$^+$ 415.2862. found 415.2854; rpHPLC t$_R$: condition (A) 12.499 min., condition (B) 19.601 min., purity 99.8% and 96.1% respectively.

Example 1.13

Compound 13

Example 1.14

Compound 14

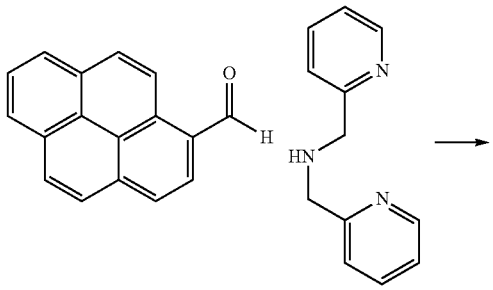

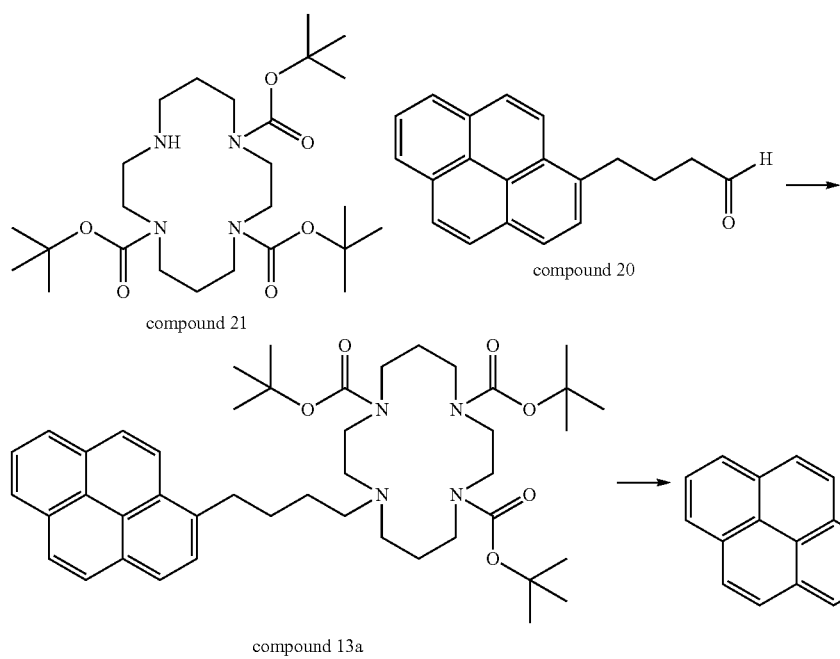

To a solution compound 13a (79 mg, 0.1 mmol) in 15 mL DCM, 1 mL TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78 to give 1-(4-(pyren-1-yl)butyl)-1,4,8,11-tetraazacyclotetradecane (compound 13); $^1$H NMR (400 MHz, CDCl$_3$) δ 8.30 (d, J=9.3 Hz, 1H), 8.17-8.08 (m, 4H), 8.04-7.95 (m, 3H), 7.88 (d, J=7.8 Hz, 1H), 3.35 (t, J=7.5 Hz, 2H), 2.62 (t, J=5.3 Hz, 2H), 2.59-2.54 (m, 4H), 2.51-2.47 (m, 2H), 2.46-2.41 (m, 4H), 2.40-2.33 (m, 4H), 2.24-2.20 (m, 2H), 1.85 (quint, J=8.1 Hz, 2H), 1.73-1.66 (m, 2H), 1.65-1.59 (m, 2H), 1.59-1.51 (m, 2H); $^{13}$C NMR (100 MHz, CDCl$_3$) δ 137.1, 131.3, 130.8, 129.6, 128.4, 127.3, 127.2, 127.1, 126.4, 125.6, 124.9, 124.67, 124.65, 124.5, 123.4, 54.6, 54.2, 52.6, 51.2, 49.8, 49.3, 48.5, 47.7, 47.6, 33.4, 30.0, 28.6, 26.4, 26.1; LRMS (ESI+) m/z calc'd for C$_{30}$H$_{40}$N$_4$ [M+H]$^+$ 456.33. found 457.32.

-continued

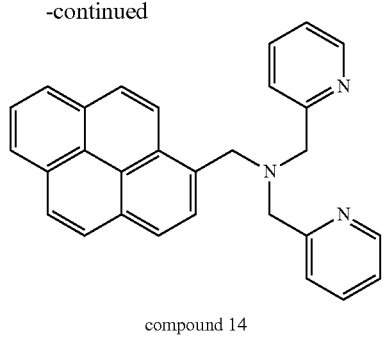

compound 14

To a solution of 1-Pyrenealdehyde (200 mg, 0.87 mmol) in 4.35 mL DCE, Di-(2-picolyl)amine (DPA) (137.4 µL, 0.87 mmol) was added along with sodium triacetoxyborohydride (553.2 mg, 2.61 mmol). To this reaction mixture, 4 Å molecular sieves were added. The mixture was left to stir at rt overnight. This was then passed through a column packed with Amberlite IRN-78. This was purified by flash chromatography with Titanic/DCM (1:1) to give 1-(pyren- 1-yl)-N,N-bis(pyridin-2-ylmethyl)methanamine (compound 14) (291 mg, 81%); mp 108-112° C.; ¹H NMR (400 MHz, CDCl₃) δ 8.53 (d, J=4.7 Hz, 2H), 8.40 (d, J=9.3 Hz, 1H), 8.20-8.06 (m, 5H), 8.05-7.97 (m, 3H), 7.61 (t, J=7.6 Hz, 2H), 7.49 (d, J=7.8 Hz, 2H), 7.12 (t, J=6.3 Hz, 2H), 4.47 (s, 2H), 3.99 (s, 4H); ¹³C NMR (100 MHz, CDCl₃) δ 148.5, 136.5, 131.1, 130.73, 130.67, 129.8, 128.3, 127.3, 127.1, 127.0, 125.7, 124.90, 124.86, 124.6, 124.4, 123.9, 123.4, 122.0, 77.1, 60.1, 57.0; LRMS (ESI+) m/z calc'd for $C_{29}H_{24}N_3$ [M+H]⁺ 414.20. found 414.24; HRMS (ESI+) m/z calc'd for $C_{29}H_{24}N_3$ [M+H]⁺ 414.1970. found 414.1981; rpHPLC $t_R$: condition (A) 13.531 min., condition (B) 19.731 min., purity 98.8% and 97.5% respectively.

Example 1.15

Compound 15

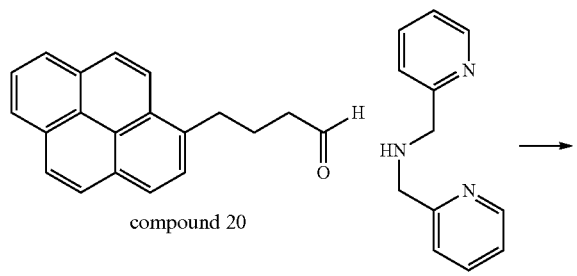

compound 20

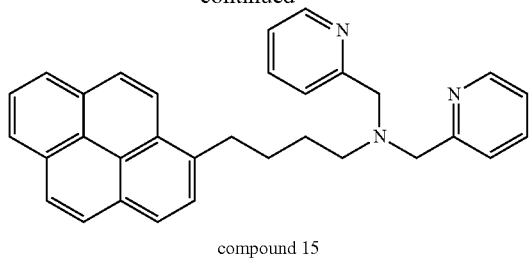

compound 15

To a solution of compound 20 (143 mg, 0.526 mmol) in 2.6 mL DCE, DPA (95 µL, 0.526 mmol) was added along with sodium triacetoxyborohydride (334 mg, 1.578 mmol). To this reaction mixture, 4 Å molecular sieves were added. The mixture was left to stir at rt overnight. The mixture was extracted with DCM/sodium bicarbonate. The extract was purified by flash chromatography with Titanic/DCM (1:1) to give 4-(pyren-1-yl)-N,N-bis(pyridin-2-ylmethyl)butan-1-amine (compound 15) (189 mg, 79%); mp 61-62° C.; ¹H NMR (400 MHz, CDCl₃) δ 8.52 (d, J=4.8 Hz, 2H), 8.19 (d, J=9.5 Hz, 1H), 8.15-8.10 (m, 2H), 8.07-8.02 (m, 2H), 8.01-7.94 (m, 3H), 7.76 (d, J=7.8 Hz, 1H), 7.53 (td, J=7.8 Hz, 1.3 Hz, 2H), 7.46 (d, J=7.8 Hz, 2H), 7.06 (t, J=6.2 Hz, 2H), 3.83 (s, 4H), 3.24 (t, J=7.4 Hz, 2H), 2.65 (t, J=7.1 Hz, 2H), 1.84 (quint, J=7.5 Hz, 2H), 1.71 (quint, J=7.5 Hz, 2H); ¹³C NMR (100 MHz, CDCl₃) δ 159.9, 148.8, 136.7, 136.2, 131.3, 130.8, 129.6, 128.4, 127.4, 127.1, 127.0, 126.4, 125.6, 124.94, 124.91, 124.7, 124.6, 124.5, 123.3, 122.8, 121.7, 60.5, 54.2, 33.1, 29.3, 27.0; LRMS (ESI+) m/z calc'd for $C_{32}H_{30}N_3$ [M+H]⁺ 456.24. found 456.31; HRMS (ESI+) m/z calc'd for $C_{32}H_{30}N_3$ [M+H]⁺ 456.2440. found 456.2445; rpHPLC $t_R$: condition (A) 17.561 min., condition (B) 26.221 min., purity 98.8% and 98.9% respectively.

Example 1.16a

Compound 16

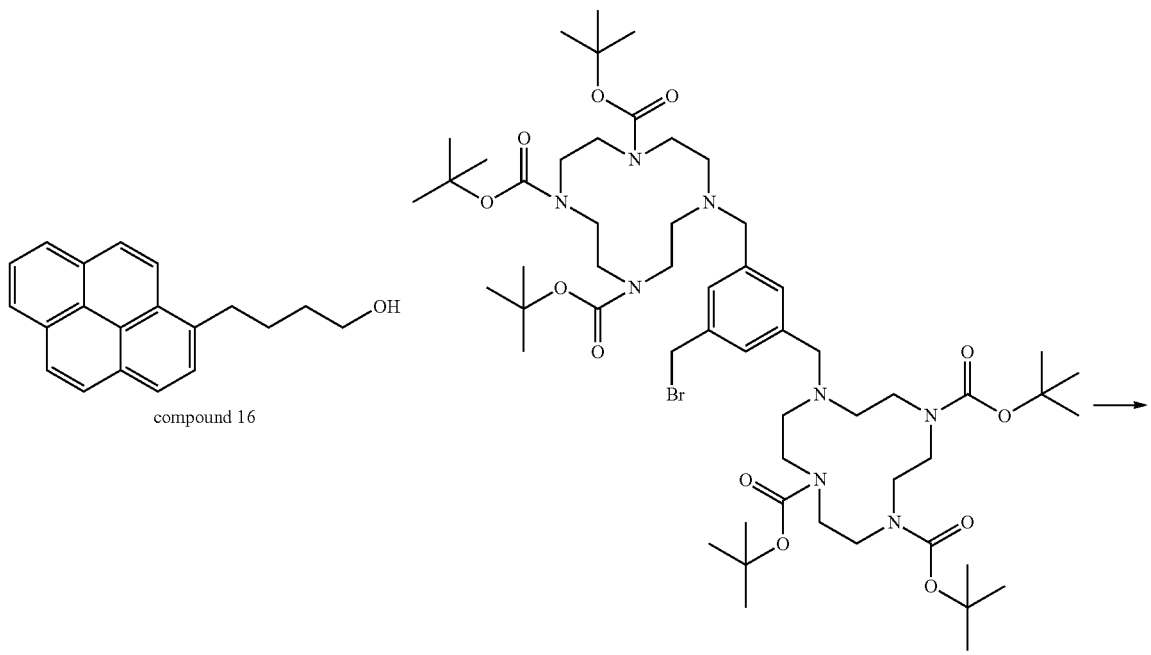

compound 16

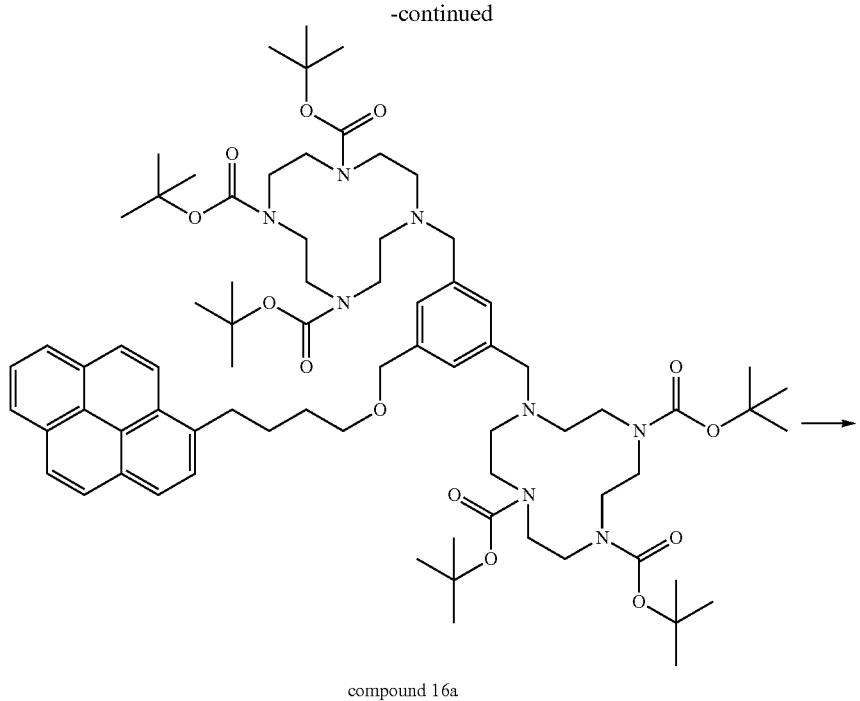

compound 16a

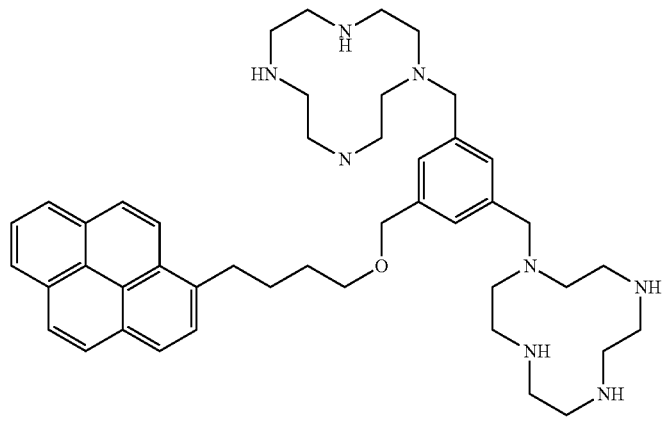

compound 16

To a solution of compound 16a (102 mg, 0.077 mmol) in 5 mL DCM, 5 mL TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78 to give 1,1'-((5-((4-(pyren-1-yl)butoxy)methyl)-1,3-phenylene)bis(methylene))bis(1,4,7,10-tetraazacyclododecane) (compound 16); mp 55-60° C.; $^1$H NMR (400 MHz, CD$_3$CN) δ 8.31 (d, J=9.3 Hz, 1H), 8.21 (d, J=7.7 Hz, 2H), 8.16 (d, J=7.8 Hz, 1H), 8.11 (d, J=9.2 Hz, 1H), 8.07 (d, J=2.1 Hz, 2H), 8.03 (t, J=7.6 Hz, 1H) 7.91 (d, J=7.8 Hz, 1H), 7.17 (s, 2H), 7.10 (s, 1H), 4.43 (s, 2H), 3.63 (s, 4H), 3.3.52 (t, J=6.3 Hz, 2H), 3.33 (t, J=7.8 Hz, 2H), 3.20-2.50 (m, 32H), 1.91-1.81 (m, 2H), 1.80-1.70 (m, 2H); $^{13}$C NMR (100 MHz, CD$_3$CN) δ 140.4, 137.4, 136.5, 131.2, 130.7, 130.0, 129.5, 128.34, 128.28, 127.4, 127.0, 126.4, 126.1, 124.9, 124.8, 124.7, 124.53, 124.45, 123.5, 120.5, 117.6, 114.7, 111.8, 71.5, 69.8, 56.5, 47.8, 44.2, 41.8, 41.7, 32.6, 29.4, 28.5; LRMS (ESI+) m/z calc'd for C$_{45}$H$_{65}$N$_8$O [M+H]$^+$ 733.53. found 733.47; HRMS (ESI+) m/z calc'd for C$_{45}$H$_{65}$N$_8$O$_1$ [M+H]$^+$ 733.5281. found 733.5265; rpHPLC t$_R$: condition (A) 12.470 min., condition (B) 18.539 min., purity 99.8% and 99.4% respectively.

Example 1.17a
Compound 17
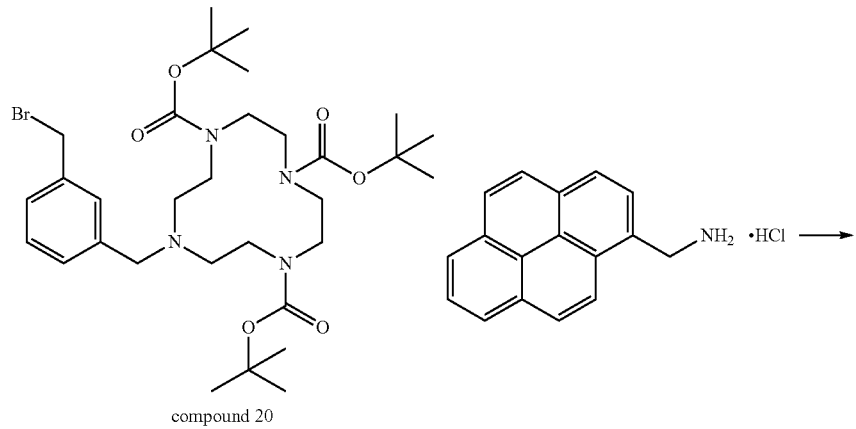
compound 20
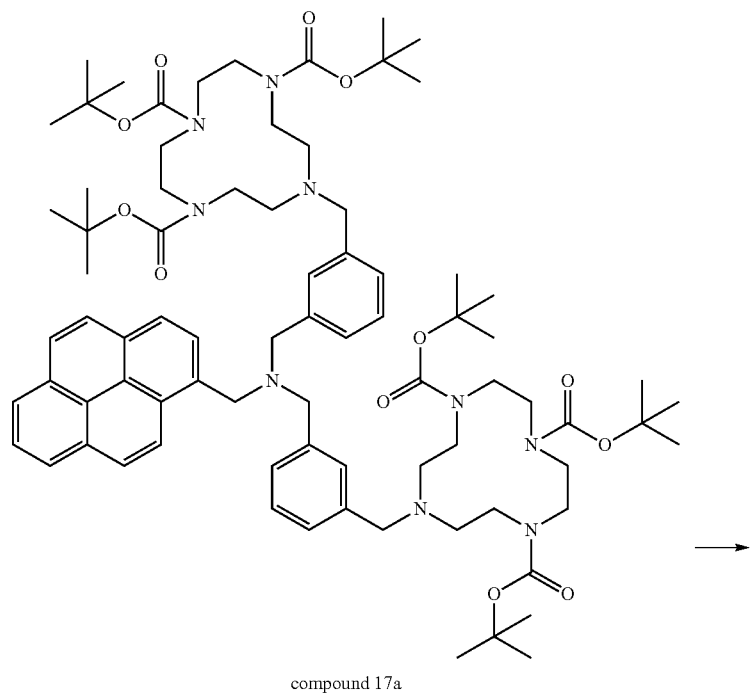
compound 17a

-continued

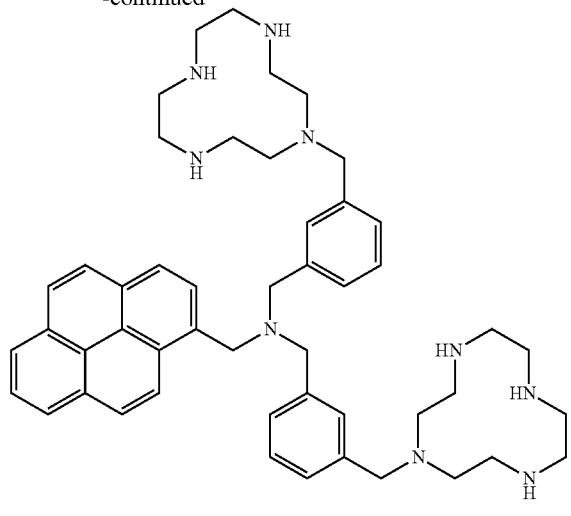

compound 17

To a solution of compound 17a in 15 mL DCM, 1 ml TFA was added. The reaction mixture was stirred at rt. The progress of the reaction was monitored using MS. The reaction mixture was concentrated down in vacuo and the TFA was azeotroped off in vacuo with MeOH. The crude product was taken up in MeOH and passed through a column packed with Amberlite IRN-78. The solvent was evaporated in vacuo. The mixture was then purified by preparative HPLC. The product was again passed through a column packed with Amberlite IRN-78 to give N,N-bis(3-((1,4,7,10-tetraazacyclododecan-1-yl)methyl)benzyl)-1-(pyren-1-yl)methanamine (compound 17); $^1$H NMR (400 MHz, CDCl$_3$) 8.35 (d, J=9.1 Hz, 1H), 8.20-8.07 (m, 4H), 8.06-7.94 (m, 4H), 7.30-7.22 (m, 6H), 7.20-7.14 (br, 2H), 4.21 (s, 2H), 3.68-3.57 (br, 8H), 2.80-2.40 (m, 38H); $^{13}$C NMR (100 MHz, CDCl$_3$) δ 139.1, 138.4, 133.1, 130.8, 130.4, 129.9, 129.7, 128.1, 127.8, 127.6, 127.3, 126.8, 126.7, 125.6, 124.8, 124.73, 124.68, 124.6, 124.3, 59.0, 58.4, 56.6, 51.0, 47.0, 46.2, 45.0; LRMS (ESI+) m/z calc'd for C$_{49}$H$_{65}$N$_9$ [M+H]$^+$ 779.54. found 780.55, [M+Na]$^+$ found 802.55.

Example 2

Fluorescence Measurements and Imaging Experiments

All experiments were performed in triplicate. Tecan Infinite M1000 µlate reader was used for all solution fluorescence intensity measurements at 400 Hz in black 384 well, flat bottom plates. All solution experiments were performed in 5% DMSO/50 mM HEPES buffer, pH 7.2, unless otherwise noted. All gels were run in 25 mM Tris/192 mM glycine/0.1% SDS buffer, pH 8.3. All fluorescence imaging was performed using BIORAD ChemiDoc MP imaging system.

Fluorescence enhancement factors (F$_e$) were calculated using the following formula:

$$F_e = \frac{\frac{\text{excimer emission with analyte}}{\text{monomer emission with analyte}}}{\frac{\text{excimer emission without analyte}}{\text{monomer emission without analyte}}},$$

where monomer emission is defined as the integrated area from 366-386 nm (or point fluorescence measurement at 376 nm with bandwidth of 10-20 nm) and excimer emission is defined as the integrated area from 466-486 nm (or point fluorescence measurement at 476 nm with bandwidth of 10-20 nm), for pyrene derivatives only. Wavelengths for other fluorophores vary depending on the nature of the fluorophore.

Δ Fluorescence Intensity values were calculated using the following formula:

$$\Delta \text{ Flourescence Intensity} = \frac{\text{excimer emission analyte}}{\text{excimer emission buffer}},$$

where excimer emission is defined as the integrated area from 466-486 nm (or point fluorescence measurement at 476 nm with bandwidth of 10-20 nm), for pyrene derivatives only. Wavelengths for other fluorophores vary depending on the nature of the fluorophore.

Example 3

Peptide Studies: Serial Dilution Fluorescence Intensity Measurements

Figure 1:
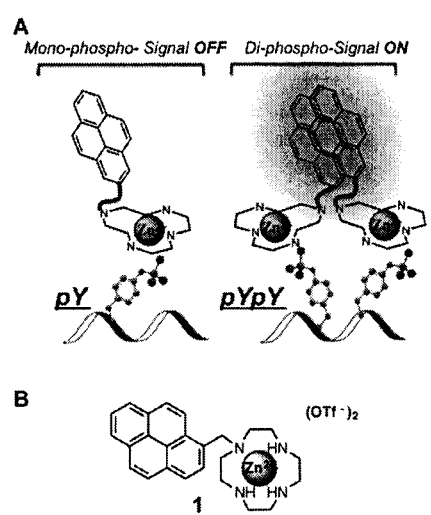
Figure 2:
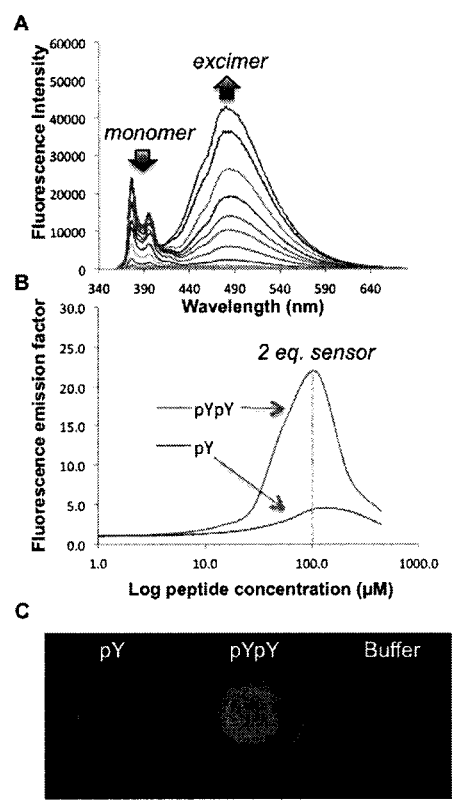

For initial testing, compound 1 complexed with zinc(II) (triflate salt) (FIG. 1B) was evaluated against peptide sequences containing mono- and di-phosphorylated sites (AYpYAA and ApYpYAA) as models of differentially phosphorylated proteins. All experiments were performed in aqueous solutions under physiological conditions (HEPES). As predicted, upon excitation at 350 nm, compound 1 produced a pronounced shift in emission from the 380 to 480 nm region in response to pYpY-containing peptides at concentrations as low as $10^{-6}$ M (FIG. 2A). This shift, attributed to excimer formation, was at least 5-fold lower in response to mono-phosphorylated pY peptides at all concentrations tested (3-250 µM of peptide), suggesting that strong excimer signal emission is specific to a di-phosphorylated motif. As pY peptides induced minor excimer formation, it was hypothesized that while not favorable, pY association with two molecules of the compound 1 can occur.

Compound 1-$Zn^{2+}$ is a pyrene-mediated excimer emission compound which acts as a turn-on fluorescent reporter component. Briefly, when two pyrene molecules associate, there is an observed increase in excimer emission in the 480 nm region.[8,9] The binding component of compound 1-$Zn^{2+}$ is a Lewis Zn(II)-coordination complex that non-specifically binds all phosphorylated sites. Since only proximal pyrene molecules produce an excimer signal, a pyrene coupled to Zn(II)-cyclen macrocycle, preferentially forms a 1:1 complex with a pX-containing peptide/protein site and therefore does not produce an excimer signal (FIG. 1A). However, for proximally di-phosphorylated peptides, each pX residue coordinates a Zn(II)-cyclen unit, facilitating pyrene interaction and resultant excimer emission (FIG. 1A).

Figure 4:
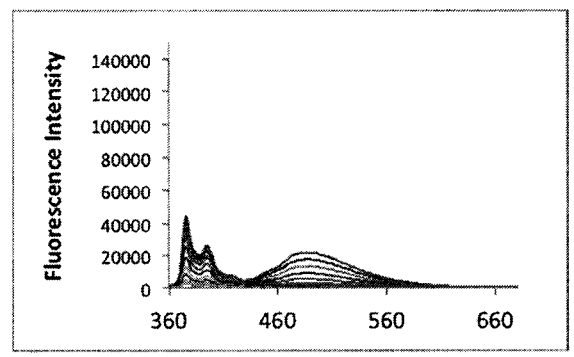
FIG. 4 is emission spectra of a binding solution in one embodiment of the disclosure for (A) a pY peptide and (B) buffer.
Figure 4:
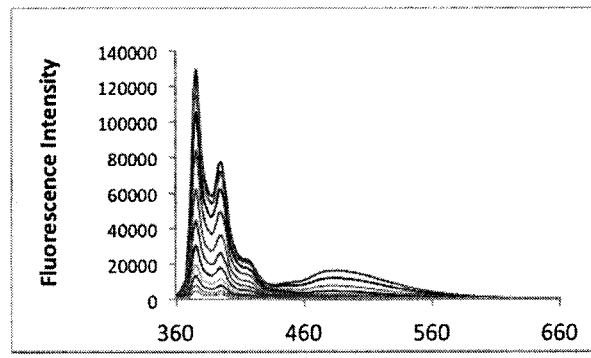

Compound 1-$Zn^{2+}$ and peptides (2:1 constant ratio) were serially diluted from 250 to 3 μM peptide concentration. The fluorescence intensity was measured upon excitation at 350 nm at 2 nm steps. The resulting emission spectra are shown in FIG. 4. Emission spectra for pYpY are presented in FIG. 2A.

The maximum excimer signal resulted from a 2:1 excimer compound:peptide complexation stoichiometry (FIG. 2B). Consistently, upon addition of excess peptide, reduction in signal was observed, corresponding to a shift in the equilibrium toward a 1:1 complex. Association of the excimer forming fluorophore with the pYpY peptide was also found to be highly cooperative ($n_{Hill}$=3.2±0.2; log $K_{app.}$=4.3±0.1 $M^{-1}$). It was also possible to observe this selective response by standard fluorescence imaging, further broadening the utility of the sensor (FIG. 2C).

Figure 5:
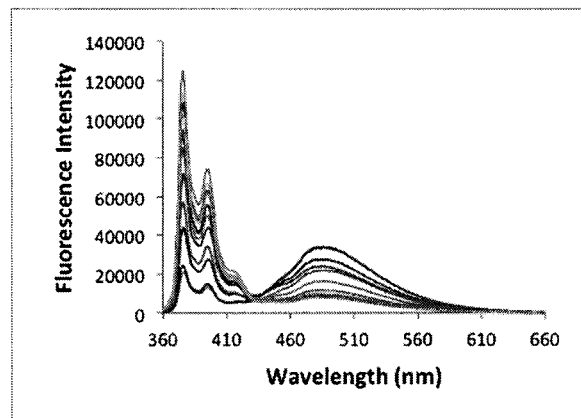
FIG. 5 is emission spectra of a binding solution in one embodiment of the disclosure containing 220 µM of compound of the Formula Ia titrated with 0.2 to 440 µM (A) pYpY peptide, (B) buffer and (C) pY peptide.
Figure 5:
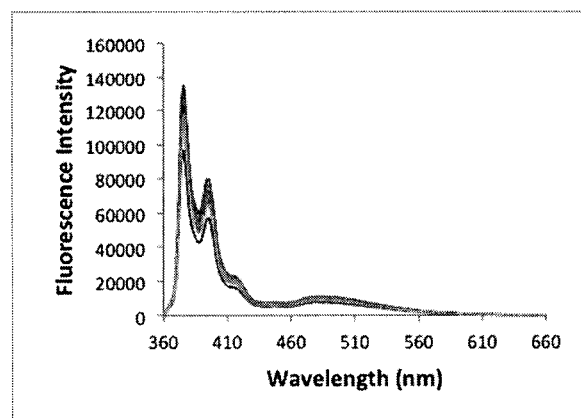
Figure 5:
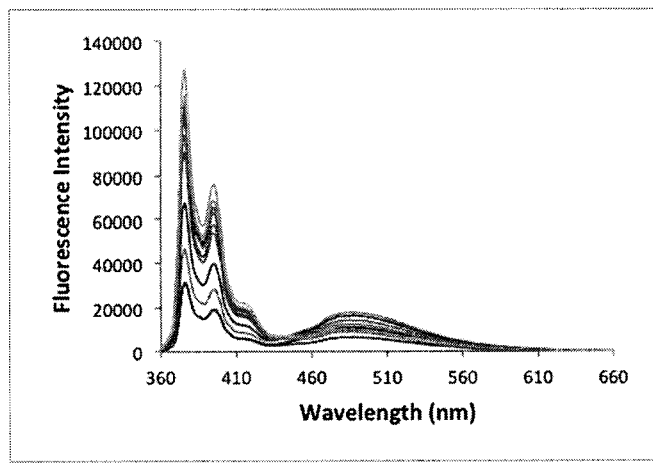

Titration experiments were performed at a constant concentration of compound (220 μM) and concentration of peptides was varied from 0.2 to 440 μM. Fluorescence emission spectra are presented in FIG. 5.

Figure 6:
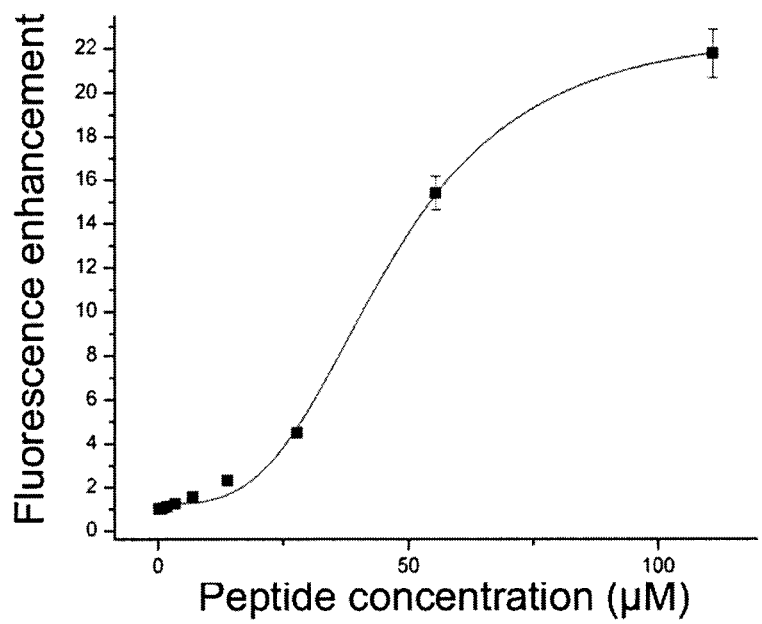
FIG. 6 is pYpY titration data points fit in Origin software using Hill equation.

Fluorescence enhancement values for pYpY peptides were plotted against peptide concentration and fit using Hill equation in Origin software (FIG. 6, from which the hill coefficient and apparent dissociation constants were derived.

Example 3

Protein Studies: Serial Dilution Fluorescence Intensity Measurements

30 μM compound-$Zn^{2+}$ and 10 μM proteins were incubated for 30 min and serially diluted (2:1) to 1 μM protein concentration. At all concentrations fluorescence intensity was measured upon excitation at 350 nm and fluorescence enhancement factors were calculated. The plot is presented in FIG. 3A.

Figure 3:
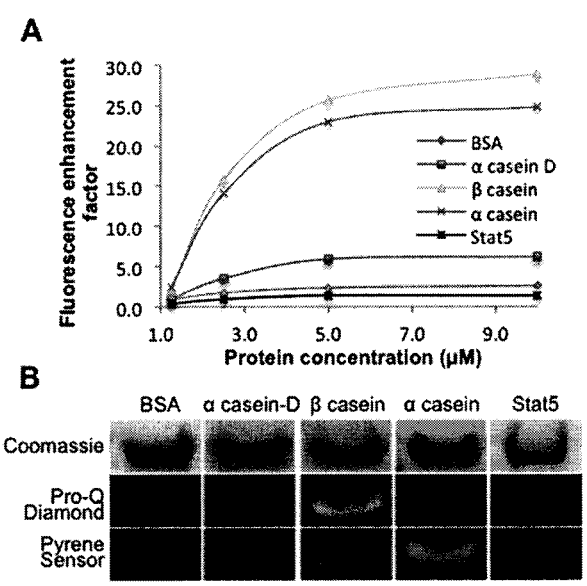
FIG. 3 is (A) a graph demonstrating the fluorescent response of a binding solution in one embodiment of the disclosure to the target proximally phosphorylated and off-target distally phosphorylated and non-phosphorylated proteins in HEPES buffer; and (B) stained polyacrylamide gels.

While initial experiments demonstrated the efficacy of the compound in a model system, it was next sought to probe whether it could retain selectivity for the target di-phosphorylated motifs within full-length proteins. Thus, a selection of variably phosphorylated proteins (Table 1) were incubated with the compound 1-$Zn^{2+}$ at a range of concentrations (1-10 μM of protein) in aqueous solution and assessed for excimer fluorescence enhancement. The results of this experiment are illustrated in FIG. 3A.

TABLE 1

Phosphorylation motifs of proteins selected for treatment with compound 1.

| Protein | Phosphorylation motif |
| --- | --- |
| BSA | No phosphorylation |
| α-casein-D | 2 pS residues; motif unknown |

TABLE 1-continued

Phosphorylation motifs of proteins selected for treatment with compound 1.

| Protein | Phosphorylation motif |
| --- | --- |
| β-casein | pSLpSpSpS |
| α-casein | pSEpS, pSIpSpSpS |
| Stat5 | 3 distal pY residues |

For non-phosphorylated BSA protein, no significant excimer formation was observed, indicating limited non-specific binding to non-phosphorylated protein surfaces (FIG. 3A). Excimer formation was also not induced upon incubation with Stat5 protein (containing three distal phosphorylated residues). These results correlate with the hypothesis and the initial peptide studies. Importantly, for α- and β-casein, which both contain di-phosphorylated motifs, there was observed an almost 30-fold fluorescence enhancement, suggesting that the sensor solution (a binding solution of the disclosure) is selective for proximal di-phosphorylated sites. Dephosphorylated α-casein (α-casein-D) was also tested which, while partially dephosphorylated, is known to retain two phosphorylated residues,[5] but their relative spatial arrangement is unknown. As can be seen, the data suggests that these two phosphate esters might be relatively close in proximity, as indicated by a 5-fold increase in excimer formation.

Example 4

Figure 7:
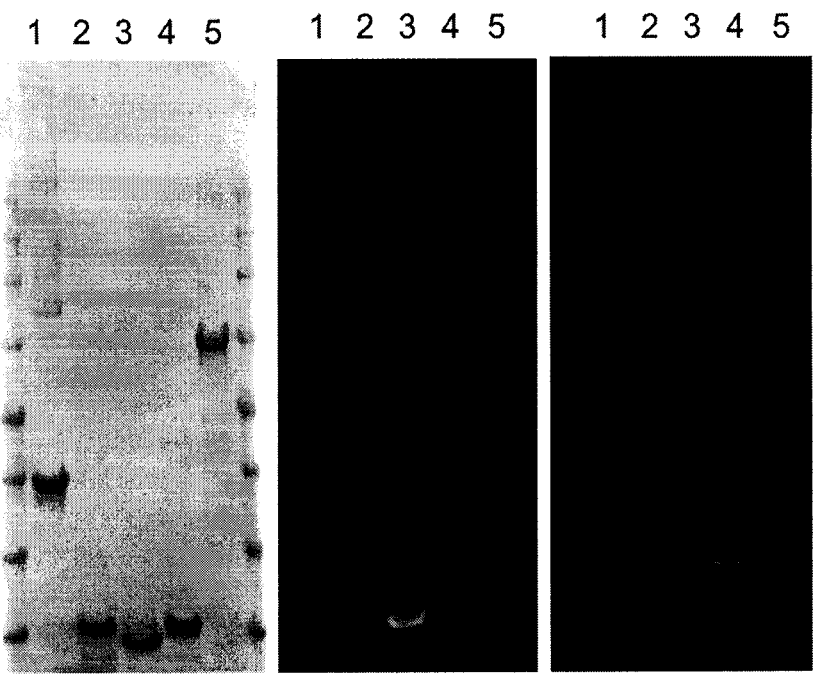
FIG. 7 shows gels stained with (A) Coomassie Blue, (B) Pro-Q Diamond and (C) a binding solution in one embodiment of the disclosure. Lanes 1-5 correspond to BSA, α casein-D (D=dephosphorylated), β casein, α casein and Stat5, respectively.

Protein Studies: Gel Experiments 1.2 μg of each protein was loaded in each well in triplicate. Gels were run at 100 V/75 mA for 50 min. One part of the gel was stained with Coomassie Blue for 1 h and destained for 1 h according to the general protocols. The second part of the gel was stained with the Pro-Q Diamond according to the supplier's protocol. The last part of the gel was fixed for 40 min and stained in 300 μM solution of the sensor (a binding solution of the disclosure) for 40 min. The gel was then rinsed with 40% acetonitrile/sodium acetate buffer (pH 4.2) and imaged under UV light. Representative imaged gels are shown in FIG. 7.

Since proteins are, in the prevailing majority of studies, detected by staining following separation on polyacrylamide gels, the utility of the sensor was next examined in this medium. Briefly, on the same polyacrylamide gel, approximately equal amounts of proteins (1.2 μg, ≈50 pmols) were run and stained with the universal Coomassie Blue protein stain (FIG. 3B, top row). To determine the relative levels of total protein phosphorylation, the gel was stained with the Pro-Q Diamond stain. As expected, staining of non-phosphorylated BSA protein with Pro-Q Diamond was negligible. While phosphorylated Stat5, α-casein and α-casein-D exhibited comparable phosphorylation levels, β-casein was stained to a greater extent. Gels were then treated with a solution of compound 1-$Zn^{2+}$ as follows. The gel was fixed for 40 min in a solution of 50% methanol/10% acetic acid in water and then incubated in a solution of 300 μM compound for 40 min and rinsed with acidic sodium acetate-acetonitrile buffer. Gels were then imaged with a BIORAD ChemiDoc MP fluorescent imaging system.

Figure 8:
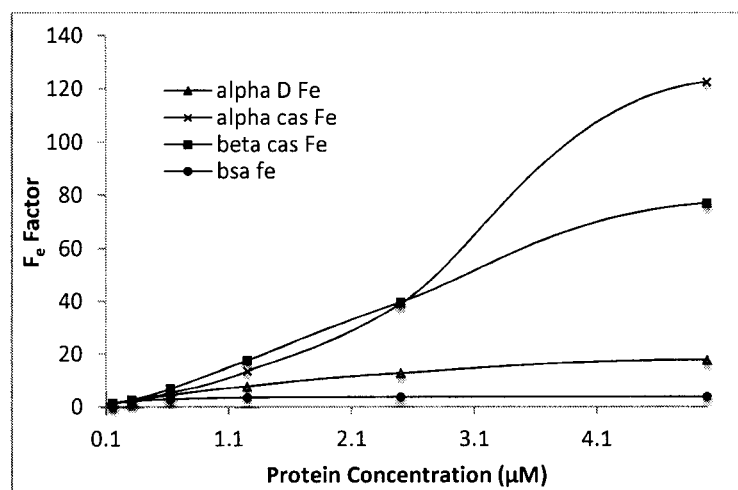
FIG. 8 shows titration of a binding solution in one embodiment of the disclosure with protein from 60 nM to 5 µM.

Proteins possessing proximally phosphorylated residues were selectively detected over the non-phosphorylated BSA at concentrations as low as 300 nM. The difference between the number of proximally phosphorylated sites (1 in dephosphorylated α-casein, multiple in α-casein and β-casein) was detected at concentrations as low as 600 nM (FIG. 8).

Figure 9:
FIG. 9 shows α-casein stained with a binding solution in one embodiment of the disclosure on a polyacrylamide gel. Amount of protein loaded is labeled in μg.

The lowest detection limit of proximally phosphorylated site using a compound 1-$Zn^{2+}$ is 0.6 μg of protein (FIG. 9).

Figure 10:
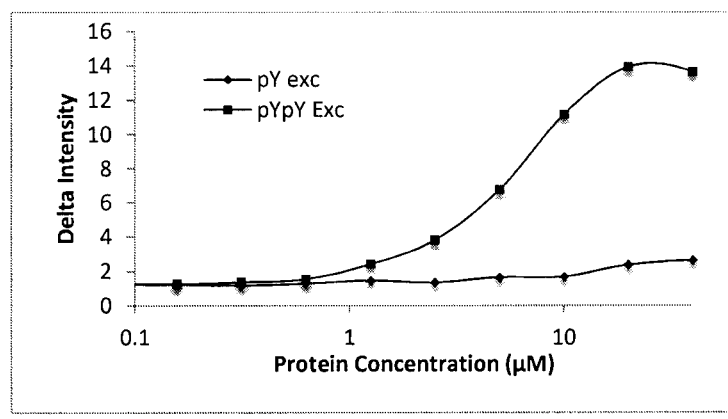
FIG. 10 shows titration of a binding solution in one embodiment of the disclosure with pY and pYpY peptides from 60 nM to 40 μM.

Proximally phosphorylated peptide can be detected over mono-phosphorylated ones at concentrations as low as 600 nM (FIG. 10).

As expected, the BSA band was negligibly stained by both Pro-Q Diamond and compound 1-$Zn^{2+}$. Differential staining of STAT5 (bearing distal pY motifs) by Pro-Q Diamond and compound 1-$Zn^{2+}$ was observed: compound 1-$Zn^{2+}$ did not stain the Stat5 band, which was detected by Pro-Q Diamond. This data strongly suggested that compound 1-$Zn^{2+}$ does not form excimers with mono-phosphorylated protein motifs. In addition, compound 1-$Zn^{2+}$ more intensely stained α-casein over β-casein, despite the higher total phosphorylation of the latter (as determined by Pro-Q Diamond). This observation further supported the hypothesis, since α-casein has an additional di-phosphorylated site (Table 1), and would therefore facilitate increased excimer formation per protein molecule. As can be seen, the distinct pattern of staining by compound 1-$Zn^{2+}$ relative to that of Pro-Q Diamond, strongly suggest that compound 1-$Zn^{2+}$ is selective for di-phosphorylated protein motifs. Owing to its unique excimer turn-on mechanism, stained gels have essentially no background fluorescence and therefore do not require de-staining, making it possible to complete an entire protocol in under 1.5 hours.

Figure 11:
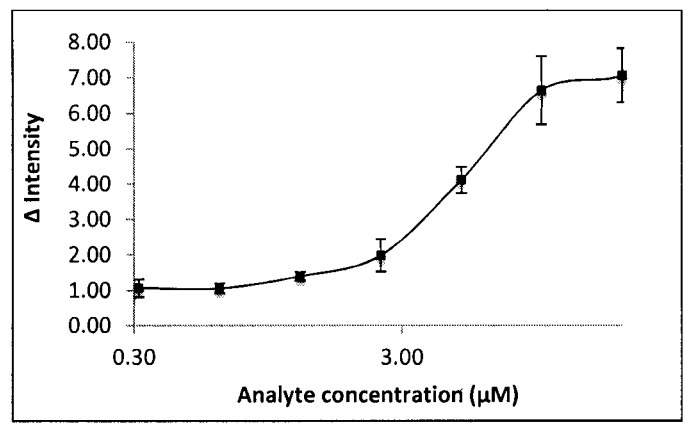
FIG. 11 shows titration of a binding solution in one embodiment of the disclosure with varying concentrations of PPi.
Figure 12:
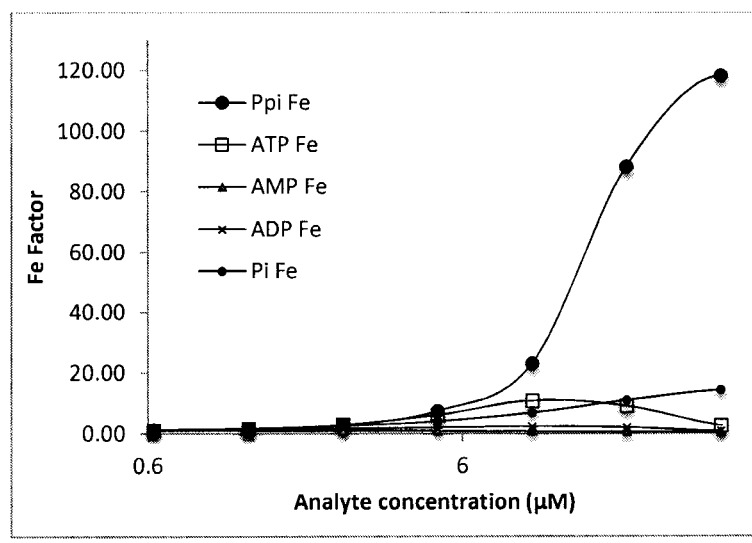
FIG. 12 shows titration of a binding solution in one embodiment of the disclosure with varying concentrations of small phosphorylated molecules (30 nM to 80 μM)

Solution containing compound 1-$Zn^{2+}$, a binding solution of the disclosure, also detects pyrophosphate (PPi) at concentrations as low as 1 μM (FIG. 11). Pyrophosphate can be selectively detected over other phosphorylated nucleotides and orthophosphate at concentrations above 10 μM (FIG. 12).

In conclusion, the present inventors have demonstrated a turn-on dual emission fluorescent sensor specific to phosphorylated protein sites (such as di-phosphorylated sites) with demonstrated utility for both solution and gel-based fluorescent detection techniques.

Example 5

In-Situ Vs Pre-Metallation

Cyclen-metal complexes were generated as described in Example 1.1c and stored at −20° C. as lyophilized powder, which can be dissolved in the buffer of choice prior to experiment. Alternatively, metallation was performed in situ, by combining equimolar amounts of the pre-metallated precursor (e.g. compound 1) and metal ion salt.

Figure 13:
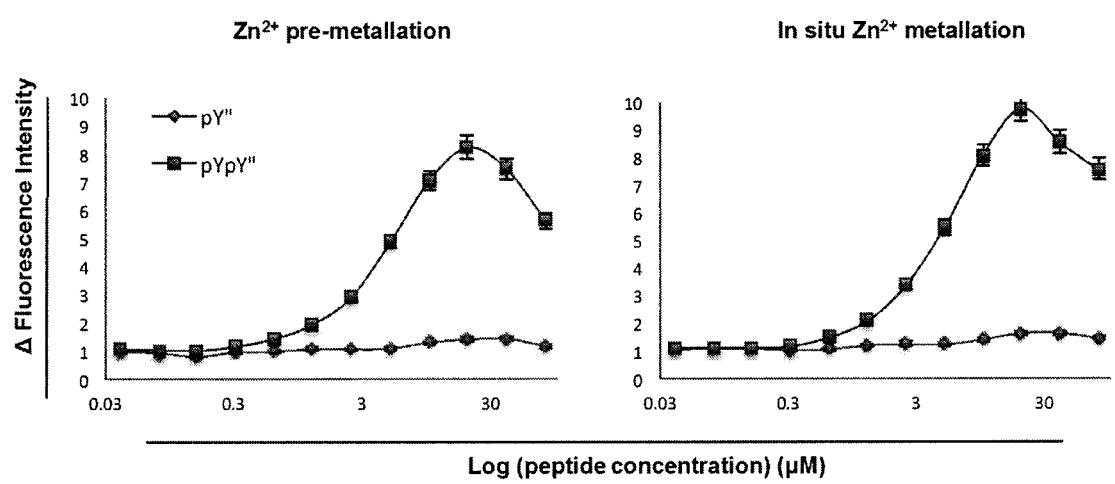
FIG. 13 shows titration of a binding solution I (right) and Ia (left) in one embodiment of the disclosure with varying concentrations of pY and pYpY peptides of 40 μM.

In one example 40 μM of compound 1 pre-metallated with zinc(II) triflate (referred to as "$Zn^{2+}$ pre-metallation" in FIG. 13; procedure described in example) was titrated with 80-0.04 μM of pY and pYpY peptides in 50 mM HEPES pH 7.5, 5% DMSO. In another example, 40 μM of compound 1 was dissolved in 50 mM HEPES pH 7.5, 5% DMSO, which contained 40 μM of zinc(II) triflate (referred to as "in situ $Zn^{2+}$ metallation" in FIG. 13) and was titrated with 80-0.04 μM of pY and pYpY peptides. Fluorescence measurements were performed as described in Example 2. As can be seen from FIG. 13, no significant difference in the titration curves was observed between the two different metallation procedures.

Example 6 pY and pYpY Conditions for Detection of Proximally Phosphorylated Peptides

Figure 14:
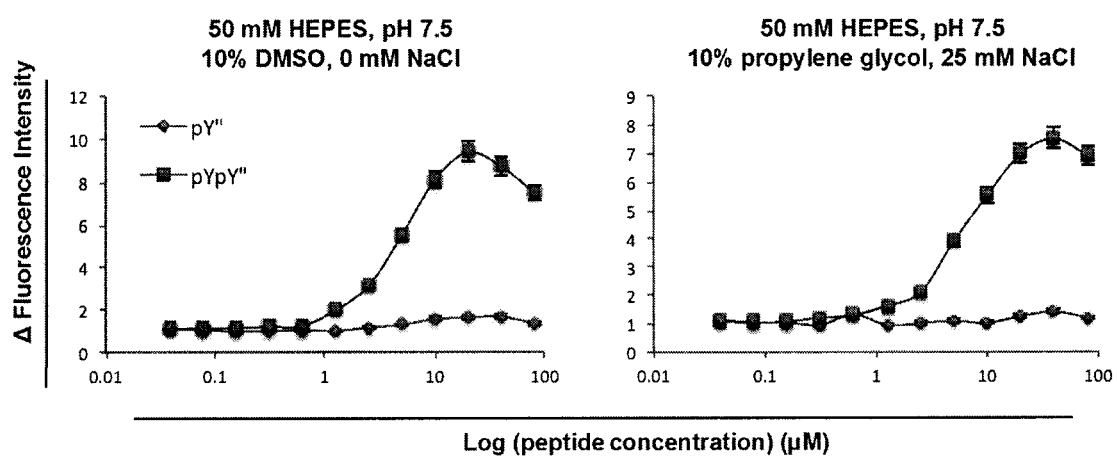
FIG. 14 shows titration of a binding solution in one embodiment of the disclosure with varying concentrations of pY and pYpY peptides in aqueous buffers of variable composition.

Various conditions for the detection of proximally phosphorylated peptides and proteins in aqueous solution are shown in Table 1. For the screens, analytes (peptides) were dissolved in a specific buffer at various concentrations (normally 100 μM to 40 nM), and combined with 40 μM of compound 1 in complex with $Zn^{2+}$ (triflate salt) dissolved in the same buffer on a 384 well flat bottom black plate. The mixture was incubated for 20 minutes and fluorescence emission intensity at 476 nm (10-20 nm bandwidth) was measured using a Tecan M1000 microplate reader, upon excitation at 350 nm (5 nm bandwidth) at 400 Hz. The different conditions tested were assessed based on the ratios of signal intensity of positive to negative control analytes and signal intensity in general. FIG. 14 shows conditions for the detection of proximally phosphorylated peptides in aqueous solutions, in which single digit μM detection limits for a single proximally phosphorylated site were achieved (7.5, 50 mM HEPES, 25 mM NaCl, 10% propylene glycol and pH 7.5, 50 mM HEPES, 10% DMSO).

Example 7

Detection of Proximally Phosphorylated Peptides Using Compound 1-$Zn^{2+}$

Figure 15:
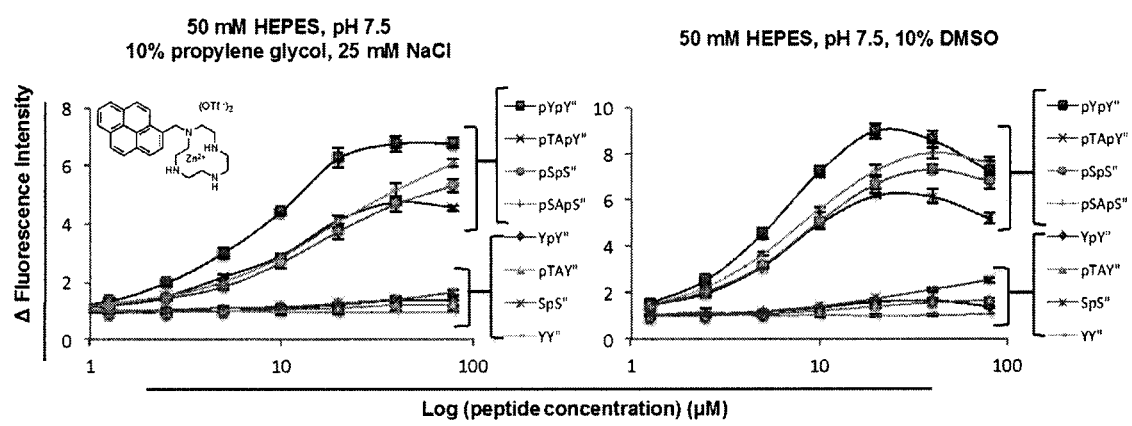
FIG. 15 shows titration of a binding solution in one embodiment of the disclosure with varying concentrations of proximally phosphorylated target peptides and mono-phosphorylated or non-phosphorylated off-target peptides in aqueous buffers of variable composition.

The detection of proximally phosphorylated peptides using compound 1 in complex with $Zn^{2+}$ (triflate salt) was comparable under the two tested conditions: pH 7.5, 50 mM HEPES, 25 mM NaCl, 10% propylene glycol and pH 7.5, 50 mM HEPES, 10% DMSO (as shown in FIG. 15).

Figure 16:
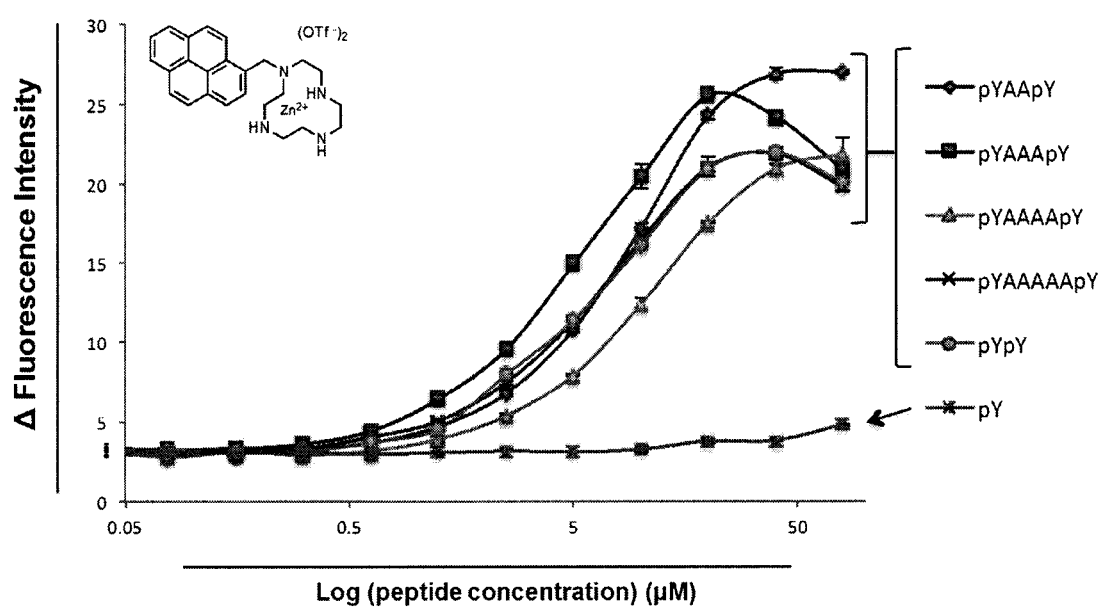
FIG. 16 shows titration of a binding solution in one embodiment of the disclosure with varying concentrations of proximally phosphorylated target peptides and mono-phosphorylated off-target peptides.

Peptides containing two phosphotyrosine residues, spaced by 2-5 alanine residues, were titrated into 40 μM solution of compound 1 in complex with $Zn^{2+}$ (triflate salt) (pH 7.5 50 mM HEPES, 10% propylene, 25 mM NaCl) from 80 μM to 40 nM (FIG. 16). Y-axis is Δ Fluorescence Intensity as defined by the formula in example 2.

This example demonstrates that compound 1 in complex with a metal ion (in this example $Zn^{2+}$ as the triflate salt) is able to recognize all most commonly proximally-phosphorylated sites including those on serine, tyrosine and threonine residues (see FIG. 15). Mono-phosphorylated or non-phosphorylated peptides did not produce a significant signal. Error bars represent +/− s.d. Fluorescence measurements were performed as described in example 6. Full peptide sequences can be found in Materials and Methods.

Example 8

Detection of Proximally Phosphorylated Peptides Using Compounds 1, 9, 14 and 15

Figure 17:
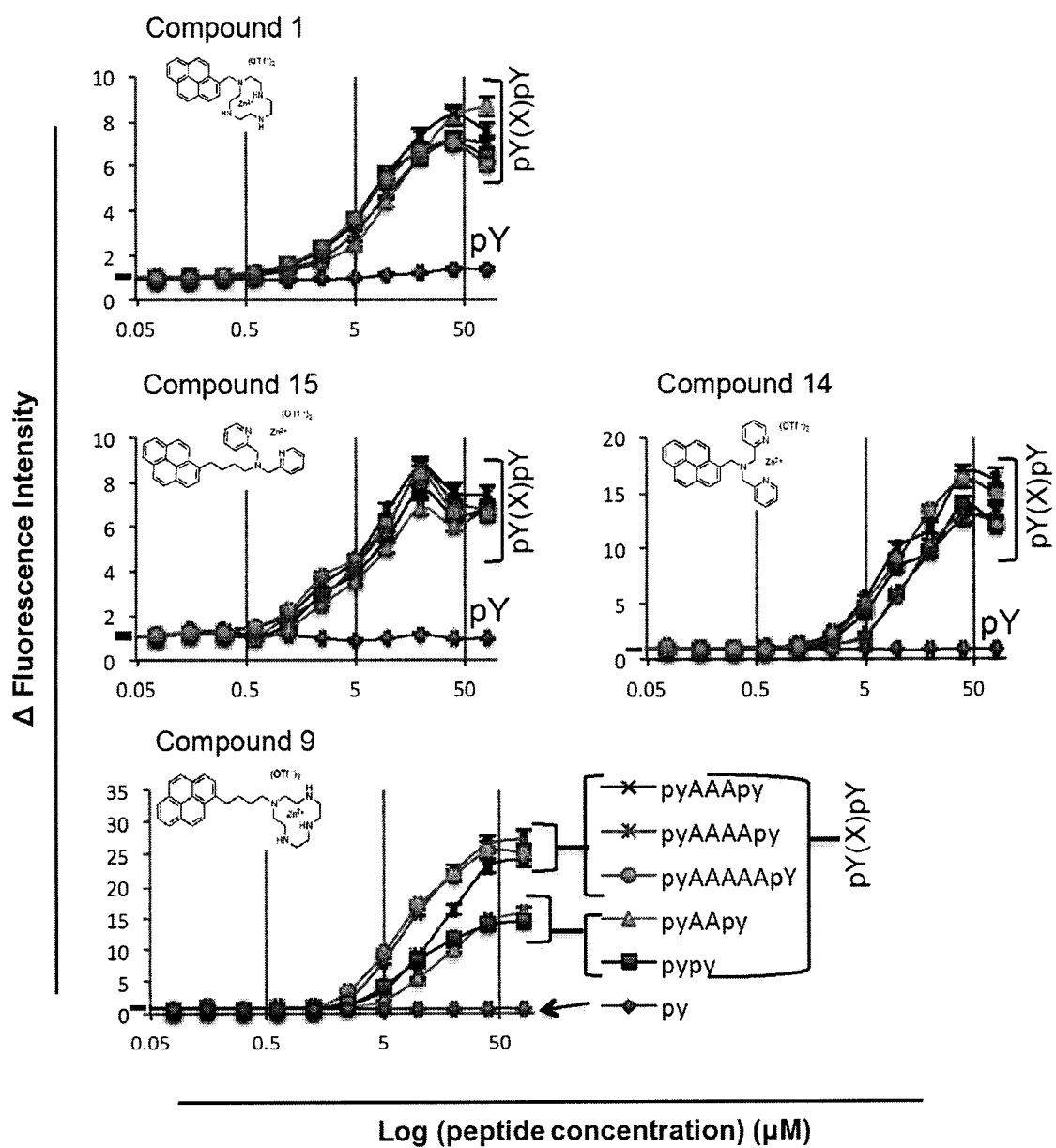
FIG. 17 shows titration of a binding solution in one embodiment of the disclosure with varying concentrations of proximally phosphorylated target peptides and mono-phosphorylated off-target peptides.

Using the same methods as described in Example 6, $Zn^{2+}$ (triflate salt) complexes of compounds 1, compound 9, compound 15, compound 14 were tested in pH 7.5, 50 mM HEPES, 25 mM NaCl, 10% propylene glycol. The results of the experiment are shown in FIG. 17.

DISCUSSION

The difference between compounds 1 and 9 is the length of the linker between the fluorophore and the metal-coordinating moiety. The linker in the compound 9 is three carbons longer, and therefore, sensitivity of compound 9 is increased for the peptides in which the two phosphorylated tyrosine residues are more spaced out. These results also demonstrate that dipicolylamine and cyclen groups are suitable for the detection of proximally phosphorylated sites.

Example 9

Detection of Proximally Phosphorylated Peptides pY and pYpY Using Compounds 1 and 12

Using the same methods as described in Example 6, $Zn^{2+}$ (triflate salt) complexes of compound 1 and compound 12 were tested in pH 7.5, 50 mM HEPES, 5% DMSO. The results of the experiment are shown in FIG. 18.

Figure 18:
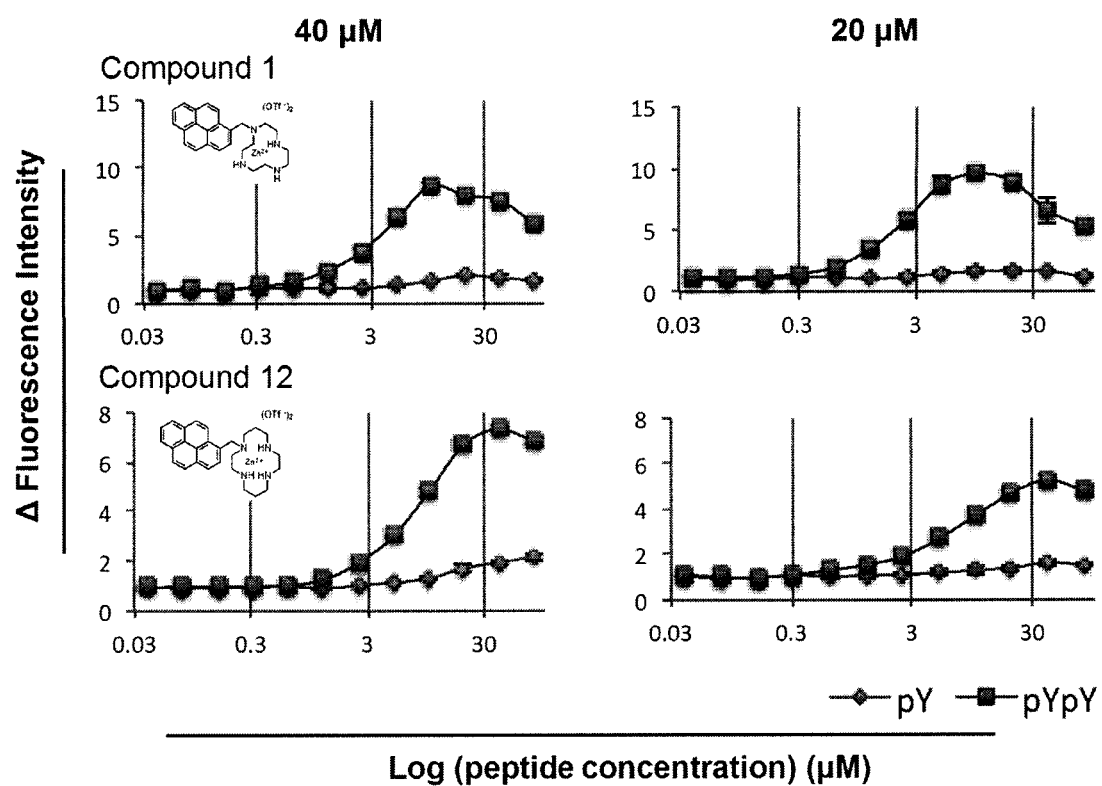
FIG. 18 shows titration of a binding solution in one embodiment of the disclosure with varying concentrations of pYpY and pY peptides.

FIG. 18 demonstrates that compound 12, bearing a cyclam metal-chelating moiety, in complex with $Zn^{2+}$ (triflate salt) is potent at detecting proximally phosphorylated peptides.

Example 10

Detection of Proximally Phosphorylated Peptides pY and pYpY Using Compounds 1 and 12

Figure 19:
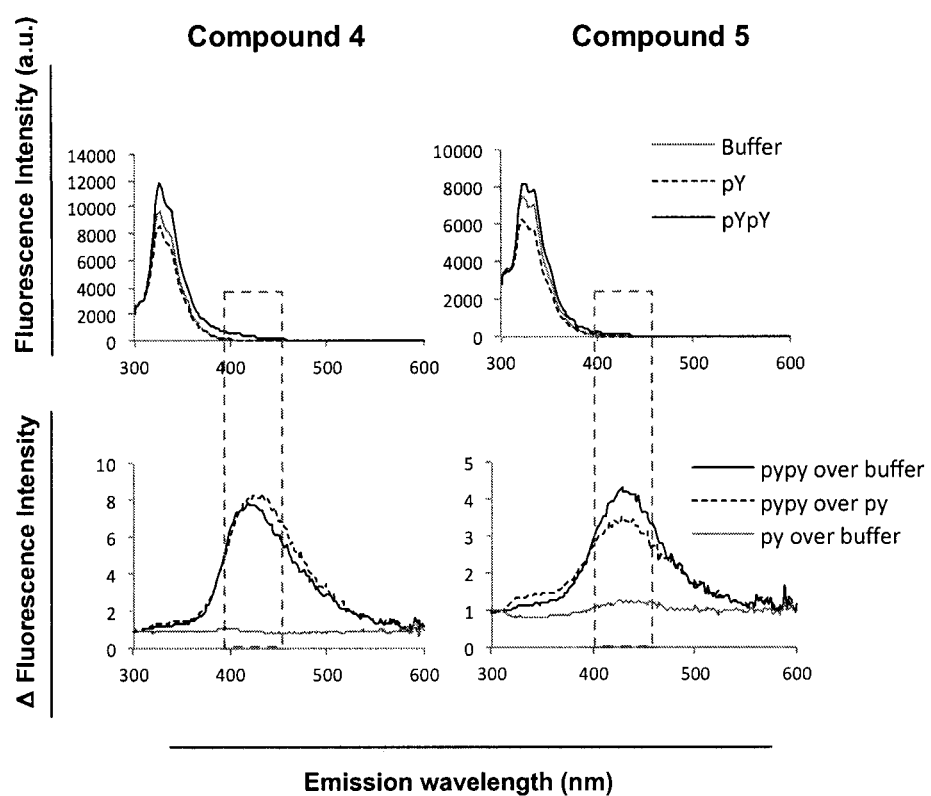
FIG. 19 shows (top panel) fluorescence emission spectra of a binding solution in one embodiment of the disclosure without peptides or in the presence of pY and pYpY peptides and (bottom panel) same spectra represented as ratios.

Non-pyrene excimer forming derivatives (compounds 4-7) were synthesized and assessed for their ability to sense proximally phosphorylated peptides. All experiments for these derivatives were performed in pH 7.5 50 mM HEPES, 10% DMSO. 125 µM pY and pYpY peptides were combined with 250 µM of compounds 4, 5 and 6 ($Zn^{2+}$ triflate complexes), or buffer as background control, and the solution was irradiated at 290 nm and fluorescence emission scan was recorded. The resultant fluorescence emission spectra are shown in FIG. 19 (top panel). No distinct peak corresponding to excimer emission in response to pYpY peptide was observed. However, when pYpY spectra were divided by those of pY or buffer control (FIG. 19 bottom panel), a distinct peak in the 420 nm region was observed for both naphthyl derivatives (compounds 4 and 5). These peaks indicate that the spike in response to the addition of pYpY corresponds to excimer formation, since 420 nm region corresponds to a roughly 100 nm shift from the monomer emission maximum (approximately at 330 nm).

pY and pYpY peptides were titrated into 250 µM of compound 4 in complex with $Zn^{2+}$ (triflate salt) in pH 7.5 50 mM HEPES, 10% DMSO. The resulting titration curve is displayed in FIG. 20. As can be seen, the pYpY peptide is selectively detected over the pY peptide with the detection limit of single-digit µM (this titration curve was generated using fluorescence point emission and not integration; 250 µM sensor was used). Time-resolved experiments were also conducted, where the delay time prior to acquisition of fluorescence was varied (0, 5, 10, and 15 µs; FIG. 21). In this case, the concentration of compound 4 in complex with $Zn^{2+}$ (triflate salt) was constant at 40 µM. It can be seen that even with 15 µs delay time, the signal selectivity towards pYpY was retained, indicating that the fluorescent species is long-lived, which is consistent with the excimer mechanism. Consistent with the long-lived fluorescent species resultant of association with pYpY, increased integration time of the fluorescence signal yields slight enhancements in [pYpY: buffer] ratios (FIG. 22 left panel). pYpY-selective signal was slightly improved upon narrowing the detection of fluorescence at 420 nm to 10 or 5 nm bandwidth as compared to the original 20 nm.

pY and pYpY peptides were also titrated into 250 µM of compound 5 in complex with $Zn^{2+}$ (triflate salt) in pH 7.5, 50 mM HEPES, 10% DMSO. The fluorescence emission spectra (FIG. 23) indicate a pYpY-selective enhancement in the excimer region of the fluorophore. The titration curve is displayed in FIG. 24. As can be seen, the pYpY peptide is selectively detected over the pY peptide with the detection limit of single-digit µM.

Example 11

In-Solution Detection of Small Phospho-Anions

40 µM of compound 1 in complex with $Zn^{2+}$ (triflate salt) was incubated with various concentrations of ATP, ADP, AMP, PPi and Pi (20-0.04 µM) in pH 7.5, 50 mM HEPES, 5% DMSO. The complex was incubated for 20 min and fluorescence intensity was measured in two regions: 366-386 and 466-486 nm, corresponding to the monomer and excimer regions of compound 1-$Zn^{2+}$, respectively. Fluorescence enhancement factor and Δ fluorescence intensity were calculated and the results are presented in FIG. 25. As can be seen, PPi can be selectively detected when the signal is analyzed using the Fluorescence enhancement formula but not the Δ fluorescence intensity. Similar results were observed with compound 12-$Zn^{2+}$, in which the experiment was performed under identical conditions as described for compound 1-$Zn^{2+}$, the results of which are shown in FIG. 26.

Example 12

In-Solution Detection of Proteins Using Compound 1

Non-phosphorylated (BSA and lysozyme) and distally phosphorylated negative control proteins (ovalbumin) were used in detection methods for in-solution, on gel and on blot applications. Dephosphorylated α-casein (D-α-casein), β-casein and α-casein served as proximally phosphorylated positive controls (see Table 2). The phosphosites presented in Table 2 were obtained from the PhosphoSitePlus database or a UniProt database.

Various conditions for the detection of proximally phosphorylated proteins and proteins in aqueous solution are shown in Table 3. Proteins were dissolved in a buffer at various concentrations (normally 100 µM to 40 nM), and combined with 40 µM of compound 1 in complex with $Zn^{2+}$ (triflate salt) dissolved in the same buffer on a 384 well flat bottom black plate. The mixture was incubated for 20 minutes and fluorescence emission intensity at 476 nm (10-20 nm bandwidth) was measured using a Tecan M1000 microplate reader, upon excitation at 350 nm (5 nm bandwidth) at 400 Hz. The different conditions tested were assessed based on the ratios of signal intensity of positive to negative control analytes and signal intensity in general. Among the parameters assessed in this study and using these specific control proteins, the following conditions were selected for proteins studies: pH 5.5 50 mM NaOAc, 50 mM NaCl, 5% DMSO (see FIG. 27). Using these conditions, detection limits of low nM to single-digit µM were achieved, dependent on the number of proximally phosphorylated sites. Depending on the number of proximally di-phosphorylated sites, lower detection limits could be achieved by using lower concentration of a sensor.

Example 13

In-Solution Detection of Proteins Using Compounds 1, 9, 14 and 15

Using same methods as described in Example 1.1c, $Zn^{2+}$ (triflate salt) complexes of compounds 1 (top left), compound 9 (top right), compound 15 (middle left), and compound 14 (middle right) were tested in pH 7.5, 50 mM HEPES, 75 mM NaCl, 20% DMSO (see FIG. 28). Compounds 1, 9, 14 and 15 all demonstrated comparable efficiency at detecting the proximally phosphorylated proteins (α-casein, β-casein and D-α-casein).

Example 14

In-Solution Detection of Proteins Using Compounds 1 and 12

Using same methods as described in Example 14, 40 and 20 μM of $Zn^{2+}$ (triflate salt) complexes of compound 1 (top) and compound 12 (bottom) (FIG. 29), were tested in pH 7.5, 50 mM HEPES, 5% DMSO.

Using same methods as described above, 60, 40, 20 and 10 μM of $Zn^{2+}$ (triflate salt) complexed with compound 12 (FIG. 30), were titrated with 80-0.04 μM of proteins in pH 7.5, 50 mM HEPES, 5% DMSO. The resulting titration curves are demonstrated in FIG. 31. As can be seen, by lowering the concentration of the sensor, the detection limit of the system was improved.

Example 15

In-Solution Detection of Phosphatase Substrates Using Compounds 1 and 12

1 μL of alkaline phosphatase (Sigma Aldrich, cat: P6774) was dissolved in 25 μL of 10 mM Tris pH 8.0, 1 mM $MgCl_2$. 2 μL of diluted phosphatase was combined with 100 μL of 11.25 μM analyte protein and incubated at 37° C. for 30 min. 30 L of the each of the treated proteins were combined with 30 μL of the compound 1 in complex with $Zn^{2+}$ (triflate salt) in pH 7.5 50 mM HEPES, 5% DMSO, to provide a final sensor concentration of 40 μM. As can be seen from FIG. 31, following treatment with phosphatase, signal of the proximally phosphorylated protein has been decreased significantly, which indicates that this sensory system is phosphate-dependent. Additionally, this experiment demonstrates that this sensor can be used for the identification of phosphatases, which are capable of de-phosphorylation on proximal residues. Therefore, this sensor can also be used for the identification of substrates for kinases, which are capable of phosphorylation on neighboring residues.

Example 16

On-Gel Detection of Proximally Phosphorylated Protein

Gel Electrophoresis: Control Proteins 15 well 15 μl Mini-PROTEAN Precast Gel (Bio-Rad, cat. 456 1086) or 26 well 15 μl Criterion TGX Precast gel (Bio-Rad, cat. 567-1085) were used for control protein studies BSA (Sigma Aldrich, cat. A7030-10G), ovalbumin (Sigma Aldrich, cat. A5503-1G), β-casein (Sigma Aldrich, cat. C6905-250MG) and lysozyme (Sigma Aldrich, cat. L6876-1 G) were used as control proteins. For loading onto the gel, proteins were dissolved in 1×PBS and combined 2:1 with Native Sample Buffer (Bio-Rad, cat. 1610738). Each lane contained equal amounts of each of the four proteins. For the determination of detection limits protein amounts tested were 1, 0.5, 0.25 and 0.125, 0.063 and 0.031 μg per protein per lane. Each gel also contained BLUeye Prestained Protein Ladder (GeneDirex, cat. PM007-0500). The gel was run in 1×Tris/Glycine/SDS Buffer (Bio-Rad, cat. 161-0732) at 110-150 V until the bromophenol blue band ran off the gel.

Following separation of the mixture of the four proteins, gel was fixed in 25 mL of 50% methanol (MeOH), 10% acetic acid (AcOH)) 2×30 min. Gel was washed in 25 mL of MilliQ water 3×10 min and then stained with 25 mL of 100 μM of compound of this disclosure in pH 5.5 50 mM sodium acetate (NaOAc), 5% dimethyl sulfoxide (DMSO), 25 mM sodium chloride (NaCl) for 1 h protected from light. Gel was washed in 25 mL of MilliQ water 3×5 min and imaged on a Bio-Rad ChemiDoc MP using UV Trans illumination and 530/28 emission filter. Alternatively, gels can be visualized under trans-UV illumination.

Following acquisition of image after staining of a gel with compounds of the disclosure, gel was de-stained in 25 mL of 2×PBS, 20% DMSO 3×20 min and then washed with 25 mL of MilliQ water 3×5 min to remove a binding solution of the disclosure. The gel was then stained with Pro-Q Diamond Gel Stain (Life Technologies, cat. P33300), and imaged according to the manufacturer's protocol.

Subsequent staining by SYPRO Ruby Gel Stain Solution (Life Technologies, cat. S12000) and imaging was performed according to the manufacturer's protocol.

Compound 1

Compound 1 in complex with $Zn^{2+}$ (triflate salt) was used to identify conditions for detecting proximally phosphorylated proteins directly on polyacrylamide gels. The final conditions used are described above. These conditions afforded a detection limit of at least 250 ng for β-casein protein (see FIG. 32), over BSA, ovalbumin and lysozyme proteins. Due to the turn-on mechanism of compound 1 in complex with $Zn^{2+}$ (triflate salt), essentially no de-staining steps are required, facilitating shorter protocol times and milder conditions (2.5 h including fixation of the gel). Lane profile analysis was performed on the gel, which is also shown in FIG. 32. According to the analysis, at 0.5 μg of each protein the signal for proximally phosphorylated β-casein is around 5.5 fold stronger as compared to the distally phosphorylated ovalbumin or non-phosphorylated BSA.

Example 17

Detection of Proximally Phosphorylated Protein—MS Compatability

For additional analysis of the gels stained with compound 1 in complex with $Zn^{2+}$ (triflate salt) (FIG. 32), additional studies were developed which would allow more extensive characterization of the sample under investigation. The non-covalent nature of compound 1 in complex with $Zn^{2+}$ (triflate salt) and mild protocol conditions permitted destaining of the gel from compound 1 in complex with $Zn^{2+}$ (triflate salt), and subjecting it to analysis for total phosphorylation and total protein content by commercially available stains, Pro-Q Diamond and SYPRO ruby, respectively (see FIG. 33; methods are described in example 16 and in following paragraphs). As a result of this three-way multiplex analysis, which can be completed in under 15 h, one can distinguish among proximally-, distally- and non-phosphorylated proteins as exemplified in (FIG. 33).

1 μg of each of the BSA, ovalbumin, α-casein, dephosphorylated α-casein, and β-casein were separated on a polyacrylamide gel and stained with compound 1 in complex with $Zn^{2+}$ (triflate salt) as described in example 16. Staining with compound 1 in complex with $Zn^{2+}$ (triflate salt) demonstrates that both β-casein and α-casein are proximally phosphorylated, which is consistent with literature (see Table 2). Dephosphorylated α-casein, which is known to retain two residues[12] was also detected, indicating its proximal phosphorylation. Compound 1 in complex with $Zn^{2+}$ (triflate salt) was then removed or destained from the gel by incubating the gel in the solution of pH 4.5, 50 mM NaOAc buffer, 5% DMSO overnight, then rinsed with water 3×10 min and the gel was stained with the commercially available Pro-Q Diamond and SYPRO Ruby stains as per the manufacturer's instructions. The results in FIG. 33 demonstrate that the distally phosphorylated ovalbumin protein was detected by the total phosphoprotein stain Pro-Q diamond, but not by compound 1 in complex with $Zn^{2+}$ (triflate salt). Thus, it demonstrates that distally phosphorylated proteins are not detected by compound 1. Additionally, this suggests that staining of the gel with compound 1 in complex with $Zn^{2+}$ (triflate salt) prior to Pro-Q Diamond stain does not interfere with the performance of the latter. Lastly, staining by SYPRO Ruby reveals all five proteins, including the band corresponding to the non-phosphorylated protein BSA, which was not detected by Pro-Q Diamond or compound 1 in complex with $Zn^{2+}$ (triflate salt), suggesting that compound 1 in complex with $Zn^{2+}$ (triflate salt) does not interfere with the SYPRO Ruby stain either.

Mass Spectrometry Analysis:

Following multiplex protocol bands corresponding to α-casein was excised out of the gel under UV lamp and dehydrated with acetonitrile (ACN) at 25° C. for 10 min. ACN was fully removed and the bands were incubated in 300 μl of 10 mM dithiothreitol (DTT, Sigma-Aldrich) in a 50 mM solution of ammonium bicarbonate ($NH_4HCO_3$) for 30 min at 60° C. and cooled to room temperature for 10 min. Following the removal of the DTT solution and another ACN dehydration, the gel bands were incubated in 300 μl of a 100 mM iodoacetamide solution in 50 mM $NH_4HCO_3$ for 45 min at 37° C. in the dark. The gel bands were then dehydrated with ACN and rehydrated by addition of 300 μl 50 mM $NH_4HCO_3$, repeating these steps 3 times. Following the last ACN dehydration step, the gel bands were incubated in 100 μl of 50 mM $NH_4HCO_3$ solution containing 1 μg of sequencing grade modified trypsin (Promega) overnight at 37° C. The digestion solution containing the tryptic peptides was removed and dried by SpeedVac (ThermoFisher Scientific) to completion for 1 h. The dried peptide mixture was re-suspended in 50 μl of 1 M glycolic acid in 80% ACN solution containing 5% trifluoroacetic acid. Phosphopeptides form this mixture were enriched using titanium dioxide ($TiO_2$) Mag Sepharose (GE Healthcare) following the manufacturer's protocol. Eluted phosphopeptides were dried to completion by SpeedVac and resuspended in 40 μl of $H_2O$ with 1% formic acid for use in subsequent MS/MS analysis.

Enriched phosphopeptides were sprayed directly into an LTQ-Orbitrap Velos mass spectrometer (ThermoFisher Scientific) with a CID fragmentation method using a nanospray ion source (Proxeon). Fifteen MS/MS data-dependent scans in centroid mode were acquired simultaneously for each full scan profile mode mass spectrum. The full scan was performed in 60 000 resolution, with MS2 scans performed with 35% collision energy, isolation width of 1 m/z, and 10 ms activation time over scan range from 300 to 1600 m/z. Parent masses with a charge stat of +1 were rejected for MS2. The resulting RAW files were searched with MaxQuant (version 1.5.0.0) under default settings using the ipi.BOVIN.v3.54.fasta protein database. Search parameters were set to allow for two missed cleavage sites. The settings allowed for variable oxidations of methionine residues, N-terminal acetylation, and phosphorylation of STY residues. Cysteine by carbamidomethylation was set as a fixed modification.

Table 4 shows the most prominent fragments identified by MS. Collectively this data confirms that the protein that was analyzed was α-casein. Thus, it has been demonstrated that compound 1 in complex with $Zn^{2+}$ (triflate salt) and the complete multiplex protocols do not interfere with the mass-spectrometry-based identification of protein bands of interest, including analysis of phosphorylation sites as shown in Table 4.

Example 18

On-Gel Detection of Proximally Phosphorylated Protein Using Compound 1

Four proteins BSA, ovalbumin, β-casein and Lysozyme were separated on a polyacrylamide gel, which was then sequentially stained with ProxyPhos, Pro-Q Diamond and SYPRO Ruby (see example 16 and 17 for details). Each well contained equal amounts of the four proteins. The amount of each protein loaded in wells was 1.0, 0.5, 0.25 and 0.125 μg (left to right) (see FIG. 34). The arrow shows the detection limit of compound 1 in complex with $Zn^{2+}$ (triflate salt) on a polyacrylamide gel at 250 ng of the proximally phosphorylated β-casein protein. Subsequent Pro-Q Diamond staining confirmed that ovalbumin is a phosphorylated protein, but not BSA or lysozyme. SYPRO Ruby stain detected all proteins regardless of their phosphorylation status.

FIG. 35 shows over-laid fluorescent images of lane 2 (containing 0.5 μg of each protein) which were acquired following staining with compound 1 in complex with Zn2+ (triflate salt), Pro-Q Diamond and SYPRO Ruby. When bands from the three channels are assigned different colors and overlaid, this results in a color-coded 3-way analysis of the lane. Thus if compound 1 is assigned green color, red for Pro-Q Diamond and blue for SYPRO Ruby, following merging one can visualize proximally phosphorylated proteins in yellow (β-casein), distally-phosphorylated proteins in purple (ovalbumin) and non-phosphorylated proteins in blue (BSA and Lysozyme).

Analysis of the lane containing 500 ng of each of the four proteins was performed. As can be seen all four proteins appear to be stained to similar intensities by SYPRO Ruby, indicating that loading was relatively consistent and all proteins are present on gels at comparable amounts (FIG. 36). Pro-Q diamond staining reveals β-casein as the most intensively stained band (5 phosphates, relative intensity=1), followed by ovalbumin (2 phosphates, relative intensity=0.45), consistent with the literature. Staining with compound 1 in complex with $Zn^{2+}$ (triflate salt) reveals β-casein as the most prominent band indicating that it is the only proximally-phosphorylated protein.

Example 19

On-Gel Detection of Proximally Phosphorylated Protein Using Compound 8

Compound 8 was dissolved in 50 mM NaOAc buffer, pH 4.5, 50 mM NaCl, 10% DMSO and combined with 80, 160 or and 240 μM GaCl₃ solutions. Each gel contained 4 lanes with equal amounts of BSA, ovalbumin (Ova), β-casein (β-cas) and lysozyme (Lyso) in each lane (left to right: 1, 0.5, 0.25 and 0.125 μg per protein per lane) (see FIG. 37). Gels were stained for 1 h with the sensor solution. Gels were first de-stained with 50 mM NaOAc buffer pH 4.5 for 2 h and then with 50 mM NaOAc buffer pH 4.0 20% acetonitrile for 40 h. Gels that were stained with more than 1:1 equivalent of compound 8:GaCl₃, did not result in good selectivity for the β-casein protein. Staining of gel with 80 μM of compound 8 in complex with GaCl₃ (1:1 equivalent of compound 8:GaCl₃) for 1 hr, revealed higher selectivity for the target β-casein, which was improved upon destaining the gel for 2 h (FIG. 38, 1.0 μg per protein), and further improved following a 40 h destaining step, resulting in 4.5-fold selectivity for β-casein over a distally phosphorylated protein ovalbumin Example 20

On-Gel Multiplex Detection of Proximally Phosphorylated Protein Using Compound 8

Following staining of the gel with 80 μM of compound 8 in complex with GaCl₃ (1:1 equivalent of compound 8:GaCl₃) and 40 h destain in 50 mM NaOAc buffer pH 4.0 20% acetonitrile, and acquisition of the image, the gel was further de-stained from compound 8 in 2×PBS 20% DMSO for 1 h and stained with a SYPRO Ruby according to the manufacturer's protocol. As can be seen from FIG. 39, all four proteins were present in comparable amounts. Additionally, this experiment demonstrated that staining of gels with compound 8 in complex with GaCl₃ (1:1 equivalent of compound 8:GaCl₃) prior to the total protein analysis with SYPRO Ruby, does not interfere with the latter.

Example 20

On-Gel Detection of Proximally Phosphorylated Protein Using Compound 8

Compound 8 was dissolved in 100 mM NaOAc buffer, pH 4.5, 150 mM NaCl, 20% propylene glycol and combined with 10 and 15 μM GaCl₃ solutions. Each gel contained 4 lanes with equal amounts of BSA, ovalbumin (Ova), β-casein (β-cas) and lysozyme (Lyso) in each lane (FIG. 40) left to right: 1, 0.5, 0.25 and 0.125 μg per protein per lane). Gels were stained for 1.5 h with the sensor solution. Destaining was performed for variable time (specified at the top) with 50 mM NaOAc, pH 4.0, 20% acetonitrile. Gels were rinsed with MiliQ water for 5 min prior to imaging. Images were acquired using ChemiDoc MP, using a 530 nm emission filter and UV trans excitation.

Gels that were stained with both 1:1 and 1:1.5 equivalent of compound 8:GaCl₃ (no destaining), did not result in selective staining for the β-casein protein and the most intensively stained protein was lysozyme. However, following 16 h destain in 50 mM NaOAc, pH 4.0, 20% acetonitrile, the trend in staining has reversed and β-casein was the most prominently stained band (FIG. 41, 0.25 μg per perotein lane).

Example 21

On-Gel Detection of Proximally Phosphorylated Protein Using Compound 2

Compound 2 was dissolved in 50 mM NaOAc buffer, pH 4.5, 50 mM NaCl, 10% DMSO and combined with 80, 160 or and 240 μM GaCl₃ solutions. Each gel contained 4 lanes with equal amounts of BSA, ovalbumin (Ova), β-casein (β-cas) and lysozyme (Lyso) in each lane (left to right: 1, 0.5, 0.25 and 0.125 μg per protein per lane) (FIG. 42). Gels were stained for 1 h with the sensor solution. Gels were first de-stained with 50 mM NaOAc buffer pH 4.5 for 2 h and then with 50 mM NaOAc buffer pH 4.0 20% acetonitrile for 40 h. Gels that were stained with more than 1:1 equivalent of compound 2:GaCl₃, did not result in good selectivity for the β-casein protein. Staining of gel with 80 μM of compound 2 in complex with GaCl₃ (1:1 equivalent of compound 8:GaCl₃) for 1 hr, following a 2 h destaining step, did not result in the selective staining of β-casein (FIGS. 42 and 43). However with the increased destaining time the intensity of β-casein band relative to other proteins was increasing, resulting in a 6.7-fold higher intensity over the distally phosphorylated protein ovalbumin. Lane containing 1 μg of each protein was analyzed (FIG. 43).

Example 22

On-Gel Multiplex Detection of Proximally Phosphorylated Protein Using Compound 2

Following staining of the gel with 80 μM of compound 2 in complex with GaCl₃ (1:1 equivalent of compound 8:GaCl₃) and 40 h destain in 50 mM NaOAc buffer pH 4.0 20% acetonitrile, and acquisition of the image, the gel was further de-stained from compound 2 and stained with the total protein stain SYPRO Ruby according to the manufacturer's protocol. As can be seen from FIG. 44, all four proteins were present in comparable amounts. Additionally, this experiment demonstrated that staining of gels with compound 2 in complex with GaCl₃ (1:1 equivalent of compound 8:GaCl₃) prior to the total protein analysis with SYPRO Ruby, does not interfere with the latter.

Example 23

On-Gel Detection of Proximally Phosphorylated Protein Using Compound 2

Compound 2 was dissolved in 100 mM NaOAc buffer, pH 4.5, 150 mM NaCl, 20% propylene glycol and combined with 10 and 15 μM GaCl₃ solutions. Each gel contained 4 lanes with equal amounts of BSA, ovalbumin (Ova), β-casein (β-cas) and lysozyme (Lyso) in each lane (FIG. 45) left to right: 1, 0.5, 0.25 and 0.125 μg per protein per lane). Gels were stained for 1.5 h with the sensor solution. Destaining was performed for variable time (specified at the top) with 50 mM NaOAc, pH 4.0, 20% acetonitrile (see FIGS. 45 and 46). Gels were rinsed with MiliQ water for 5 min prior to imaging. Images were acquired using ChemiDoc MP, using a 530 nm emission filter and UV trans excitation. Gels that were stained with both 1:1 and 1:1.5 equivalent of compound 8:GaCl₃ (no destaining), did not result in selective staining for the β-casein protein. However, following 16 h destain in 50 mM NaOAc, pH 4.0, 20% acetonitrile, the trend in staining has changed significantly and β-casein was the most prominently stained band with 10-fold higher signal than a distally phosphorylated protein ovalbumin (FIG. 46).

Example 24

On-Gel Detection of Proximally Phosphorylated Protein Using Compound 2—pH Variability GaCl₃ was titrated into 40 μM (constant) of compound 2 from 500 to 0.25 μM at pH 4.5 (50 mM NaOAc) and 7.5

(HEPES). Fluorescence intensity was measured at 376 and 476 nm at 350 nm excitation. As can be seen from the resulting titration curve at 376 nm (FIG. 47), at pH 7.5 at higher concentration of GaCl$_3$, saturation was not observed. At pH 4.5 saturation is observed at 10 μM of GaCl$_3$.

Example 25

On-Gel Detection of Proximally Phosphorylated Protein Using Compound 3—pH Variability 40 μM of compound 3 was titrated with GaCl$_3$ (250-0.12 μM) and the change in emission at 376 nm was recorded upon excitation at 350 nm as shown in FIG. 48. Use of buffers at lower pH values (5.5 and 4.5, 50 mM NaOAc), [Ga$^{3+}$-compound 3] complex formation was observed at single-digit μM concentrations.

Example 26

On-Gel Detection of Proximally Phosphorylated Protein in Cell Lysates Using Compound 1

Using the developed multiplex method above, protein extracts obtained from different cancer lineages were analyzed for their profiles in proximal phosphorylation.

MDA-MB-231 (human breast adenocarcinoma), MRC-9 (human lung normal), MV-4-11 (human peripheral blood myelomonocytic leukaemia), MDA-MB-468 (human breast adenocarcinoma), K-562 (human bone marrow chronic myelogenous leukaemia), A549 (human lung carcinoma) and MDA-MB-435 (human breast ductal carcinoma) were used in this study.

MRC-9, MV-4-11 and K-562 were obtained from ATCC (cat. ATCC CCL-212, ATCC CRL-9591 and ATCC CCL-243, respectively). MDA-MB-231, MDA-MB-468, A549 and MDA-MB-435 were a generous gift from Dr. Leda Raptis, Queen's University.

MV-4-11 and K-562 cells were cultured in Iscove's modified Dulbecco's Medium (Gibco) supplemented with 10% FBS (Sigma Aldrich). MDA-MB-231, MRC-9, MDA-MB-468, A549 and MDA-MB-435 were grown in Dulbecco's Modified Eagles Medium (DMEM) supplemented with 10% FBS.

Cells were washed twice with ice cold 1× Dulbecco's Phosphate Buffered Saline (PBS) (Sigma Aldrich, cat. D1408) and cells were lysed using RIPA buffer containing protease and phosphatase inhibitor cocktail (Roche, cat. 11836153001 and 04906845001). Protein concentration in each cell lysate was quantified using the Thermo Scientific Pierce BCA Protein Assay Kit using the Microplate Procedure as according to the manufacturer's protocol (Thermo Scientific cat. 23225 or 23227). 10 well 30 μl Mini-PROTEAN TGX gel (Bio-Rad, cat. 456-1083) were used.

40 μg of protein lysate prepared from MDA-MB-231, MRC-9, MV-4-11, MDA-MB-468, K-562, A549 and MDA-MB-435 were combined 2:1 (v:v) with Native Sample Buffer for loading onto gel. BSA, ovalbumin, β-casein and Lysozyme were loaded as control proteins at 500 and 250 ng per protein. BLUeye Prestained Protein Ladder was included on gels. Gel was run at 110-150 V until bromophenol blue band ran off the gel.

Following separation, gel was fixed in 25 mL of 50% methanol (MeOH), 10% acetic acid (AcOH)) 2×30 min. Gel was washed in 25 mL of MilliQ water 3×10 min and then stained with 25 mL of 100 μM of compound 1 in complex with Zn$^{2+}$ (triflate salt) in pH 5.5 50 mM sodium acetate (NaOAc), 5% dimethyl sulfoxide (DMSO), 25 mM sodium chloride (NaCl) for 1 h protected from light. Gel was washed in 25 mL of MilliQ water 3×5 min and imaged on a Bio-Rad ChemiDoc MP using UV Trans illumination and 530/28 emission filter.

Following acquisition of image resulting from staining with compound 1 in complex with Zn$^{2+}$ (triflate salt), gel was de-stained in 25 mL of 2×PBS, 20% DMSO 3×20 min and then washed with 25 mL of MilliQ water 3×5 min to remove compound 1. The gel was then stained with Pro-Q Diamond Gel Stain (Life Technologies, cat. P33300), and imaged according to the manufacturer's protocol.

Subsequent staining by SYPRO Ruby Gel Stain Solution (Life Technologies, cat. S12000) and imaging was performed according to the manufacturer's protocol.

As seen from FIG. 49, significant differences in staining by compound 1 in complex with Zn$^{2+}$ are observed among cell lines derived from breast, lung, blood and skin cancers. Moreover, compound 1 in complex with Zn$^{2+}$ is also capable of detecting differences between cancer cells derived from the same organ (e.g. breast). Compound 1 in complex with Zn$^{2+}$ reveals a fingerprint unique to each cell line, which is unlike total phosphorylation (Pro-Q in FIG. 49) and total protein profiles (SYPRO in FIG. 49). Thus, compound 1 in complex with Zn$^{2+}$ is used for detection of subtle differences in the levels of proximal phosphorylation between cell lines.

Example 27

On-Membrane Detection of Proximally Phosphorylated Protein Using Compound 1

15 well 15 μl Mini-PROTEAN Precast Gel (Bio-Rad, cat. 456 1086) or 26 well 15 μl Criterion TGX Precast gel (Bio-Rad, cat. 567-1085) were used for control protein studies.

BSA (Sigma Aldrich, cat. A7030-10G), ovalbumin (Sigma Aldrich, cat. A5503-1G), β-casein (Sigma Aldrich, cat. C6905-250MG) and lysozyme (Sigma Aldrich, cat. L6876-1 G) were used as control proteins. For loading onto the gel, proteins were dissolved in 1×PBS and combined 2:1 with Native Sample Buffer (Bio-Rad, cat. 1610738). Each lane contained equal amounts of each of the four proteins. For the determination of detection limits protein amounts tested were 1, 0.5, 0.25 and 0.125, 0.063 and 0.031 μg per protein per lane. Each gel also contained BLUeye Prestained Protein Ladder (GeneDirex, cat. PM007-0500). The gel was run in 1×Tris/Glycine/SDS Buffer (Bio-Rad, cat. 161-0732) at 110-150 V until the bromophenol blue band ran off the gel.

The proteins were transferred to a Midi-size LF PVDF membrane available from Bio-Rad using the Bio-Rad Trans-Blot Turbo. The membrane was dipped in methanol and the proteins were fixed face down in 25 mL of 7% AcOH, 10% MeOH for 10 min. The membrane was washed face up in 25 mL of MilliQ water 4×5 min. The membrane was then stained in 25 mL of 20 μM of compound 1 in complex with Zn$^{2+}$ (triflate salt) in pH 5.5 50 mM NaOAc, 5% DMSO, 25 mM NaCl for 15 min. It was then de-stained in 25 mL of pH 5.5 50 mM NaOAc, 15% DMSO, 25 mM NaCl for 5 min followed by 2×5 min de-stain in 25 mL of pH 7.5 50 mM HEPES, 20% DMSO, 75 mM NaCl. The membrane was imaged while wet on a Bio-Rad ChemiDoc MP using UV Trans Illumination and a standard emission filter. Alternatively, membranes can be visualized under trans-UV illumination. As can be seen from FIG. 50, β-casein band was exclusively detected using this method, with the detection limit of approximately 30 ng.

Example 28

On-Membrane Multiplex Detection of Proximally Phosphorylated Protein Using Compound 1

Staining with compound 1 in complex with $Zn^{2+}$ (triflate salt) was performed as described in Example 27. Following acquisition of the image after staining with compound 1 in complex with $Zn^{2+}$ (triflate salt), without letting membrane to dry, it was de-stained of compound 1 by 3×10 min washes with 25 mL 2×PBS, 20% DMSO, followed by 3×5 min washes with 25 mL of MilliQ water. Alternatively, de-staining can be performed in pH 4.0 50 mM NaOAc, 20% ACN 3×10 min followed by 3×5 min washes with 25 mL of MilliQ water. Following that, Pro-Q Diamond blot stain protocol was carried out according to manufacturer's instructions (Life Technologies cat. P33356) starting from step 3.3. The membrane was imaged while wet using Green Epi illumination and a 605/50 emission filter. Following Pro-Q imaging, staining for total protein was carried out as described in the SYPRO Ruby blot stain manual (Life technologies, cat. S11791) skipping re-fixation step, as the membrane was still wet. The membrane was imaged using UV Trans illumination and a 605/50 emission filter.

FIG. 51 presents the resulting 3 images of the same gel following staining with compound 1 in complex with $Zn^{2+}$ (triflate salt), Pro-Q Diamond and SYPRO Ruby. Lanes 1, 2, 3, 4, 5 contain 1.0, 0.5, 0.25, 0.125 and 0.06 µg of protein, respectively. The analysis of the lane containing 500 ng of protein is also provided. FIG. 51 demonstrates that compound 1 in complex with $Zn^{2+}$, selectively detects proximally phosphorylated proteins over distally phosphorylated ones and non-phosphorylated proteins.

FIG. 52 shows over-laid fluorescent images of lane 2 (containing 0.5 µg of each protein) which were acquired following staining with compound 1 in complex with $Zn^{2+}$ (triflate salt), Pro-Q Diamond and SYPRO Ruby. When bands from the three channels are assigned different colors and overlaid, this results in a color-coded 3-way analysis of the lane. Thus, if compound 1 is assigned green color, red for Pro-Q Diamond and blue for SYPRO Ruby, following merging one can visualize proximally phosphorylated proteins in yellow (β-casein), distally-phosphorylated proteins in purple (ovalbumin) and non-phosphorylated proteins in blue (BSA and Lysozyme).

Example 29

On-Membrane Multiplex Detection of Proximally Phosphorylated Protein from Cell Lysate Using Compound 1—Western Blot Using the multiplex protocol for PVDF membranes in Example 28, same cell lines as used in example 26 were analyzed in gels. Methods for electrophoresis and electroblotting can be found in examples 26 and 28. Methods for staining with compound 1 and following multiplex analysis with Pro-Q Diamond and SYPRO Ruby can be found in example 28.

Consistent with gel results, staining with compound 1 in complex with $Zn^{2+}$ (triflate salt) revealed unique staining profiles for each cell line (FIG. 53). As a post-multiplex analysis, similar to gels, PVDF bands can be identified by MS.[13, 14]

Additionally, a PVDF membrane can be analyzed by Western blotting, a technique incompatible with gels. Thus, in order to demonstrate that the performed multiplex protocol does not interfere with the subsequent western blot analysis, w an antibody-based detection of β-actin was performed. Following acquisition of a SYPRO Ruby image, wet membrane was washed with 1×PBS 3×15 min. The blot was blocked in 5% milk in PBST for 1 h. After washing the blot with 1×PBST for 5 min, it was incubated o/n with 1:2500 β-actin mouse (Cell Signaling, cat. 3700S) in Super-Block Blocking Buffer (Thermo Scientific, cat. 37515). The blot was washed in 1×PBST 3×5 min and stained with 1:10,000 Anti-mouse Alexa 647 (Cell Signalling, cat. 4410S) in 1×PBST for 1 h. The blot was then washed in 1×PBST 3×5 min and imaged while wet with a Bio-Rad ChemiDoc MP using Red Epi Illumination and a 695/55 emission filter.

As can be seen in FIG. 54, following multiplex analysis, a β-actin protein was successfully detected by antibody, demonstrating the three-stain multiplex protocol performed prior to antibody-staining did not interfere with the latter.

Example 30

Fixed Cell Imaging Using Compound 1

MRC-9 cells were plated on an 8-chamber tissue culture treated glass slide (BD Falcon; 40,000 cells/chamber) and cultured for two days at 37° C., 5% $CO_2$. Media was removed and cells were incubated with 200 µL of 3.4% formaldehyde solution in 1×PBS for 10 min. Cells were washed 3×3 min with PBS and stored in PBS at 4° C. until staining. Cells were washed 3× with 50 mM HEPES and incubated in 40 µM solution of compound 1 in complex with $Zn^{2+}$ (triflate salt) dissolved in 50 mM HEPES, 75 mM NaCl, 10% DMSO for 1 h. Cells were rinsed 2× with 50 mM HEPES and mounted with a mounting solution and a cover slip.

As can be seen in FIG. 55, morphology of cells treated with compound 1-$Zn^{2+}$ complex, looks comparable to an untreated control under bright field (BF) microscope. Upon irradiation of cell with 370 nm light, bright blue intracellular fluorescence is observed in cells treated with compound 1-$Zn^{2+}$ complex but not in an untreated sample.

To be certain that the signal is specific to phosphorylation, cells were stained with compound 1 not complexed with a metal ion, as well as a pyrene derivative, which did not contain a metal-chelating moiety. As can be seen in FIG. 56, only compound 1-$Zn^{2+}$ complex, is capable of inducing intracellular fluorescence, which indicates that compounds of the disclosure target proximally phosphorylated proteins.

In order to assess if permeabilization of cells affects staining, MDA-MB-231 cells were incubated at rt in 0.2% Tween 20 (BIOSHOP) in 1×PBS for 4 minutes and washed four times with 1×PBS prior to staining with compound 1-$Zn^{2+}$ complex. As can be seen from FIG. 57, no difference in cellular staining was observed in permeabilized cells. Thus, staining could be performed on both permeabilized and intact cells, which allows great flexibility in the protocol design. Compounds of the disclosure, including compound 1-$Zn^{2+}$ complex resulted in similar response in other cell lines including those derived from normal and cancerous human lung tissues, MRC-9 and A549, respectively.

Example 31

Selective Imaging of RNA and Target Proteins in Fixed Cell Imaging Using Compound 1

In order to determine if the signal was a result of association with RNA, following permeabilization, MRC-9 cells were equilibrated in 2×SSC buffer (Ambion, cat. AM9763) and 150 μL of 100 μg/4 DNase-free RNase (Thermo Scientific, A/T1 mix) was added and incubated at 37° C., 5% $CO_2$ for 20 min. Cells were then rinsed twice with 2×SSC. Staining with compound 1-$Zn^{2+}$ complex was performed as described in example 32.

As can be seen from FIG. 58, the signal has been decreased upon treatment with RNase, which demonstrates that compound 1-$Zn^{2+}$ complex is partially detecting the proximally phosphorylated sites on the phosphate backbone of RNA. However, the signal has not been completely abolished, indicating that in RNase treated samples the signal is most likely resulting from the association with the proximally phosphorylated proteins. Thus, compounds of the disclosure, including compound 1-$Zn^{2+}$ complex, can be used for imaging RNA by avoiding treatment of samples with the RNase enzyme, while proximally phosphorylated proteins can be selectively imaged by pre-treatment of cells with RNAse.

Example 32

Fixed Cell Imaging Using Compound 1—Co-Staining

A binding solution of the disclosure was demonstrated to be compatible with other dyes, as exemplified by successful co-staining with the nuclear stain, propidium iodide (PI) (FIG. 59). MDA-MB-231 cells were permeabilized, treated with RNase and stained with compound 1-$Zn^{2+}$ complex (as described in example 32). Cells were then equilibrated in 2×SSC and incubated with 200 μL of 15 μM propidium iodide (Molecular Probes) for 5 min at rt. Cells were rinsed twice with 2×SSC. Cytoseal 280 (Thermo Scientific) mounting media was added following all staining and the slide was sealed with a micro cover glass (VWR)

Thus, it has been demonstrated that compound 1-$Zn^{2+}$ complex is compatible with other stains, including those which are imaged using red channel.

Example 33

Fixed Cell Imaging Using Compound 1—Monitoring Increase in Proximal Phosphorylation To demonstrate that ProxyPhos was sensitive to increases in proximal phosphorylation, we treated MRC-9 and A549 cell lines with a JAK2 pathway-inducing agent IL6,[15,16]. The fluorescent signal from compound 1-$Zn^{2+}$ was significantly increased in cells pre-treated with IL-6 (FIG. 60). Moreover, the signal could be quantified by demonstrating that A549 cell line was more susceptible towards treatment with IL-6 (FIG. 61).

Example 34

Fixed Cell Imaging Using Compound 1—Monitoring Decrease in Proximal Phosphorylation Conversely, pre-treatment of cells with the pan-kinase inhibitor, staurosporine,[17] prior to cell fixation, led to a time-dependent decrease in the fluorescence intensity of compound 1-$Zn^{2+}$ complex as compared to the untreated control (FIG. 62). (3 h prior to fixation, media was removed and 22 nM of Staurosporine (BioShop, cat. STA001) solution in fresh media was added and incubated at 37° C., 5% $CO_2$ for 3 h). Thus, it has been demonstrated that compounds of the disclosure, including compound 1-$Zn^{2+}$ complex, can be used to monitor the fluctuations in the amount of proximally di-phosphoyrlated sites in response to exogenous agents, including but not limited to drugs, inhibitors and pollutants.

Example 35

Live Cell Treatment Using Compound 1—Cytotoxicity

MRC-9 cells were cultured on 96-well tissue culture treated plates (10,000 cells per well) in 50 μL of regular media. Media was removed and replaced with 50 μl of compound 1-$Zn^{2+}$ complex (100 μM to 100 nM) in regular media. Following incubation for 2.5 h, 5.5 h, 24 h and 4 days, cell viability was estimated using CellTiter-Blue Reagent (Promega, cat. G808A) according to the manufacturer's protocol.

Compound 1-$Zn^{2+}$ complex was not significantly cytotoxic to normal human lung cells after 24 h of incubation at 100 μM (FIG. 63). Cytotoxicity was only observed after 4 days of incubation. Additionally, compound 1-$Zn^{2+}$ complex was readily cell-permeable to live cells with significant intracellular uptake within 1 h of treatment, which was further increased upon 19 h incubation (FIG. 64). Thus, it has been demonstrated that compounds of the disclosure can be used for monitoring intra-cellular differences in proximal phosphorylation using a robust method, which allows for great flexibility in the experimental design.

Example 36

Live Cell Imaging Using Compound 1

MRC-9 cells were cultured on 96 well tissue culture treated plates in regular media. Media was removed and 100 μL of 25 μM of compound 1-$Zn^{2+}$ complex in clear media (Gibco, cat. 21063-029) was added to each well. Cells with compound 1-$Zn^{2+}$ complex were incubated under regular cell culturing conditions for variable time (FIG. 64) until imaging. Cells were imaged without removing the compound 1-$Zn^{2+}$ complex solution.

As can be seen from FIG. 64, rapid uptake of compound 1-$Zn^{2+}$ complex is observed within 1 h, which is then significantly increased at 19 h of incubation. This demonstrates that compounds of the disclosure, including compound 1 1-$Zn^{2+}$ complex, are readily cell-permeable and live cell imaging experiments can be conducted over a broad time-frame.

Example 37

Photosensitivity of Compound 1

Compound 1 in complex with Zn2+ (triflate salt) was shown to induce photosensitivity in cells upon exposure to light in the trans-UV region. Incubation of live MRC-9 cells with 25 μM of compound 1 complexed with $Zn^{2+}$ (triflate salt) in regular culturing media, following exposure to Trans-UV/violet light, significant changes in morphology were observed (FIG. 65). This effect is not observed under the same conditions when cells are not exposed to trans-UV/Violet light, or upon excitation with blue light. This effect is also not observed upon exposure to trans-UV/short wave violet light in the absence of compound 1 complexed with $Zn^{2+}$ (triflate salt). Thus, it has been demonstrated that compounds of the disclosure, including compound 1 complexed with $Zn^{2+}$ (triflate salt), can serve as efficient photosensitizers.

Example 38

Detection of Proximally Phosphorylated Protein Immobilized on Solid Support Using Compound 1

Proximally phosphorylated α-casein and β-casein proteins, distally phosphorylated ovalbumin and non-phosphorylated BSA and lysozyme were dissolved in PBS at a concentration of 1 mg/mL and 12 1:1 serial dilutions were made. 90 μL of each of the serially diluted protein were transferred to a high-binding COSTAR 96-well black plate and incubated overnight at 4° C. overnight to allow for the adherence of proteins to the surface of the plate. 100 μL of 200 μM of compound 1-$Zn^{2+}$ in pH 7.5 50 mM HEPES, 75 mM NaCl, 10% DMSO was added to all wells and incubated for 20 min. The binding solution was removed and replaced with 100 μL of 50 mM HEPES pH 7.5 and incubated for 10 min. Fluorescence emission was recorded using 350 nm excitation and 476 nm emission (20 nm bandwidth). As expected, α-casein possessing the most proximally phosphorylated sites induced the highest signal, followed by β-casein. This was observed across all concentrations tested. Using these conditions, as low as 4.1 pmol of a proximally phosphorylated protein could be detected (FIG. 66). This experiment demonstrates that a binding solution of this disclosure can be used for the detection of proximally phosphorylated targets immobilized on a solid support.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Select optimization conditions tested for in-solution detection of proximally phosphorylated proteins and peptides

| | | Conditions tested pH | | | | | |
|---|---|---|---|---|---|---|---|
| | | 7.5 | 6.5 | 5.5 | 4.5 | 3.5 | |
| Parameter | Variable | HEPES | | Sodium acetate | | | |
| Ionic strength/ polarity | [NaCl] mM | 0 | 25 | 50 | 75 | 100 | 120 |
| Hydrophobicity | Propylene glycol | 0 | 5 | 10 | 15 | 20 | 25 |
| | DMSO | 0 | 5 | 10 | 15 | 20 | 25 |

TABLE 2

Phosphorylation profiles of proteins used for In-Solution Detection of Proximal Phosphorylation

| Protein | Organism | Uniprot reference | Phosphosites |
|---|---|---|---|
| BSA | Bos taurus | P02769 | N/A |
| Lysozyme | Gallus gallus | P00698 | |
| Ovalbumin | Gallus gallus | P01012 | pS69; pS345 |
| β-casein | Bos taurus | P02666 | pS30, pS32, pS33, pS34, pS50 |
| α-casein S1 | Bos taurus | P02662 | pS56, pS61, pS63, pS79, pS81, pS82, pS83, pS90, pS130 |
| α-casein S2 | Bos taurus | P02663 | pS23, pS24, pS25, pS28, pS46, pS71, pS72, pS73, pS76, pS158 |

TABLE 3

Conditions tested for in-solution detection of proximally phosphorylated proteins and peptides

| | | Conditions tested pH | | | | | |
|---|---|---|---|---|---|---|---|
| | | 7.5 | 6.5 | 5.5 | 4.5 | 3.5 | |
| Parameter | Variable | HEPES | | Sodium acetate | | | |
| Ionic strength/ polarity | [NaCl] mM | 0 | 25 | 50 | 75 | 100 | 120 |
| Hydrophobicity | Propylene glycol | 0 | 5 | 10 | 15 | 20 | 25 |
| | DMSO | 0 | 5 | 10 | 15 | 20 | 25 |

TABLE 4

Mass spectrometry identification of proteins following in-gel multiplex analysis

| Modified sequence | Charge | Intensity | Protein | Phosphorylation site* |
|---|---|---|---|---|
| _DIGS(ph)ES(ph)TEDQAM(ox)EDIK_ | 2 | 29,357,000 | α-casein s1 | 61, 63 |
| _EQLS(ph)TS(ph)EENSKK_ | 2 | 27,806,000 | α-casein s2 | 144, 146 |
| _TVDM(ox)ES(ph)TEVFTK_ | 2 | 9,055,400 | α-casein s2 | 158 |
| _EQLSTS(ph)EENSKK_ | 2 | 8,353,600 | α-casein s2 | 146 |
| _EQLS(ph)TS(ph)EENSK_ | 2 | 4,451,800 | α-casein s2 | 144, 146 |
| _NM(ox)AINPS(ph)KENLCSTFCK_ | 3 | 2,255,400 | α-casein s2 | 46 |

*assignment was performed using PhosphositePlus or Uniprot databases. Only peptides with intensity over 2,000,000 are shown.

REFERENCES CITED HEREIN AND INCORPORATED BY REFERENCE

1. Hunter, T. Protein kinases and phosphatases: the yin and yang of protein phosphorylation and signaling. *Cell* 80, 225-236 (1995).
2. Cohen, P. Protein kinases—the major drug targets of the twenty-first century? *Nat Rev Drug Discov* 1, 309-315 (2002).
3. Su, H.-C., Hutchison, C. A. & Giddings, M. C. Mapping phosphoproteins in *Mycoplasma genitalium* and *Mycoplasma pneumoniae*. *BMC Microbiol.* 7, 63 (2007).
4. Orsatti, L. et al. 2-D Difference in gel electrophoresis combined with Pro-Q Diamond staining: A successful approach for the identification of kinase/phosphatase targets. *ELECTROPHORESIS* 30, 2469-2476 (2009).
5. Steinberg, T. H. et al. Global quantitative phosphoprotein analysis using Multiplexed Proteomics technology. *Proteomics* 3, 1128-1144 (2003).
6. Lucet, I. S. et al. The structural basis of Janus kinase 2 inhibition by a potent and specific pan-Janus kinase inhibitor. *Blood* 107, 176-183 (2006).
7. Dephoure, N. et al. A quantitative atlas of mitotic phosphorylation. *Proc. Natl. Acad. Sci. U.S.A.* 105, 10762-10767 (2008).
8. Schmidt, F., Stadlbauer, S. & König, B. Zinc-cyclen coordination to UTP, TTP or pyrophosphate induces pyrene excimer emission. *Dalton Trans.* 39, 7250-7261 (2010).
9. Cho, H. K., Lee, D. H. & Hong, J.-I. A fluorescent pyrophosphate sensor via excimer formation in water. *Chem. Commun. (Camb.)* 1690-1692 (2005). doi: 10.1039/b417845a

The invention claimed is:

1. A method of detecting RNA or proximally phosphorylated polypeptides, comprising:

(a) contacting a sample with an excimer forming compound of the Formula I $$W-V-[Y]_n \qquad (I)$$

wherein,
    W is an excimer forming fluorophore;
    V is a linker moiety, wherein the linker moiety is $C_{1-10}$-alkylene;
    Y is a metal ion coordinating moiety having the structure

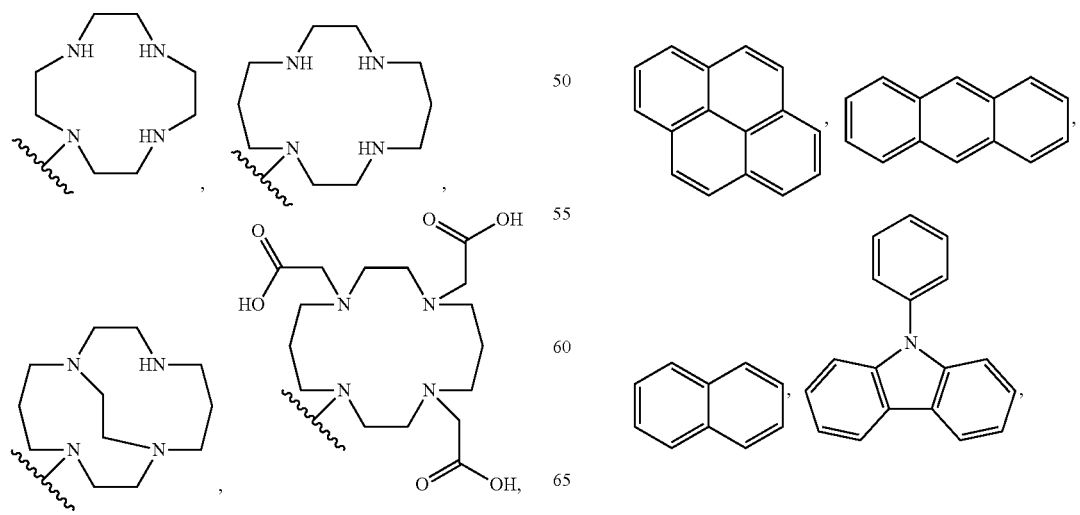

and n is 1, 2 or 3; and a suitable metal ion;

(b) detecting a fluorescence signal at a wavelength specific for the excimer forming fluorophore of the compound;
    (c) comparing the fluorescence signal of (b) with the fluorescence intensity of a control sample;
    wherein detection of a signal in the sample having a fluorescence intensity greater than the control sample indicates that the sample contains RNA or a proximally phosphorylated polypeptide.

2. The method of claim 1, wherein the excimer forming fluorophore is optionally substituted $C_{10-40}$-aryl or optionally substituted $C_{9-40}$-heteroaryl, wherein the optional substituents are selected from halo, carboxy, hydroxyl, $C_{1-20}$-alkyl, $C_{2-20}$-alkenyl, $C_{2-20}$-alkynyl, $C_{3-20}$cycloalkyl, $C_{1-20}$alkoxy, —NR'R", $C_{6-14}$-aryl, and $C_{5-14}$-heteroaryl, wherein R' and R" are simultaneously or independently H or $C_{1-6}$alkyl.

3. The method of claim 2, wherein the excimer forming fluorophore is optionally substituted

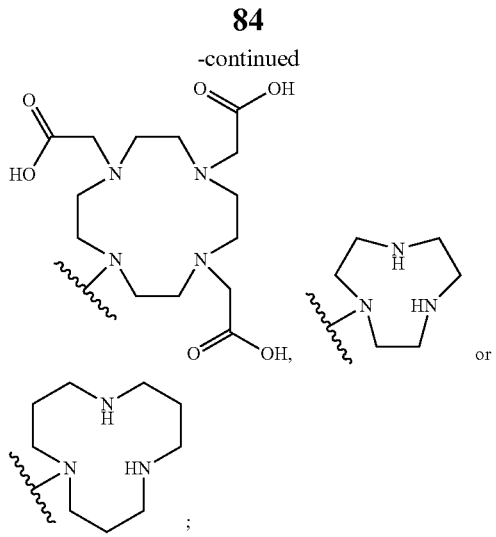

-continued

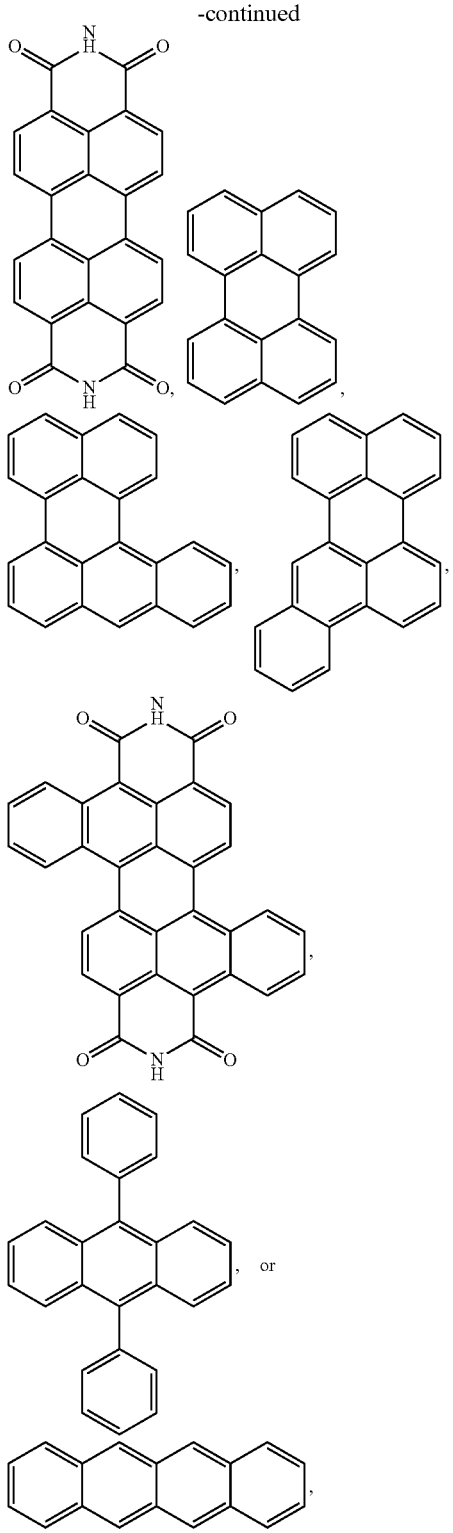

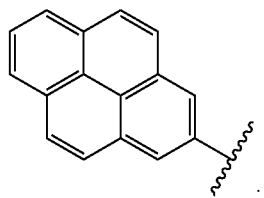 [SMILES: *c1cc2ccc3cccc4ccc(c1)c2c34]

5. The method of claim 1, wherein the linker moiety is $C_{1-6}$-alkylene.

6. The method of claim 1, wherein the compound is compound 1

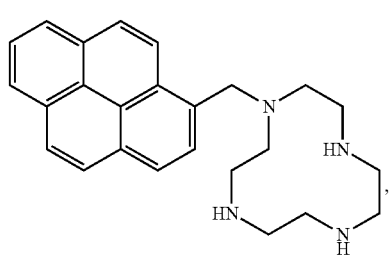

compound 4

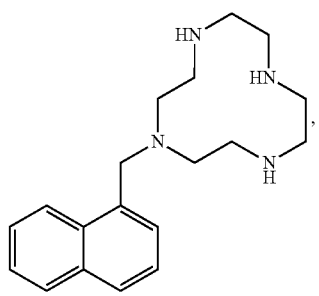

compound 5

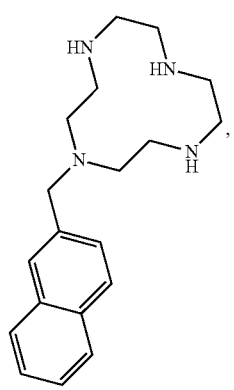

compound 9

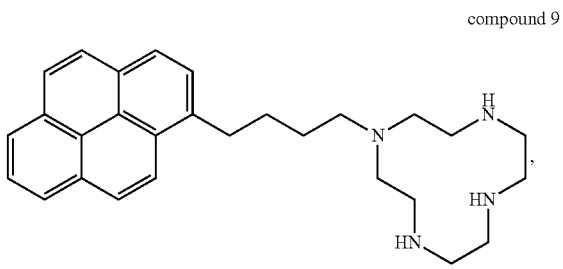

wherein the optional substituents are selected from halo, carboxy, hydroxyl, $C_{1-20}$-alkyl, $C_{2-20}$-alkenyl, $C_{2-20}$-alkynyl, $C_{3-20}$cycloalkyl, $C_{1-20}$alkoxy, —NR'R" $C_{6-14}$-aryl, and $C_{5-14}$-heteroaryl, wherein R' and R" are simultaneously or independently H or $C_{1-6}$alkyl.

4. The method of claim 3, wherein the wherein the excimer forming fluorophore is substituted or unsubstituted -continued compound 12

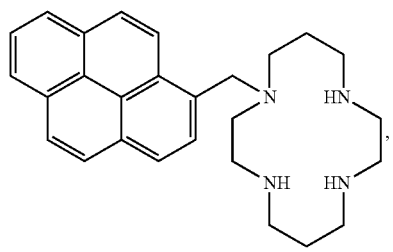

or compound 13

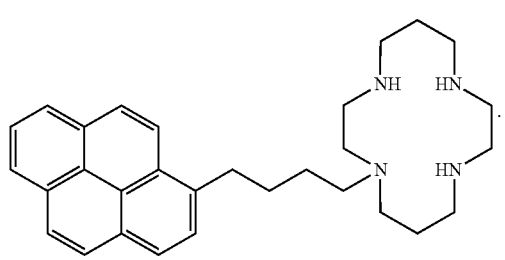

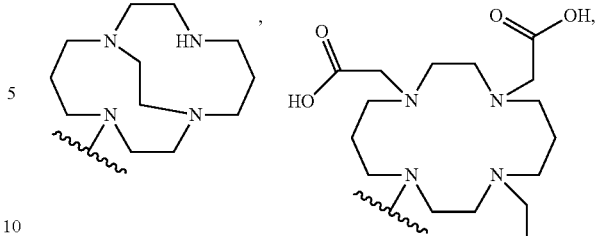

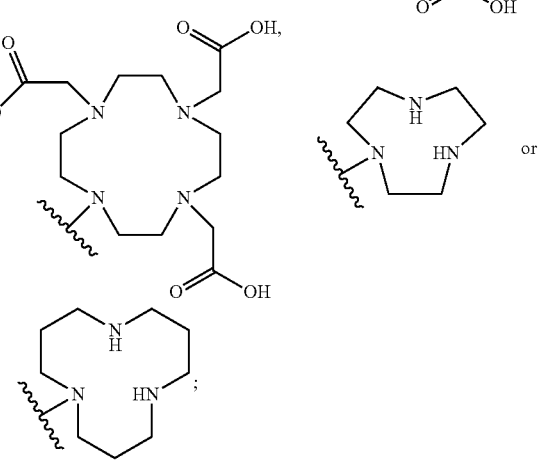

and
n is 1, 2 or 3; and
a suitable metal ion;
(b) detecting a fluorescence signal at a wavelength specific for the excimer forming fluorophore of the compound;
(c) comparing the fluorescence signal of (b) with the fluorescence intensity of a control sample containing known quantities of RNA or proximally phosphorylated polypeptides;
wherein detection of a signal having a fluorescence intensity similar to the control sample indicates that the sample contains RNA or proximally phosphorylated polypeptides.

13. A method of monitoring the activity of a kinase or phosphatase protein, the method comprising:
(a) contacting a sample of the kinase or phosphatase protein with an excimer forming compound of the Formula I W—V—[Y]$_n$      (I)

wherein
W is an excimer forming fluorophore;
V is a linker moiety, wherein the linker moiety is C$_{1-10}$-alkylene;
Y is a metal ion coordinating moiety having the structure

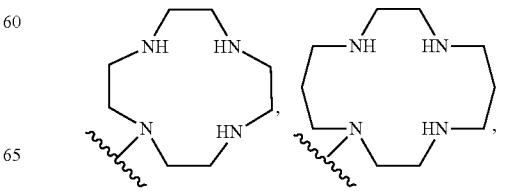

7. The method of claim 1, wherein the metal ion is a transition metal ion, a lanthanide metal ion or a post-transition metal ion.

8. The method of claim 7, wherein the transition metal ion is Zn(II), Cu(II), Mn(II), Fe(II), Fe(III) or Ni(II) and the post-transition metal ion is Ga(III), Al(III), and the lanthanide metal ion is Tb (III).

9. The method of claim 1, wherein the sample is a bodily sample.

10. The method of claim 9, wherein the bodily sample is urine, synovial fluid or blood.

11. The method of claim 1, wherein the proximally phosphorylated polypeptide comprises amino acids that are proximally phosphorylated within 1-6 amino acid residues of each other.

12. A method of quantifying RNA or proximally phosphorylated polypeptides, comprising:
(a) contacting a sample with an excimer forming compound of the Formula I W—V—[Y]$_n$      (I)

wherein
W is an excimer forming fluorophore;
V is a linker moiety, wherein the linker moiety is C$_{1-10}$-alkylene;
Y is a metal ion coordinating moiety having the structure

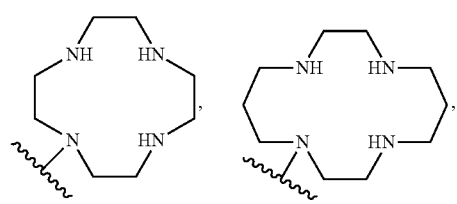

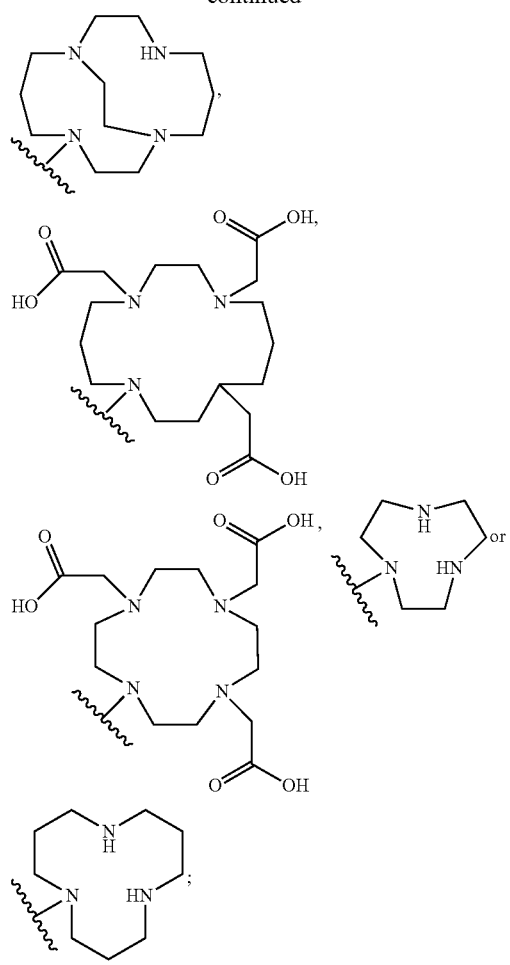

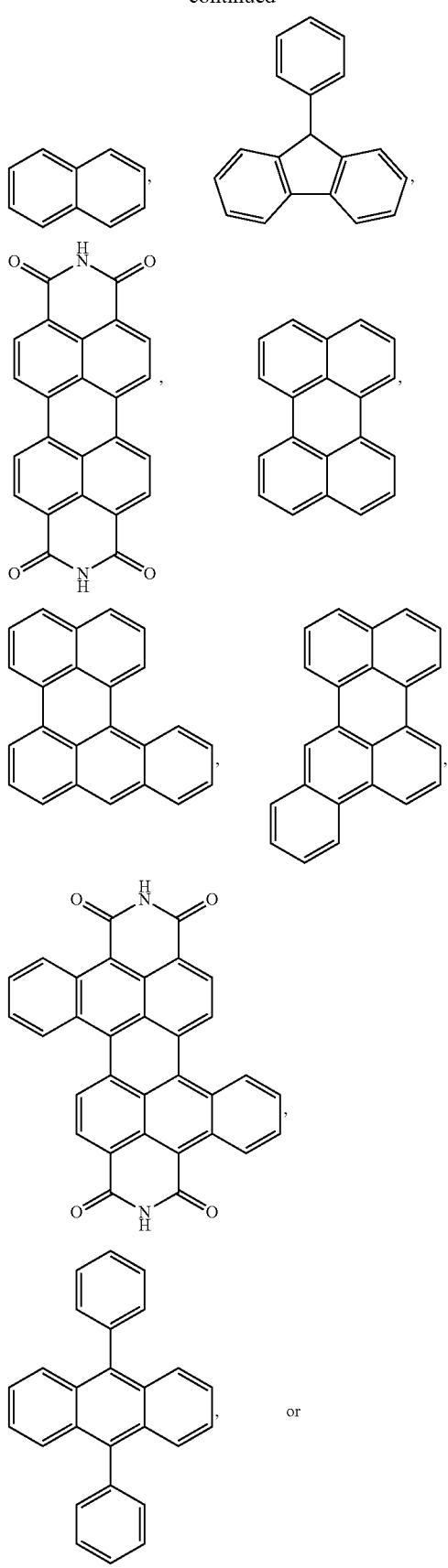

and n is 1 2 or 3; and a suitable metal ion;

(b) detecting a fluorescence signal at a wavelength specific for the excimer forming fluorophore of the compound;

(c) comparing the fluorescence signal of (b) with the fluorescence intensity of an unactivated protein sample;

wherein detection of a signal having a fluorescence intensity greater than the inactivated protein sample indicates that the protein sample is activated.

14. The method of claim 12, wherein the excimer forming fluorophore is optionally substituted

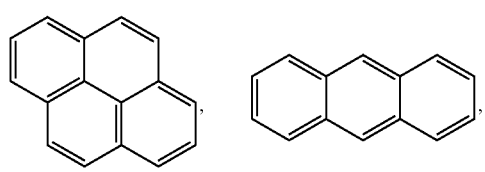

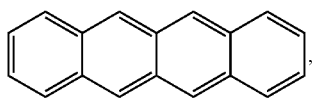

wherein the optional substituents are selected from halo, carboxy, hydroxyl, $C_{1-20}$-alkyl, $C_{2-20}$-alkenyl, $C_{2-20}$-alkynyl, $C_{3-20}$cycloalkyl, $C_{1-20}$alkoxy, —NR'R" $C_{6-14}$-aryl, and $C_{5-14}$-heteroaryl, wherein R' and R" are simultaneously or independently H or $C_{1-6}$alkyl.

15. The method of claim 14, wherein the wherein the excimer forming fluorophore is substituted or unsubstituted

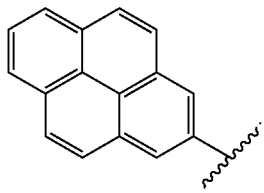 [SMILES: *c1cc2ccc3cccc4ccc(c1)c2c34]

16. The method of claim 12, wherein the compound is compound 1

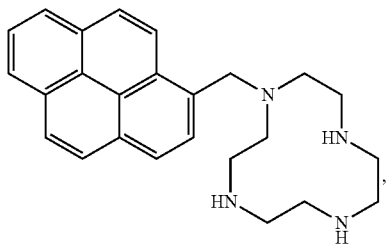

compound 4

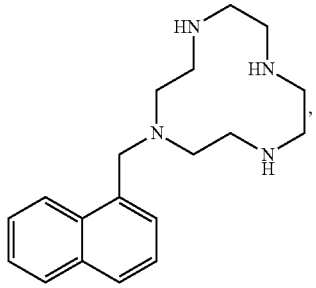

compound 5

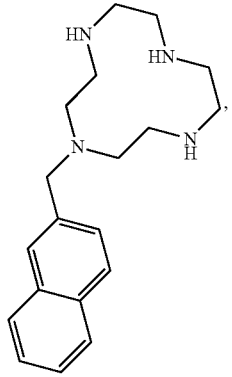

compound 9

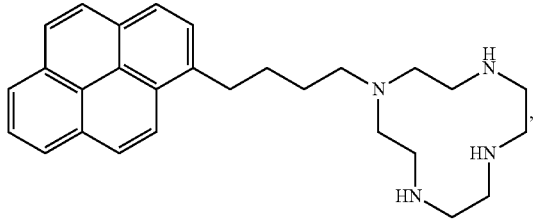

compound 12

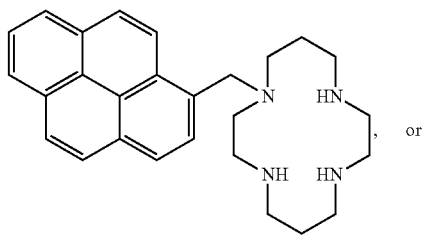

compound 13

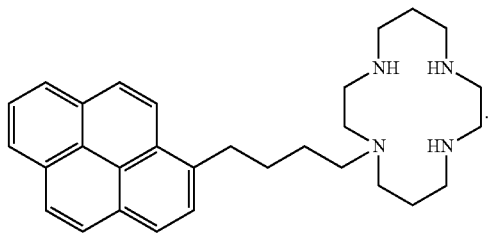

17. The method of claim 12, wherein the wherein the metal ion is a transition metal ion, a lanthanide metal ion or a post-transition metal ion, and wherein the transition metal ion is Zn(II), Cu(II), Mn(II), Fe(II), Fe(III) or Ni(II) and the post-transition metal ion is Ga(III), Al(III), and the lanthanide metal ion is Tb (III).

18. The method of claim 13, wherein the excimer forming fluorophore is optionally substituted

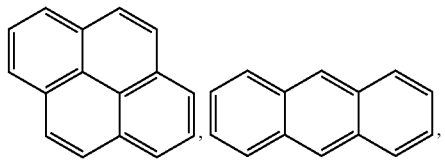

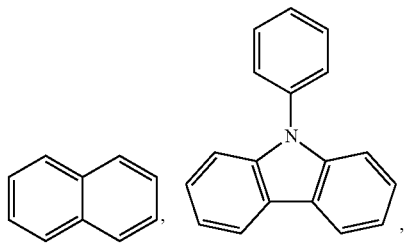

-continued
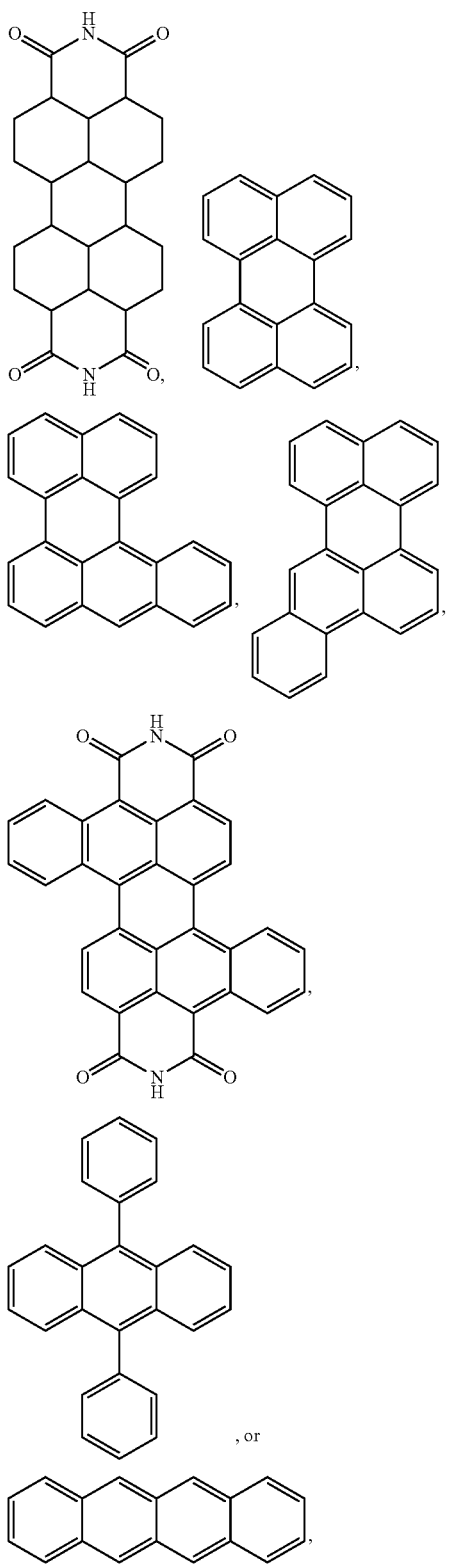
wherein the optional substituents are selected from halo, carboxy, hydroxyl, $C_{1-20}$-alkyl, $C_{2-20}$-alkenyl, $C_{2-20}$-alkynyl, $C_{3-20}$cycloalkyl, $C_{1-20}$alkoxy, —NR'R" $C_{6-14}$-aryl, and $C_{5-14}$-heteroaryl, wherein R' and R" are simultaneously or independently H or $C_{1-6}$alkyl.
19. The method of claim 13, wherein the compound is
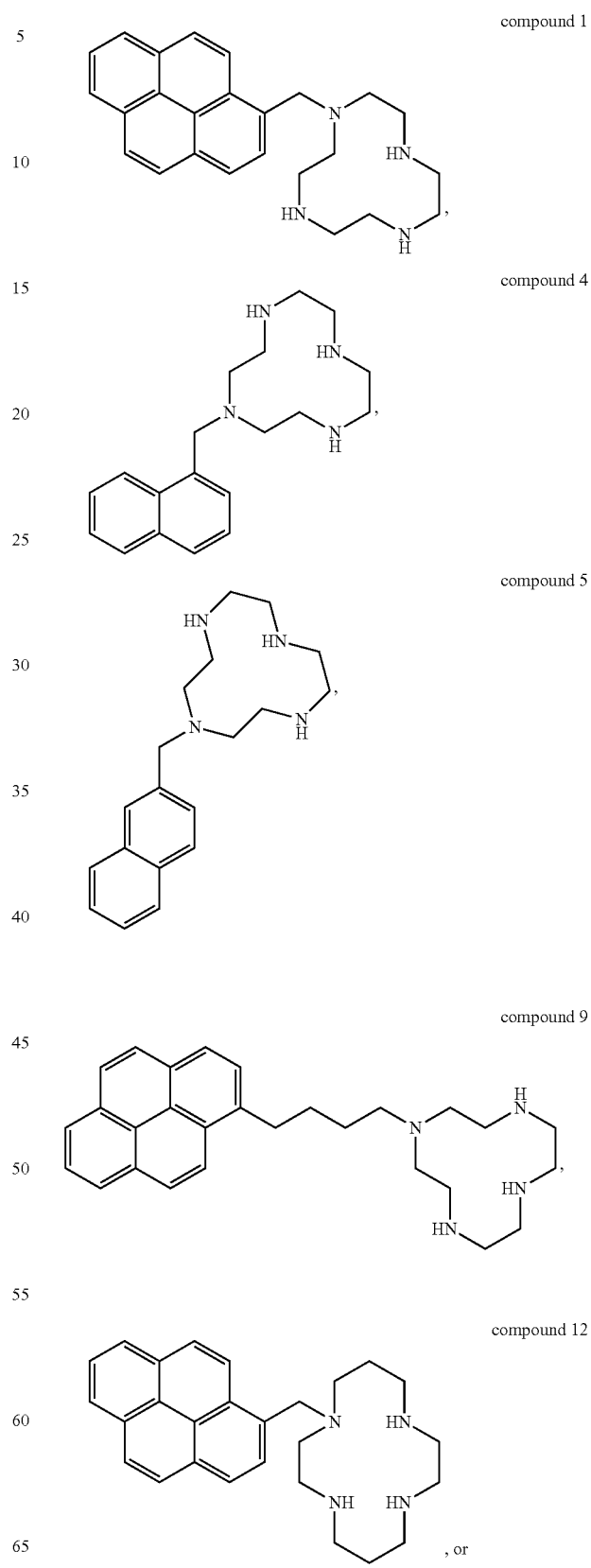

compound 13
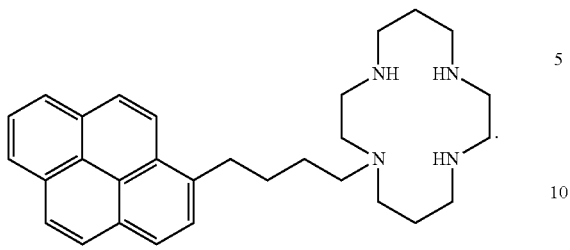
20. The method of claim 13, wherein the wherein the metal ion is a transition metal ion, a lanthanide metal ion or a post-transition metal ion, and wherein the transition metal ion is Zn(II), Cu(II), Mn(II), Fe(II), Fe(III) or Ni(II) and the post-transition metal ion is Ga(III), Al(III), and the lanthanide metal ion is Tb (III).
* * * * *

UNITED STATES PATENT AND TRADEMARK OFFICE
CERTIFICATE OF CORRECTION

PATENT NO. : 10,889,554 B2
APPLICATION NO. : 15/102953
DATED : January 12, 2021
INVENTOR(S) : Patrick Thomas Gunning and Dziyana Kraskouskaya It is certified that error appears in the above-identified patent and that said Letters Patent is hereby corrected as shown below:

In the Claims

Claim 14, Column 89, Line 60:

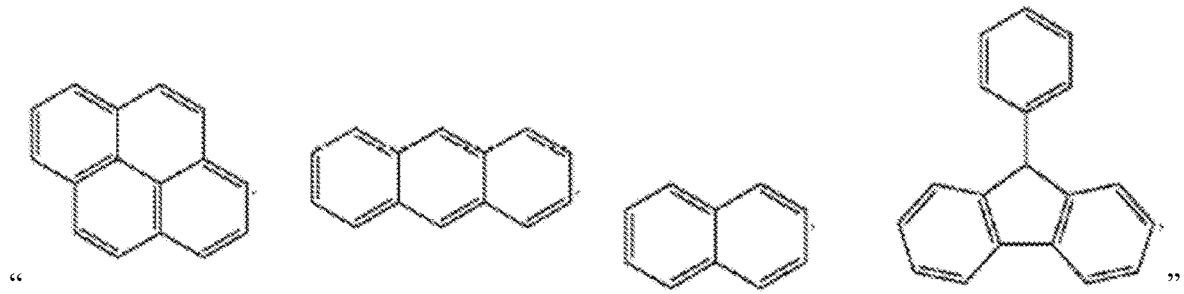

"

Should read:

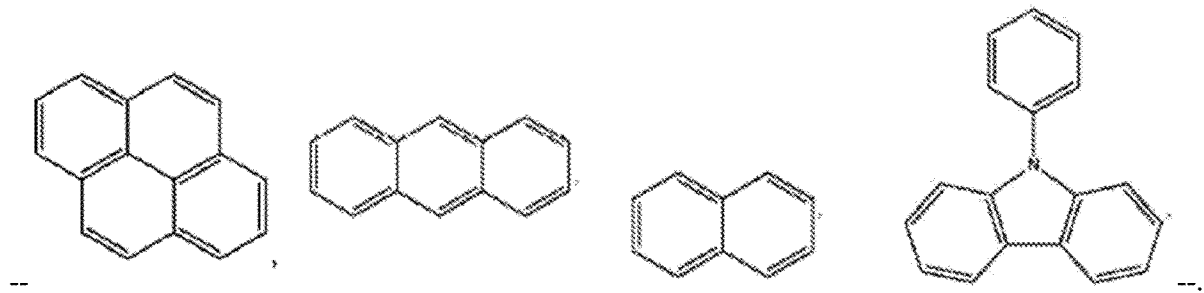

--.

Signed and Sealed this
Fourth Day of May, 2021

Drew Hirshfeld
*Performing the Functions and Duties of the
Under Secretary of Commerce for Intellectual Property and
Director of the United States Patent and Trademark Office*

Column 18, Column 93, Line 1:
" 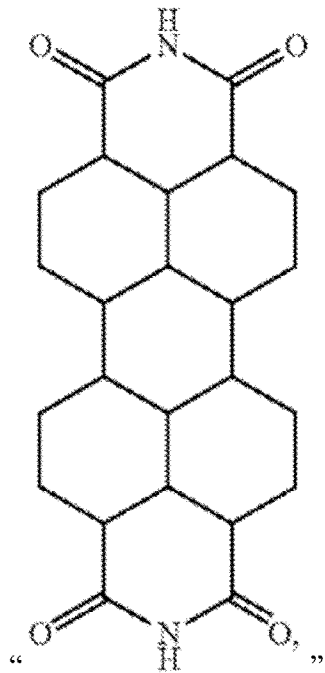 "
Should read:
-- 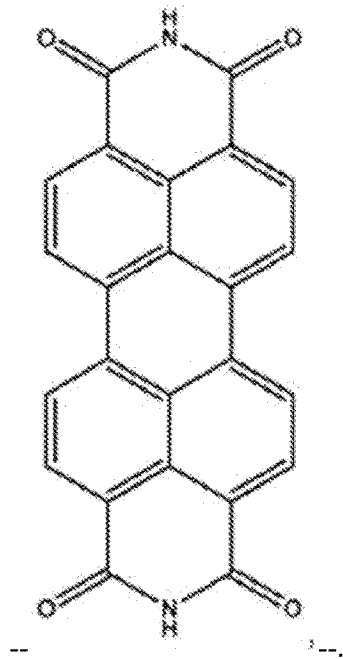 --.